United States Patent
Waer et al.

(10) Patent No.: US 6,946,465 B2
(45) Date of Patent: Sep. 20, 2005

(54) IMMUNOSUPPRESSIVE EFFECTS OF PTERIDINE DERIVATIVES

(75) Inventors: Mark Jozef Albert Waer, Heverlee (BE); Piet André Maurits Maria Herdewijn, Rotselaar/Wezemaal (BE); Wolfgang Eugen Pfleiderer, Constance (DE)

(73) Assignee: 4 AZA Bioscience NV, Leuven (BE)

( * ) Notice: Subject to any disclaimer, the term of this patent is extended or adjusted under 35 U.S.C. 154(b) by 0 days.

(21) Appl. No.: 10/444,158

(22) Filed: May 23, 2003

(65) Prior Publication Data

US 2003/0236255 A1 Dec. 25, 2003

Related U.S. Application Data

(63) Continuation-in-part of application No. 09/890,500, filed as application No. PCT/EP00/00938 on Feb. 2, 2000, now abandoned.
(60) Provisional application No. 60/118,282, filed on Feb. 2, 1999, provisional application No. 60/118,235, filed on Feb. 2, 1999, and provisional application No. 60/118,295, filed on Feb. 2, 1999.

(51) Int. Cl.[7] .................... C07D 475/02; A61K 31/519
(52) U.S. Cl. ........................................ 514/249; 544/257
(58) Field of Search .............................. 514/251, 257, 514/249; 544/249, 251, 257

(56) References Cited

U.S. PATENT DOCUMENTS

| | | | |
|---|---|---|---|
| 3,071,587 A | 1/1963 | Curran et al. ................ | 514/249 |
| 3,162,635 A | * 12/1964 | Schroeder .................... | 544/257 |
| 5,641,783 A | 6/1997 | Klein et al. ................... | 544/257 |
| 5,843,943 A | 12/1998 | Carson et al. ......... | 514/263.35 |

FOREIGN PATENT DOCUMENTS

| | | |
|---|---|---|
| EP | 0290189 | 11/1998 |
| WO | WO 94/06431 | 3/1994 |

(Continued)

OTHER PUBLICATIONS

Cottam, H.B. et al, J. Med. Chem., 39(1), 2–9, 1996.*

(Continued)

*Primary Examiner*—Thomas C. McKenzie
(74) *Attorney, Agent, or Firm*—Clark & Elbing LLP

(57) ABSTRACT

Novel poly-substituted pteridinediones (lumazines), and mono- or polysubstituted 2-thiolumazines, 4-thiolumazines or 2,4-dithiolumazines, having disclosed substituents in positions 1, 3, 6 and 7 of the pteridine ring, and pharmaceutically acceptable salts thereof, being represented by the general formula (I).

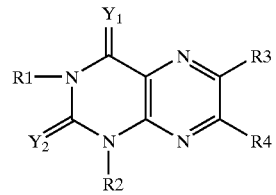

are useful as biologically active ingredients in preparing pharmaceutical compositions especially for the treatment or prevention of a CNS disorder, a cell proliferative disorder, a viral infection, an immune or auto-immune disorder or a transplant rejection. Combinations of the pteridine derivatives of the invention with an immunosuppressant or immunomodulator drug, an antineoplastic drug or an antiviral agent, providing potential synergistic effects, are also disclosed.

8 Claims, 5 Drawing Sheets

FOREIGN PATENT DOCUMENTS

| WO | WO 94/11001 | 5/1994 | |
| --- | --- | --- | --- |
| WO | WO 9411001 | 5/1994 | .......... A61K/31/53 |
| WO | WO 94/22449 | 10/1994 | |
| WO | WO 9422449 | 10/1994 | .......... A61K/31/52 |
| WO | WO 95/13075 | 5/1995 | |
| WO | WO 9513075 | 5/1995 | .......... A61K/31/52 |
| WO | WO 95/31469 | 11/1995 | |
| WO | WO 9531469 | 11/1995 | ........... C07H/19/22 |
| WO | WO 96/10568 | 4/1996 | |
| WO | WO 9610568 | 4/1996 | ......... C07D/295/15 |
| WO | WO 96/20710 | 7/1996 | |
| WO | WO 9620710 | 7/1996 | .......... A61K/31/52 |
| WO | WO 98/52948 | 11/1998 | |
| WO | WO 9852948 | 11/1998 | ......... C07D/473/02 |
| WO | WO 00/45800 | 8/2000 | |
| WO | WO 0045800 | 8/2000 | .......... A61K/31/00 |

OTHER PUBLICATIONS

C. Robin Ganellin, "Final Report on the Activities of the Medicinal Chemistry Section", [online]. Jan. 14, 2002 [retrieved on Jun. 2, 2004]. Ret'rieved from the Internet <www.iupac.org/divisions/VII/VII.M/VIIM–ReportDec2001.pdf>.*

Sugimoto, Takashi; Seo, Chihiro; Murata, Shizuaki; Pfleiderer, Wolfgang, Pteridines (1997), 8(3), 188–194.*

Abou–Hadeed, Khaled; Pfleiderer, Wolfgang, Pteridines (1996), 7(4), 113–122.*

Giori, P.; Poli, T.; Veronese, A. C.; Vicentini, C. B.; Manfrini, M.; Guarneri, M., Journal of Heterocyclic Chemistry, 23(6), 1661–5 (English) 1986.*

Vinot, Nicole Bulletin de la Societe Chimique de France (1973), (9–10, Pt. 2), 2752–5.*

Buu–Ho~et al., "Phthalonimides (1,3,4–Trioxo–1,2,3,4–tetrahydroisoquinolines) of Potential Biological Interest," J. Heretocycl. Chem., 1968, 5:545–546.

Database Beilstein; accession nos. 285496, 252276, 250719, 1957.

Database Beilstein; accession nos. 533693, 540145, 1960.

Database Beilstein; accession nos. 6337777, 6373242, 1992.

Database Beilstein; accession no. 7216143, 1995.

Database Beilstein; accession no. 7928670, 1998.

Database Beilstein; accession nos. 9571456, 9570157, 2003.

Murata et al., "A Facile Method for Regioselective 6,7–disubstitution of Pteridine," Heterocycles, 2000, 53:1259–1262.

Sato, et al., "Studies on Pyrazines. Part 37. Synthesis of 6–propionylpteridine–2, 4(1H, 3H)–dione and Its 1–and/or 3–methyl Derivatives from Marine Natural Products," J. Chem. Soc., Perkin Trans. 2000, 1:89–95.

Cottam et al., "Substituted Xamthines, Pteridinediones, and Related Compounds ad Potential Antiinflammatory Agents. Synthesis and Biological Evaluation of Inhibitors of Tumor Necrosis Factor α," J. Med. Chem., vol. 39, pp. 2–9, 1996.

Buu–Hoi et al., "Phthalonimides (1,3,4,Trioxo–1,2,3,4–tetrahydroisoquinolines) of Potential Biological Interest," J. Heretocycl. Chem., vol. 5, No. 4, pp. 545–546, 1968.

* cited by examiner

IMMUNOSUPPRESSIVE EFFECTS OF PTERIDINE DERIVATIVES

CROSS REFERENCE TO RELATED APPLICATIONS

This application is a continuation-in-part of U.S. application Ser. No. 09/890,500, filed Oct. 30, 2001, abandoned, which is the National Stage of International Application No. PCT/EP00/00938, filed Feb. 2, 2000, which was published in English under PCT Article 21(2), and which claims the benefit of U.S. Provisional Application Nos. 60/118,235, 60/118,282, and 60/118,295, each filed Feb. 2, 1999; the disclosures of which are incorporated by reference in their entirety.

The invention relates to a class of novel poly-substituted pteridine-2,4-diones (lumazines), as well as novel mono- and polysubstituted 2-thiolumazines, 4-thiolumazines and 2,4-dithiolumazines. The invention further relates to pharmaceutical compositions including a broad class of poly-substituted pteridine-2,4-diones (lumazines), as well as mono- and polysubstituted 2-thiolumazines, 4-thiolumazines and 2,4-dithiolumazines especially for the prevention and/or the treatment of pathologic conditions such as, but not limited to, immune and autoimmune disorders, organ and cells transplant rejections, cell proliferative disorders, cardiovascular disorders, disorders of the central nervous system and viral diseases.

The invention further relates to combined pharmaceutical preparations comprising one or more polysubstituted pteridine-2,4-diones (lumazines), as well as mono- and polysubstituted 2-thiolumazines, 4-thiolumazines and 2,4-dithiolumazines and one or more known immunosuppressant drugs or antineoplastic drugs or anti-viral drugs.

This invention also relates to a method for the prevention and/or treatment of pathologic conditions such as, but not limited to, immune and autoimmune disorders, organ and cells transplant rejections, cell proliferative disorders, cardiovascular disorders, disorders of the central nervous system and viral diseases by the administration of an effective amount of a polysubstituted pteridine-2,4-dione (lumazine), or a mono- or polysubstituted 2-thiolumazine, 4-thiolumazine or 2,4-dithio-lumazine optionally combined with one or more known immunosuppressant drugs or antineoplastic drugs or anti-viral drugs. Finally the invention relates to a method for selecting or classifying biologically active polysubstituted pteridine-2,4-diones (lumazines), as well as mono- and polysubstituted 2-thiolumazines, 4-thiolumazines and 2,4-dithiolumazines based on the determination of two or more lymphocyte activation in vitro tests.

BACKGROUND OF THE INVENTION 2,4-dioxo-1,2,3,4-tetrahydropteridine is well known in the art under the name lumazine. Gabriel and Sonn first disclosed in *Ber. Deut. Chem. Ges.* (1907) 40:4850 making lumazine from pyrazin-bicarboxamide. Timmis in *Nature* (1949) 164:139 disclosed the synthesis of 1,3-dimethyl-6-phenyllumazine and 1,3-dimethyl-7-phenyl-lumazine by condensing a 6-amino-5-nitroso-pyrimidine with benzaldehyde or methylphenylketone respectively. Zondler et al. in *J. Heterocyclic Chem.* (1967) 4:124 and Taylor et al. in Heterocycles (1978) 10:37 disclosed 1,3,6-trimethyllumazine and 1,3-dimethyl-6-ethyllumazine. Yoneda and Higuchi in *J. Chem. Soc.* Perkin (1977) 1336 disclosed the preparation of various 1,3-dimethyl-6-aryllumazines starting from 6-amino-1,3-dimethyl-5-aryliden-aminouracil. Kang et al. in *J. Heterocycl. Chem.* (1987) 24:597–601 disclosed reacting 5,6-diamino-1,3-dimethyluracil either with propanetrione-1,3-dioxime followed by cyclization to form 1,3-dimethyllumazine-6-carboxaldoxime, or with oximinoacetone followed by cyclization to form 1,3,6-trimethyllumazine, or else with methylglyoxal to form 1,3,7-trimethyllumazine. Both latter compounds may easily, through acid hydrolysis in the presence of formaldehyde, be converted into the corresponding 1,3-dimethyllumazine-carboxaldehydes which, due to their high carbonyl reactivity, may in turn be converted into other lumazine derivatives. Blicke et al. in *J.A.C.S* (1954) 76:2798–2800 disclosed 1,3-dimethyl-7-aminolumazine, 1,3,6,7-tetramethyllumazine, 1,3-dimethyl-6,7-dihydroxylumazine and 1,3-dimethyl-6,7-diphenyllumazine; Pfleiderer in *Chem. Ber.* (1957) 90:2588 disclosed 1,3-dimethyl-6-hydroxylumazine and 1,3-dimethyl-7-hydroxylumazine; Pfleiderer et al. in *Chem. Ber.* (1973) 106:3149–3174 disclosed 1,3-dimethyl-6-hydroxy-7-phenyllumazine, 1,3-dimethyl-6-phenyl-7-hydroxylumazine and 1,3-dimethyl-6,7-diisopropyllumazine; Hutzenlaub et al. in *Chem. Ber.* (1973) 106:3203–3215 disclosed 1,3-dimethyl-7-methoxylumazine, 1,3,6-trimethyl-7-hydroxy-lumazine and 1,3,6-trimethyl-7-methoxylumazine; Steppan et al. in *Liebigs Ann. Chem.* (1982) 2135–2145 disclosed 1,3-dimethyl-6-aminolumazine, 1,3-dimethyl-6-chlorolumazine, 1,3-dimethyl-7-chlorolumazine and 1,3-dimethyl-7-methylaminolumazine; Kasimierczuk et al. in *Chem. Ber.* (1979) 112:1499–1513 disclosed 1,3-dimethyl-7-mercaptolumazine and 1,3-dimethyl-7-methylthio-lumazine as well as a few substituted 2- or 4-thiolumazines and 2,4-dithiolumazines, starting from substituted 6-amino-2-thiouracil or 6-amino-2,4-dithiouracil; Eisele et al. in *Pteridines* (1993) 4:178–186 disclosed 1,3,6-trimethyllumazine-7-carboxylic acid and its methyl and ethyl esters. Perez-Rubalcaba et al. in *Liebigs Ann. Chem.* (1983) 852–859 disclosed substituted 3-methyllumazines wherein one of the 6- and 7-substituents is phenyl whereas the other is chloro. Finally, Weisenfeldt (1987) disclosed a series of tetra-substituted lumazines wherein the 1- and 3-substituents are methyl and one of the 6- and 7-substituents is chloro. Further, Fink et al. in *Chem. Berichte* (1963) 96:2950–2963, as well as Pfleiderer, Perez-Rubalcaba and Eisele (all cited supra) disclosed bi- and tri-substituted lumazines wherein only one of the 1- and 3-nitrogen atoms is substituted. Interestingly, none of the above-cited substituted lumazines, 2-thiolumazines and 2,4-dithiolumazines was ever said to have any kind of biological activity.

A few other substituted pteridine-2,4-diones (lumazines) are already known in the art as being useful in the preparation of medicines. For instance, U.S. Pat. No. 3,071,587 teaches cyanoethylpteridinediones having central nervous system (hereinafter referred as CNS) activity and anti-depressant properties. WO 94/06431 teaches a 1-methyl-3-(10,11-epoxyundecyl)pteridinedione being able to inhibit IL-1 receptors, decrease proliferation of tumor & other cells, stimulate hematopoeisis, suppress T-cell activation, secretion of antibodies by B-cells and activation of macrophage or endothelial cells by endotoxins, tumor necrosis factor (hereinafter TNF), IL-1 or GM-CSF and enhance resistance of mesenchymal cells to TNF. WO 94/11001 teaches 1-methyl-3-(hydroxy- and dihydroxy-$C_{9-25}$ alkyl) pteridinediones being able to inhibit lysophosphatidic acid transferase as well as immune or cellular response to stimuli, and therefore can be used to treat tumor progression or invasion, autoimmune diseases, acute allergic reactions mediated by TNF or IL-1, rheumatoid arthritis, osteoarthritis, multiple sclerosis, diabetes, atherosclerosis, restenosis, stroke, HIV infection, inflammatory response, septic shock, CNS and bone diseases. Cottam et al. in *J. Med. Chem.* (1996) 39 :2–9 and WO 98/52948 both disclose a 1-methyl-3-n-hexyl-6-carboxymethyl-7-carboxymethyl pteridinedione which, although included in a biological evaluation study of inhibitors of TNF-α, was not tested for TNF-α activity. WO 96/20710 teaches substituted pteridinediones which inhibit cellular responses to ceramide metabolites of the sphingomyelin signal transduction pathway, inhibit inflammatory response associated with TNF-α and fibroblast proliferation or UV-induced cutaneous immune suppression and therefore can be used to treat cirrhosis, cell senescence and apoptosis.

Nevertheless, there still is a need in the art for specific and highly therapeutically active compounds, such as, but not limited to, drugs for treating immune and autoimmune disorders, organ and cells transplant rejections, cell proliferative disorders, cardiovascular disorders, disorders of the central nervous system and viral diseases. In particular, there is a need in the art to provide immunosuppressive compounds or antineoplastic drugs or anti-viral drugs which are active in a minor dose in order to replace existing drugs having significant side effects and to decrease treatment costs.

Currently used immunosuppressive drugs include antiproliferative agents, such as methotrexate, azathioprine, and cyclophosphamide. Since these drugs affect mitosis and cell division, they have severe toxic effects on normal cells with high turn-over rate such as bone marrow cells and the gastrointestinal tract lining. Accordingly, marrow depression and liver damage are common side effects.

Anti-inflammatory compounds used to induce immunosuppression include adrenocortical steroids such as dexamethasone and prednisolone. The common side effects observed with the use of these compounds are frequent infections, abnormal metabolism, hypertension, and diabetes.

Other immunosuppressive compounds currently used to inhibit lymphocyte activation and subsequent proliferation include cyclosporine, tacrolimus and rapamycin. Cyclosporine and its relatives are among the most commonly used immunosuppressant drugs. Cyclosporine is typically used for preventing or treating organ rejection in kidney, liver, heart, pancreas, bone marrow, and heart-lung transplants, as well as for the treatment of autoimmune and inflammatory diseases such as Crohn's disease, aplastic anemia, multiple-sclerosis, myasthenia gravis, uveitis, biliary cirrhosis, etc. However, cyclosporines suffer from a small therapeutic dose window and severe toxic effects including nephrotoxicity, hepatotoxicity, hypertension, hirsutism, cancer, and neurotoxicity.

Additionally, monoclonal antibodies with immunosuppressant properties, such as OKT3, have been used to prevent and/or treat graft rejection. Introduction of such monoclonal antibodies into a patient, as with many biological materials, induces several side-effects, such as dyspnea. Within the context of many life-threatening diseases, organ transplantation is considered a standard treatment and, in many cases, the only alternative to death. The immune response to foreign cell surface antigens on the graft, encoded by the major histo-compatibility complex (hereinafter referred as MHC) and present on all cells, generally precludes successful transplantation of tissues and organs unless the transplant tissues come from a compatible donor and the normal immune response is suppressed. Other than identical twins, the best compatibility and thus, long term rates of engraftment, are achieved using MHC identical sibling donors or MHC identical unrelated cadaver donors. However, such ideal matches are difficult to achieve. Further, with the increasing need of donor organs an increasing shortage of transplanted organs currently exists. Accordingly, xenotransplantation has emerged as an area of intensive study, but faces many hurdles with regard to rejection within the recipient organism.

The host response to an organ allograft involves a complex series of cellular interactions among T and B lymphocytes as well as macrophages or dendritic cells that recognize and are activated by foreign antigen. Co-stimulatory factors, primarily cytokines, and specific cell-cell interactions, provided by activated accessory cells such as macrophages or dendritic cells are essential for T-cell proliferation. These macrophages and dendritic cells either directly adhere to T-cells through specific adhesion proteins or secrete cytokines that stimulate T-cells, such as IL-12 and IL-15. Accessory cell-derived co-stimulatory signals stimulate activation of interleukin-2 (IL-2) gene transcription and expression of high affinity IL-2 receptors in T-cells. IL-2 is secreted by T lymphocytes upon antigen stimulation and is required for normal immune responsiveness. IL-2 stimulates lymphoid cells to proliferate and differentiate by binding to IL-2 specific cell surface receptors (IL-2R). IL-2 also initiates helper T-cell activation of cytotoxic T-cells and stimulates secretion of interferon-γ which in turn activates cytodestructive properties of macrophages. Furthermore, IFN-γ and IL-4 are also important activators of MHC class II expression in the transplanted organ, thereby further expanding the rejection cascade by enhancing the immunogenicity of the grafted organ The current model of a T-cell mediated response suggests that T-cells are primed in the T-cell zone of secondary lymphoid organs, primarily by dendritic cells. The initial interaction requires cell to cell contact between antigen-loaded MHC molecules on antigen-presenting cells (hereinafter referred as APC) and the T-cell receptor/CD3 complex on T-cells. Engagement of the TCR/CD3 complex induces CD154 expression predominantly on CD4 T-cells that in turn activate the APC through CD40 engagement, leading to improved antigen presentation. This is caused partly by upregulation of CD80 and CD86 expression on the APC, both of which are ligands for the important CD28 co-stimulatory molecule on T-cells. However, engagement of CD40 also leads to prolonged surface expression of MHC-antigen complexes, expression of ligands for 4-1BB and OX-40 (potent co-stimulatory molecules expressed on activated T-cells). Furthermore, CD40 engagement leads to secretion of various cytokines (e.g., IL-12, IL-15, TNF-α, IL-1, IL-6, and IL-8) and chemokines, all of which have important effects on both APC and T-cell activation and maturation. Similar mechanisms are involved in the development of auto-immune disease, such as type I diabetes. In humans and non-obese diabetic mice, insulin-dependent diabetes mellitus results from a spontaneous T-cell dependent auto-immune destruction of insulin-producing pancreatic .beta. cells that intensifies with age. The process is preceded by infiltration of the islets with mononuclear cells (insulitis), primarily composed of T lymphocytes. A delicate balance between auto-aggressive T-cells and suppressor-type immune phenomena determine whether expression of auto-immunity is limited to insulitis or not. Therapeutic strategies that target T-cells have been successful in preventing further progress of the auto-immune disease. These include neonatal thymectomy, administration of cyclosporine, and infusion of anti-pan T-cell, anti-CD4, or anti-CD25 (IL-2R) monoclonal antibodies. The aim of all rejection prevention and auto-immunity reversal strategies is to suppress the patient's immune reactivity to the antigenic tissue or agent, with a minimum of morbidity and mortality. Accordingly, a number of drugs are currently being used or investigated for their immunosuppressive properties. As discussed above, the most commonly used immunosuppressant is cyclosporine, which however has numerous side effects. Accordingly, in view of the relatively few choices for agents effective at immunosuppression with low toxicity profiles and manageable side effects, there exists a need in the art for identification of alternative immunosuppressive agents and for agents acting as complement to calcineurin inhibition.

There is also a need in the art to improve therapeutic efficiency by providing pharmaceutical compositions or combined preparations exhibiting a synergistic effect as a result of combining two or more immunosuppressant drugs, or antineoplastic drugs or anti-viral drugs.

SUMMARY OF THE INVENTION

In a first embodiment, the present invention relates to a group of novel poly-substituted pteridine-2,4-diones (lumazines), as well as novel mono- and poly-substituted 2-thiolumazines, 4-thiolumazines and 2,4-dithiolumazines and their pharmaceutically acceptable salts and enantiomers. These compounds may be represented by the general formula (I):

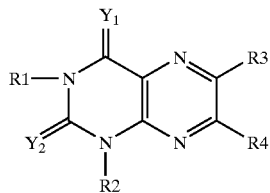

wherein:
a) if $Y_1$ and $Y_2$ are both oxygen and $R_4$ is hydrogen, then:
  $R_1$ is a radical selected from the group consisting of hydrogen; $C_{1-5}$ alkyl; $C_{2-7}$ alkenyl; aryl; alkylaryl; ω-hydroxy $C_{1-5}$ alkyl; ω-epoxy $C_{1-5}$ alkyl; ω-carboxy $C_{1-5}$ alkyl (wherein the carboxy group may be acid, ester or amide); and optionally substituted heterocyclic radicals selected from the group consisting of oxabicycloheptyl, azabenzimidazolyl, azacycloheptyl, azacyclooctyl, azacyclononyl, azabicyclononyl, tetrahydropyranyl, tetrahydropyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl, phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, benzothienyl, quinolyl, quinazolinyl, quinoxalinyl, carbazolyl, phenoxazinyl, phenothiazinyl, xanthenyl, purinyl, benzothienyl, naphtothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, thietyl and thietanyl;

$R_2$ is a radical selected from the group consisting of hydrogen; $C_{1-5}$ alkyl; $C_{2-7}$ alkenyl; aryl; alkylaryl; ω-hydroxy $C_{1-5}$ alkyl; ω-epoxy $C_{1-5}$ alkyl; and optionally substituted heterocyclic radicals;

at most one of $R_1$ and $R_2$ is hydrogen; and $R_3$ is an atom or radical selected from the group consisting of fluorine; iodine; $C_{3-4}$ alkyl; $C_{2-7}$ alkenyl; $C_{2-7}$ alkynyl; $C_{3-4}$ haloalkyl; $C_{1-2}$ haloalkyl wherein halo is fluoro or chloro; $C_{1-4}$ alkoxy; $C_{3-10}$ cycloalkoxy; aryloxy; arylalkyloxy; oxyheterocyclic; heterocyclic-substituted alkyloxy; thio $C_{1-7}$ alkyl; thio $C_{3-10}$ cycloalkyl; thioaryl; thioheterocyclic; arylalkylthio; heterocyclic-substituted alkylthio; hydroxylamino; acetal; carboxylic acid esters, thioesters and amides; thiocarboxylic acid; thiocarboxylic acid esters, thioesters and amides; sulfhydryl; $C_{2-7}$ alkylamino; cycloalkylamino; alkenylamino; cycloalkenylamino; alkynylamino; arylamino; arylalkylamino; hydroxyalkylamino; mercaptoalkylamino; heterocyclic amino; heterocyclic-substituted alkylamino; oximino; alkyloximino; hydrazino; alkylhydrazino; phenylhydrazino; cysteinyl acid, esters or amides; aromatic ring substituted with one or more substituents selected from the group consisting of halogen, $C_{1-4}$ alkyl, $C_{3-7}$ alkenyl, $C_{2-7}$ alkynyl, $C_{1-4}$ haloalkyl, $C_{2-4}$ alkoxy, hydroxyl, sulfhydryl, amino, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, carboxylic acid or esters or thioesters or amides thereof, thiocarboxylic acid or esters or thioesters or amides thereof, $C_{1-7}$ alkylamino, cycloalkylamino, alkenylamino, cycloalkenylamino, alkynylamino, arylamino, arylalkylamino, hydroxylalkylamino, mercaptoalkylamino, heterocyclic amino, hydrazino, alkylhydrazino and phenylhydrazino; heterocyclic substituents; aromatic or heterocyclic substituents substituted with an aliphatic spacer between the pteridine ring and the aromatic or heterocyclic substituent, whereby said aliphatic spacer is a branched or straight, saturated or unsaturated aliphatic chain of 2 to 4 carbon atoms which may contain one or more functions, atoms or radicals selected from the group consisting of carbonyl (oxo), alcohol (hydroxyl), ether, acetal, amino, imino, oximino, alkyloximino, amino-acid, cyano, carboxylic acid or ester or thioester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino, phenylhydrazino, sulfonyl, sulfonamido and halogen, or whereby said aliphatic spacer is a methylene group containing a function, atom or radical chosen from the group consisting of carbonyl (oxo), alcohol (hydroxyl), ether, acetal, amino, imino, oximino, alkyloximino, amino-acid, cyano, carboxylic acid or ester or thioester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino, phenylhydrazino, sulfonyl, sulfonamido and halogen; branched or straight, saturated or unsaturated aliphatic chain of 3 to 7 carbon atoms containing one or more functions selected from the group consisting of carbonyl (oxo), alcohol (hydroxyl), ether, acetal, amino, imino, oximino, alkyloximino, amino-acid, cyano, carboxylic acid ester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxylalkylamino, mercaptoalkyl-amino, heterocyclic amino, hydrazino, alkylhydrazino, phenylhydrazino, sulfonyl, sulfonamido and halogen; hydroxyethyl; oximinoethyl; alkyloximinoethyl; and methyl or ethyl or ethenyl containing one or more atoms, functions or radicals selected from the group consisting of ether, acetal, amino, imino, amino-acid, cyano, carboxylic acid or ester or thioester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylalkyl-amino, hydroxyalkylamino, mercaptoalkylamino, heterocyclic amino, hydrazino, alkylhydrazino, phenylhydrazino, sulfonyl, sulfonamido, fluoro and chloro;

b) if $Y_1$ and $Y_2$ are both oxygen and $R_3$ is hydrogen, then:

$R_1$ is a radical selected from the group consisting of hydrogen; $C_{1-5}$ alkyl; $C_{2-7}$ alkenyl; aryl; alkylaryl; ω-hydroxy $C_{1-5}$ alkyl; ω-epoxy $C_{1-5}$ alkyl; ω-carboxy $C_{1-5}$ alkyl (wherein the carboxy group may be acid, ester or amide); and optionally substituted heterocyclic radicals selected from the group consisting of oxabicycloheptyl, azabenzimidazolyl, azacycloheptyl, azacyclooctyl, azacyclononyl, azabicyclononyl, tetrahydropyranyl, tetrahydropyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl, phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, benzothienyl, quinolyl, quinazolinyl, quinoxalinyl, carbazolyl, phenoxazinyl, phenothiazinyl, xanthenyl, purinyl, benzothienyl, naphthothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, thietyl and thietanyl;

$R_2$ is a radical selected from the group consisting of hydrogen; $C_{1-5}$ alkyl; $C_{2-7}$ alkenyl; aryl; alkylaryl; ω-hydroxy $C_{1-5}$ alkyl; ω-epoxy $C_{1-5}$ alkyl; and optionally substituted heterocyclic radicals;

at most one of $R_1$ and $R_2$ is hydrogen; and $R_4$ is an atom or radical selected from the group consisting of fluorine; iodine; $C_{3-4}$ alkyl; $C_{2-7}$ alkenyl; $C_{2-7}$ alkynyl; halo $C_{3-4}$ alkyl; halo $C_{1-2}$ alkyl wherein halo is fluoro or chloro; $C_{1-4}$ alkoxy; $C_{3-10}$ cycloalkoxy; aryloxy; arylalkyloxy; oxyheterocyclic; heterocyclic-substituted alkyloxy; thio $C_{1-7}$ alkyl; thio $C_{3-10}$ cycloalkyl; thioaryl; thioheterocyclic; arylalkylthio; heterocyclic-substituted alkylthio; hydroxylamino; acetal; carboxylic acid esters, thioesters and amides; thiocarboxylic acid; thiocarboxylic acid esters, thioesters and amides; sulfhydryl; $C_{2-7}$ alkylamino; cycloalkylamino; alkenylamino; cycloalkenylamino; alkynylamino; arylamino; arylalkylamino; hydroxy-alkylamino; mercaptoalkyl-amino; heterocyclic amino; heterocyclic-substituted alkylamino; oximino; alkyloximino; hydrazino; alkylhydrazino; phenylhydrazino; cysteinyl acid, esters or amides; aromatic ring substituted with one or more substituents selected from the group consisting of halogen, nitro, $C_{1-4}$ alkyl, $C_{2-7}$ alkenyl, $C_{2-7}$ alkynyl, halo $C_{1-4}$ alkyl, $C_{2-4}$ alkoxy, hydroxyl, sulfhydryl, amino, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, carboxylic acid or esters or thioesters or amides thereof, thiocarboxylic acid or esters or thioesters or amides thereof, $C_{1-7}$ alkylamino, cycloalkylamino, alkenylamino, cycloalkenylamino, alkynylamino, arylamino, arylalkylamino, hydroxylalkylamino, mercaptoalkylamino, heterocyclic amino, hydrazino, alkylhydrazino and phenylhydrazino; optionally substituted heterocyclic substituents selected from the group consisting of oxabicycloheptyl, azabenzimidazolyl, azacycloheptyl, azacyclooctyl, azacyclononyl, azabicyclononyl, tetrahydrofuryl, tetrahydropyranyl, tetrahydropyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl, phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, imidazolyl, pyrazolyl, thiazolyl, thiadiazolyl, isothiazolyl, oxazolyl, oxadiazolyl, pyrrolyl, furyl, dihydrofuryl, furoyl, dioxolyl, dithienyl, dithiinyl, thienyl, indolyl, indazolyl, benzofuryl, benzothienyl, quinolyl, quinazolinyl, quinoxalinyl, carbazolyl, phenoxazinyl, phenothiazinyl, xanthenyl, purinyl, benzothienyl, naphtothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, benzimidazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, thietyl and thietanyl; aromatic or heterocyclic substituents substituted with an aliphatic spacer between the pteridine ring and the aromatic or heterocyclic substituent, whereby said aliphatic spacer is a branched or straight, saturated or unsaturated aliphatic chain of 2 to 4 carbon atoms which may contain one or more functions, atoms or radicals selected from the group consisting of carbonyl (oxo), alcohol (hydroxyl), ether, acetal, amino, imino, oximino, alkyloximino, amino-acid, cyano, carboxylic acid or ester or thioester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino, phenylhydrazino, sulfonyl, sulfonamido and halogen, or whereby said aliphatic spacer is a methylene group containing a function, atom or radical chosen from the group consisting of carbonyl (oxo), alcohol (hydroxyl), ether, acetal, amino, imino, oximino, alkyloximino, aminoacid, cyano, carboxylic acid or ester or thioester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino, phenylhydrazino, sulfonyl, sulfonamido, fluoro and chloro; branched or straight, saturated or unsaturated aliphatic chain of 3 to 7 carbon atoms containing one or more functions selected from the group consisting of carbonyl (oxo), alcohol (hydroxyl), ether, acetal, amino, imino, oximino, alkyloximino, aminoacid, cyano, carboxylic acid ester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino, phenylhydrazino, sulfonyl, sulfonamido and halogen; hydroxyethyl; oximinoethyl; alkyloximinoethyl; and methyl or ethyl or ethenyl containing one or more functions, atoms or radicals selected from the group consisting of ether, acetal, amino, imino, amino-acid, cyano, carboxylic acid or ester or thioester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylalkyl-amino, hydroxyalkylamino, mercaptoalkylamino, heterocyclic amino, hydrazino, alkylhydrazino, phenylhydrazino, sulfonyl, sulfonamido, fluoro and chloro;

c) if one or more of $Y_1$ and $Y_2$ is sulfur and at most one of $Y_1$ and $Y_2$ is oxygen, then:

each of $R_1$ and $R_2$ is a radical independently selected from the group consisting of hydrogen; $C_{1-7}$ alkyl; $C_{2-7}$ alkenyl; aryl; alkylaryl; ω-hydroxy $C_{1-7}$ alkyl; ω-epoxy $C_{1-7}$ alkyl; ω-carboxy $C_{1-7}$ alkyl (wherein the carboxy group may be acid, ester or amide); and optionally substituted heterocyclic radicals;

each of $R_3$ and $R_4$ is an atom or radical independently selected from the group consisting of hydrogen; halogen; $C_{2-4}$ alkyl; $C_{2-7}$ alkenyl; $C_{2-7}$ alkynyl; halo $C_{1-4}$ alkyl; $C_{2-4}$ alkoxy; $C_{3-10}$ cycloalkoxy; aryloxy; arylalkyloxy; oxyheterocyclic; heterocyclic-substituted alkyloxy; thio $C_{2-7}$ alkyl; thio $C_{3-10}$ cycloalkyl; thioaryl; thioheterocyclic; arylalkylthio; heterocyclic-substituted alkylthio; hydroxylamino; acetal; formyl; cyano; carboxylic acid; carboxylic acid esters, thioesters and amides; thiocarboxylic acid; thiocarboxylic acid esters, thioesters and amides; amino; alkylamino; cycloalkylamino; alkenylamino; cycloalkenylamino; alkynylamino; arylamino; arylalkylamino; hydroxyalkylamino; mercaptoalkylamino; heterocyclic amino; heterocyclic-substituted alkylamino; oximino; alkyloximino; hydrazino; alkylhydrazino; phenylhydrazino; cysteinyl acid, esters or amides; aromatic ring substituted with one or more substituents selected from the group consisting of halogen, $C_{1-4}$ alkyl, $C_{2-7}$ alkenyl, $C_{2-7}$ alkynyl, halo $C_{1-4}$ alkyl, $C_{1-4}$ alkoxy, hydroxyl, sulfhydryl, amino, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, carboxylic acid or esters or thioesters or amides thereof, thiocarboxylic acid or esters or thioesters or amides thereof, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino and phenylhydrazino; heterocyclic substituents; aromatic or heterocyclic substituents substituted with an aliphatic spacer between the pteridine ring and the aromatic or heterocyclic substituent, whereby said aliphatic spacer is a branched or straight, saturated or unsaturated aliphatic chain of 1 to 4 carbon atoms which may contain one or more functions, atoms or radicals selected from the group consisting of carbonyl (oxo), alcohol (hydroxyl), ether, acetal, amino, imino, oximino, alkyloximino, amino-acid, cyano, carboxylic acid or ester or thioester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxyalkyl-amino, mercaptoalkylamino, heterocyclic amino, hydrazino, alkylhydrazino, phenylhydrazino, sulfonyl, sulfonamido and halogen; branched or straight, saturated or unsaturated aliphatic chain of 1 to 7 carbon atoms containing one or more functions selected from the group consisting of carbonyl (oxo), alcohol (hydroxyl), ether, acetal, amino, imino, oximino, alkyloximino, amino-acid, cyano, carboxylic acid ester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxylalkylamino, mercaptoalkylamino, heterocyclic amino, hydrazino, alkylhydrazino, phenylhydrazino, sulfonyl, sulfonamido and halogen; or $R_4$ and $R_3$ together form an aryl radical being optionally substituted with one or more substituents $R_a$ each independently selected from the group consisting of amino, alkylamino, cycloalkylamino, alkenylamino, cycloalkenylamino, alkynylamino, arylamino, arylalkylamino, hydroxyalkylamino, mercaptoalkylamino, heterocyclic amino and heterocyclic-substituted alkylamino, wherein each substituent $R_a$ may further comprise one or more functions selected from the group consisting of carbonyl, amino and carboxyl, and wherein two adjacent substituents $R_a$ may together form an heterocyclic radical; and at most one of $R_1$, $R_2$, $R_3$ and $R_4$ is hydrogen;

d) if $Y_1$ and $Y_2$ are both oxygen and none of $R_3$ and $R_4$ is hydrogen, then:

$R_2$ is a radical selected from the group consisting of $C_{1-7}$ alkyl; $C_{2-7}$ alkenyl; aryl; alkylaryl; ω-hydroxy $C_{1-7}$ alkyl; ω-epoxy $C_{1-7}$ alkyl; ω-carboxy $C_{1-7}$ alkyl (wherein the carboxy group may be acid, ester or amide); and optionally substituted heterocyclic radicals;

$R_1$ is an atom or radical independently defined as $R_2$, or is hydrogen;

$R_4$ is an atom or radical selected from the group consisting of halogen; $C_{2-7}$ alkenyl; $C_{2-7}$ alkynyl; $C_{2-7}$ haloalkyl; fluoromethyl; $C_{2-4}$ alkoxy; $C_{3-10}$ cycloalkoxy; aryloxy; arylalkyloxy; oxyheterocyclic; heterocyclic-substituted alkyloxy; thio $C_{1-7}$ alkyl; thio $C_{3-10}$ cycloalkyl; thioaryl; thioheterocyclic; arylalkylthio; heterocyclic-substituted alkylthio; hydroxylamino; acetal; carboxylic acid thioesters and amides; thiocarboxylic acid; thiocarboxylic acid esters, thioesters and amides; sulfhydryl; $C_{2-7}$ alkylamino; cycloalkylamino; alkenylamino; cycloalkenylamino; alkynylamino; arylamino; arylalkylamino; hydroxyalkylamino; mercaptoalkylamino; heterocyclic amino; heterocyclic-substituted alkylamino; hydrazino; alkylhydrazino; phenylhydrazino; cysteinyl acid, esters or amides; aromatic ring optionally substituted with one or more substituents selected from the group consisting of halogen, $C_{1-4}$ alkyl, $C_{2-7}$ alkenyl, $C_{2-7}$ alkynyl, $C_{1-4}$ haloalkyl, $C_{1-4}$ alkoxy, hydroxyl, sulfhydryl, amino, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, carboxylic acid or esters or thioesters or amides thereof, thiocarboxylic acid or esters or thioesters or amides thereof, $C_{1-7}$ alkylamino, cycloalkylamino, alkenylamino, cycloalkenylamino, alkynylamino, arylamino, arylalkylamino, hydroxylalkylamino, mercaptoalkylamino, heterocyclic amino, hydrazino, alkylhydrazino and phenylhydrazino; optionally substituted heterocyclic radicals selected from the group consisting of tetrahydrofuryl, oxabicycloheptyl, azabenzimidazolyl, azacycloheptyl, azacyclooctyl, azacyclononyl, azabicyclononyl, tetrahydropyranyl, tetrahydropyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thio-urazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl, phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolyl, dithianyl, dithienyl, dithiinyl, thienyl, indolyl, indazolyl, benzofuryl, benzothienyl, quinolyl, quinazolinyl, quinoxalinyl, carbazolyl, phenoxazinyl, phenothiazinyl, xanthenyl, purinyl, benzothienyl, naphtothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, thietyl and thietanyl; aromatic or heterocyclic substituents substituted with an aliphatic spacer between the pteridine ring and the aromatic or heterocyclic substituent, whereby said aliphatic spacer is a branched or straight, saturated or unsaturated aliphatic chain of 1 to 4 carbon atoms which may contain one or more functions, atoms or radicals selected from the group consisting of carbonyl (oxo), alcohol (hydroxyl), ether, acetal, amino, imino, oximino, alkyloximino, amino-acid, cyano, carboxylic acid or ester or thioester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino, phenylhydrazino, sulfonyl, sulfonamido and halogen; branched or straight, saturated or unsaturated aliphatic chain of 2 to 7 carbon atoms containing one or more atoms, functions or radicals selected from the group consisting of carbonyl (oxo), alcohol (hydroxyl), ether, acetal, amino, imino, oximino, alkyloximino, amino-acid, cyano, carboxylic acid ester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxyalkylamino, mercaptoalkyl-amino, heterocyclic amino, hydrazino, alkylhydrazino, phenylhydrazino, sulfonyl, sulfonamido and halogen; hydroxyethyl; and $R_3$ is an atom or radical independently defined as $R_4$, or is amino or methoxy, or $R_4$ and $R_3$ together form an aryl radical being optionally substituted with one or more substituents $R_a$ each independently selected from the group consisting of amino, alkylamino, cycloalkylamino, alkenylamino, cycloalkenylamino, alkynylamino, arylamino, arylalkylamino, hydroxyalkylamino, mercaptoalkylamino, heterocyclic amino and heterocyclic-substituted alkylamino, wherein each substituent $R_a$ may further comprise one or more functions selected from the group consisting of carbonyl, amino and carboxyl, and wherein two adjacent substituents $R_a$ may together form an heterocyclic radical;

e) if $Y_1$ and $Y_2$ are both oxygen and none of $R_3$ and $R_4$ is hydrogen, then:

$R_1$ is a radical selected from the group consisting of $C_{2-7}$ alkyl; $C_{2-7}$ alkenyl; aryl; alkylaryl; ω-hydroxy $C_{1-7}$ alkyl; ω-epoxy $C_{1-7}$ alkyl; ω-carboxy $C_{1-7}$ alkyl (wherein the carboxy group may be acid, ester or amide); and optionally substituted heterocyclic radicals;

$R_2$ is hydrogen;

$R_3$ is an atom or radical selected from the group consisting of fluoro; bromo; iodo; $C_{2-7}$ alkyl; $C_{2-7}$ alkenyl; $C_{2-7}$ alkynyl; $C_{1-7}$ haloalkyl; $C_{1-4}$ alkoxy; $C_{3-10}$ cycloalkoxy; aryloxy; arylalkyloxy; oxyheterocyclic; heterocyclic-substituted alkyloxy; thio $C_{1-7}$ alkyl; thio $C_{3-10}$ cycloalkyl; thioaryl; thioheterocyclic; arylalkylthio; heterocyclic-substituted alkylthio; hydroxylamino; acetal; carboxylic acid esters, thioesters and amides; thiocarboxylic acid; thiocarboxylic acid esters, thioesters and amides; sulfhydryl; amino; alkylamino; cycloalkylamino; alkenylamino; cycloalkenyl-amino; alkynylamino; arylamino; arylalkylamino; hydroxyalkylamino; mercaptoalkylamino; heterocyclic amino; heterocyclic-substituted alkylamino; hydrazino; alkylhydrazino; phenylhydrazino; cysteinyl acid, esters or amides; aromatic ring substituted with one or more substituents selected from the group consisting of halogen, $C_{1-4}$ alkyl, $C_{2-7}$ alkenyl, $C_{2-7}$ alkynyl, $C_{1-4}$ haloalkyl, $C_{1-4}$ alkoxy, hydroxyl, sulfhydryl, amino, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, carboxylic acid or esters or thioesters or amides thereof, thiocarboxylic acid or esters or thioesters or amides thereof, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino and phenylhydrazino; optionally substituted heterocyclic radicals; aromatic or heterocyclic substituents substituted with an aliphatic spacer between the pteridine ring and the aromatic or heterocyclic substituent, whereby said aliphatic spacer is a branched or straight, saturated or unsaturated aliphatic chain of 1 to 4 carbon atoms which may contain one or more functions, atoms or radicals selected from the group consisting of carbonyl (oxo), alcohol (hydroxyl), ether, acetal, amino, imino, oximino, alkyloximino, amino-acid, cyano, carboxylic acid or ester or thioester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino, phenylhydrazino, sulfonyl, sulfonamido and halogen; branched or straight, saturated or unsaturated aliphatic chain of 1 to 7 carbon atoms containing one or more atoms, functions or radicals selected from the group consisting of carbonyl (oxo), alcohol (hydroxyl), ether, acetal, amino, imino, oximino, alkyloximino, amino-acid, cyano, carboxylic acid ester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxylalkylamino, mercaptoalkylamino, heterocyclic amino, hydrazino, alkylhydrazino, phenylhydrazino, sulfonyl, sulfonamido and halogen; hydroxyethyl; and $R_4$ is an atom or radical independently defined as $R_3$, or is chloro, or $R_4$ and $R_3$ together form an aryl radical being optionally substituted with one or more substituents $R_a$ each independently selected from the group consisting of amino, alkylamino, cycloalkylamino, alkenylamino, cycloalkenylamino, alkynylamino, arylamino, arylalkylamino, hydroxyalkylamino, mercaptoalkylamino, heterocyclic amino and heterocyclic-substituted alkylamino, wherein each substituent $R_a$ may further comprise one or more functions selected from the group consisting of carbonyl, amino and carboxyl, and wherein two adjacent substituents $R_a$ may together form an heterocyclic radical;

f) if $Y_1$ and $Y_2$ are both oxygen and $R_2$ and $R_3$ are both hydrogen, then:

$R_1$ is a radical selected from the group consisting of $C_{1-7}$ alkyl; $C_{2-7}$ alkenyl; aryl; alkylaryl; ω-hydroxy $C_{1-7}$ alkyl; ω-epoxy $C_{1-7}$ alkyl; ω-carboxy $C_{1-7}$ alkyl (wherein the carboxy group may be acid, ester or amide); and optionally substituted heterocyclic radicals;

$R_4$ is an atom or a radical selected from the group consisting of halogen, cyano, amino, alkylamino, cycloalkylamino, alkenylamino, cycloalkenylamino, alkynylamino, arylamino, arylalkylamino, hydroxyalkylamino, mercaptoalkylamino, heterocyclic amino and heterocyclic-substituted alkylamino;

or a pharmaceutically acceptable salt or an enantiomer thereof.

For easiness of understanding the set of compounds of general formula (I) may be sub-divided into six sub-sets of compounds, depending upon (i) the nature of $Y_1$ and $Y_2$, and (ii) when $Y_1$ and $Y_2$ are both oxygen, upon the number and location of substituents on the pteridine ring. More specifically, these six sub-sets of compounds of general formula (I) are as follows:

a) trisubstituted lumazines wherein substitutions are in positions 1, 3 and 6 on the pteridine ring,
b) trisubstituted lumazines wherein substitutions are in positions 1, 3 and 7 on the pteridine ring,
c) mono- and poly-substituted 2-thiolumazines, 4-thiolumazines and 2,4-dithiolumazines,
d) tetrasubstituted lumazines,
e) trisubstituted lumazines wherein substitutions are in positions 3, 6 and 7 on the pteridine ring, and
f) disubstituted lumazines wherein substitutions are in positions 1 and 7 on the pteridine ring.

It should be noted, however, that these sub-sets of novel compounds have in common the structural features present in the general formula (I). They also have a potential specific biological activity profile and consequent usefulness in medicinal chemistry.

In a second embodiment, the present invention relates to the unexpected finding that at least one desirable biological property such as, but not limited to, the ability to decrease the proliferation of lymphocytes, or to decrease T-cell activation, or to decrease B-cell or monocytes or macrophages activation, or to inhibit TNF-α and IL-1 release, is a common feature which is not only present in the group of novel compounds defined in the general formula (I), but also in a group of polysubstituted pteridine-2,4-diones (lumazines), as well as mono- and poly-substituted 2-thiolumazines, 4-thiolumazines and 2,4-dithiolumazines which is broader than the said group of novel compounds, specifically in a group of compounds represented by the general formula (II):

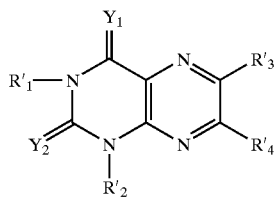

wherein:
- each of $Y_1$ and $Y_2$ is independently selected from sulfur and oxygen;
- each of $R_1$ and $R_2$ is a radical independently selected from the group consisting of hydrogen; $C_{1-7}$ alkyl; $C_{2-7}$ alkenyl; aryl; alkylaryl; ω-hydroxy $C_{1-7}$ alkyl; ω-epoxy $C_{1-7}$ alkyl; ω-carboxy $C_{1-7}$ alkyl (wherein the carboxy group may be acid, ester or amide); and optionally substituted heterocyclic radicals;
- at most one of $R_1$, $R_2$, $R_3$ and $R_4$ is hydrogen when one or more of $Y_1$ and $Y_2$ is sulfur;
- at most one of $R_1$ and $R_2$ is hydrogen when both $Y_1$ and $Y_2$ are oxygen;
- each of $R_3$ and $R_4$ is an atom or radical independently selected from the group consisting of hydrogen; halogen; $C_{1-4}$ alkyl; $C_{2-7}$ alkenyl; $C_{2-7}$ alkynyl; halo $C_{1-4}$ alkyl; $C_{1-4}$ alkoxy; $C_{3-10}$ cycloalkoxy; aryloxy; arylalkyloxy; oxyheterocyclic; heterocyclic-substituted alkyloxy; thio $C_{1-7}$ alkyl; thio $C_{3-10}$ cycloalkyl; thioaryl; thioheterocyclic; arylalkylthio; heterocyclic-substituted alkylthio; hydroxylamino; acetal; formyl; cyano; carboxylic acid; carboxylic acid esters, thioesters and amides; thiocarboxylic acid; thiocarboxylic acid esters, thioesters and amides; amino; $C_{2-7}$ alkylamino; cycloalkylamino; alkenylamino; cycloalkenylamino; alkynylamino; arylamino; arylalkylamino; hydroxyalkylamino; mercaptoalkylamino; heterocyclic amino; heterocyclic-substituted alkylamino; oximino; alkyloximino; hydrazino; alkylhydrazino; phenylhydrazino; cysteinyl acid, esters or amides; aromatic ring optionally substituted with one or more substituents selected from the group consisting of halogen, $C_{1-4}$ alkyl, $C_{2-7}$ alkenyl, $C_{2-7}$ alkynyl, halo $C_{1-4}$ alkyl, $C_{1-4}$ alkoxy, hydroxyl, sulfhydryl, amino, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, carboxylic acid or esters or thioesters or amides thereof, thiocarboxylic acid or esters or thioesters or amides thereof, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino and phenylhydrazino; heterocyclic substituents; aromatic or heterocyclic substituents substituted with an aliphatic spacer between the pteridine ring and the aromatic or heterocyclic substituent, whereby said aliphatic spacer is a branched or straight, saturated or unsaturated aliphatic chain of 1 to 4 carbon atoms which may contain one or more functions, atoms or radicals selected from the group consisting of carbonyl (oxo), alcohol (hydroxyl), ether, acetal, amino, imino, oximino, alkyloximino, amino-acid, cyano, carboxylic acid or ester or thioester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino, phenylhydrazino, sulfonyl, sulfonamido and halogen; branched or straight, saturated or unsaturated aliphatic chain of 1 to 7 carbon atoms containing one or more atoms, functions or radicals selected from the group consisting of carbonyl (oxo), alcohol (hydroxyl), ether, acetal, amino, imino, oximino, alkyloximino, amino-acid, cyano, carboxylic acid ester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino, phenylhydrazino, sulfonyl, sulfonamido and halogen, and
- $R_4$ and $R_3$ may together form an aryl radical being optionally substituted with one or more substituents $R_a$ each independently selected from the group consisting of amino, alkylamino, cycloalkylamino, alkenylamino, cycloalkenylamino, alkynylamino, arylamino, arylalkylamino, hydroxyalkylamino, mercaptoalkylamino, heterocyclic amino and heterocyclic-substituted alkylamino, wherein each substituent $R_a$ may further comprise one or more functions selected from the group consisting of carbonyl, amino and carboxyl, and wherein two adjacent substituents $R_a$ may together form an heterocyclic radical.

Compounds of formula (II) are highly active immunosuppressive agents, antineoplastic agents or anti-viral agents which, together with one or more pharmaceutically acceptable carriers, may be formulated into pharmaceutical compositions for the prevention or treatment of pathologic conditions such as, but not limited to, immune and autoimmune disorders, organ and cells transplant rejections, cell proliferative disorders, cardiovascular disorders, disorders of the central nervous system and viral diseases.

In a further embodiment, the present invention relates to combined preparations containing at least one compound of formula (II) and one or more drugs such as immunosuppressant and/or immunomodulator drugs, antineoplastic drugs, or antiviral agents. In a further embodiment, the present invention relates to the prevention or treatment of the above-cited pathologic conditions by administering to the patient in need thereof an effective amount of a compound of general formula (II), optionally in the form of a pharmaceutical composition or combined preparation with another drug.

In a still further embodiment, the present invention relates to processes and methods for making the novel polysubstituted pteridine-2,4-diones (lumazines), as well as the novel mono- and poly-substituted 2-thiolumazines, 4-thiolumazines and 2,4-dithiolumazines defined in general formula (I) and their pharmaceutically acceptable salts and enantiomers.

DEFINITIONS

Figure 1:
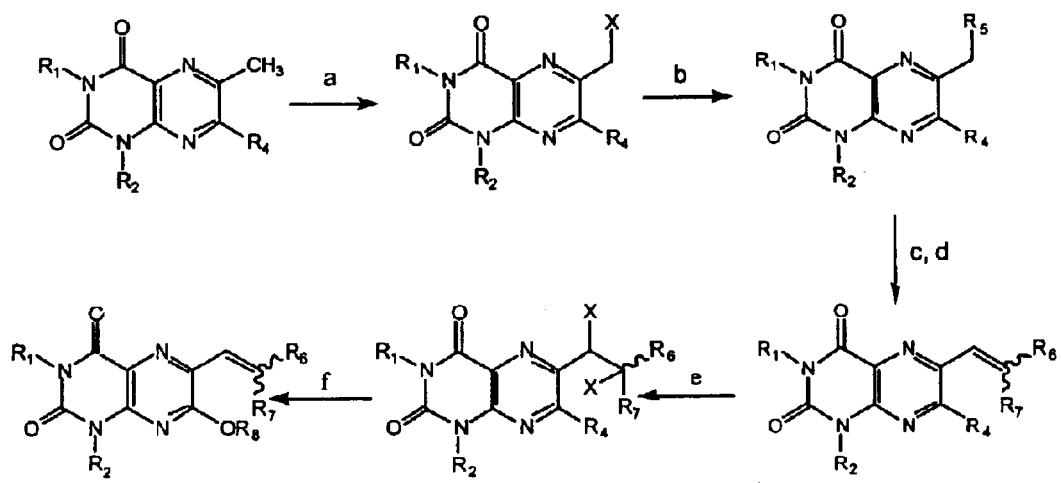
FIG. 1 represents a scheme for replacing a methyl substituent $R_3$ with an unsaturated partly aliphatic chain or spacer in the 6-position of the pteridine ring of a substituted lumazine.

As used herein, the terms "lumazine" and "pteridine-2,4-dione" are interchangeable and designate any of the tautomeric forms of 2,4-dioxopteridine or 2,4-dihydroxypteridine; the term "2-thiolumazine" designate any of the tautomeric forms of 2-thioxo-4-oxo-pteridine; the term "4-thiolumazine" designate any of the tautomeric forms of 2-oxo-4-thioxo-pteridine; the term "2,4-dithiolumazine" designate any of the tautomeric forms of 2,4-dithioxo-pteridine; the term "(thio)lumazine" is a generic abbreviation for all sub-sets of compounds designated herein-above. Unless otherwise stated herein, the term "polysubstituted" means that two, three or four of the atoms being in any of positions 1, 3, 6 and 7 (according to standard atom numbering for the pteridine ring) are substituted with an atom or group other than hydrogen. The term "monosubstituted" means that only one of the atoms being in positions 1, 3, 6 and 7 is substituted with an atom or group other than hydrogen.

As used herein and unless otherwise stated, the terms "$C_{1-7}$ alkyl" or "aliphatic saturated hydrocarbon radicals with 1 to 7 carbon atoms" means straight and branched chain saturated acyclic hydrocarbon monovalent radicals having from 1 to 7 carbon atoms such as, for example, methyl, ethyl, propyl, n-butyl, 1-methylethyl (isopropyl), 2-methylpropyl (isobutyl), 1,1-dimethylethyl (ter-butyl), 2-methylbutyl, n-pentyl, dimethylpropyl, n-hexyl, 2-methylpentyl, 3-methylpentyl, n-heptyl and the like; the term "$C_{1-4}$ alkyl" designate the corresponding radicals with only 1 to 4 carbon atoms, and so on.

As used herein and unless otherwise stated, the term $C_{1-7}$ alkylene means the divalent hydrocarbon radical corresponding to the above defined $C_{1-7}$ alkyl, such as methylene, bis(methylene), tris(methylene), tetramethylene, hexamethylene and the like.

As used herein and unless otherwise stated, the terms "$C_{3-10}$ cycloalkyl" and "cycloaliphatic saturated hydrocarbon radical with 3 to 10 carbon atoms" means a monocyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

As used herein and unless otherwise stated, the term "$C_{3-10}$ cycloalkylene" means the divalent hydrocarbon radical corresponding to the above defined $C_{3-10}$ cycloalkyl.

As used herein and unless otherwise stated, the terms "aryl" and "aromatic substituent" are interchangeable and designate any mono- or polyaromatic monovalent hydrocarbon radical having from 6 up to 30 carbon atoms such as but not limited to phenyl, naphthyl, anthracenyl, adamantyl, phenantracyl, fluoranthenyl, chrysenyl, pyrenyl, biphenylyl, terphenyl, picenyl and the like, including spiro hydrocarbon radicals and fused benzo-$C_{5-8}$ cycloalkyl radicals (the latter being as defined above) such as, for instance, indanyl, 1,2,3,4-tetrahydronaphtalenyl, fluorenyl and the like.

As used herein and unless otherwise stated, the term "heterocyclic" means a mono- or polycyclic, saturated or mono-unsaturated or polyunsaturated monovalent hydrocarbon radical having from 2 up to 15 carbon atoms and including one or more heteroatoms in a 3 to 10 membered ring (and optionally one or more heteroatoms attached to one or more carbon atoms of said ring, for instance in the form of a carbonyl or thiocarbonyl group) and/or to one or more heteroatoms of said ring, for instance in the form of a sulfone, sulfoxide, N-oxide, phosphate, phosphonate or selenium oxide, each said heteroatom being independently selected from the group consisting of nitrogen, oxygen, sulfur, selenium and phosphorus, including benzo-fused heterocyclic radicals, such as but not limited to oxabicycloheptyl, azabenzimidazolyl, azacycloheptyl, azacyclooctyl, azacyclononyl, azabicyclononyl, tetrahydrofuryl, tetrahydropyranyl, tetrahydropyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thio-urazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl, phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, quinolyl, quinazolinyl, quinoxalinyl, carbazolyl, phenoxazinyl, phenothiazinyl, xanthenyl, purinyl, benzothienyl, naphtothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrrolidinyl, piperazinyl, uridinyl, thymidinyl,cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, thietyl, thietanyl and the like, including all possible isomeric forms thereof, wherein each carbon atom of the said ring may be substituted with a substituent selected from the group consisting of halogen, nitro, $C_{1-7}$ alkyl (optionally containing one or more functions or radicals selected from the group consisting of carbonyl (oxo), alcohol (hydroxyl), ether (alkoxy), acetal, amino, imino, oximino, alkyloximino, amino-acid, cyano, carboxylic acid ester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxylalkylamino, mercapto-alkylamino, heterocyclic amino, hydrazino, alkylhydrazino, phenyl-hydrazino, sulfonyl, sulfonamido and halogen), $C_{3-7}$ alkenyl, $C_{2-7}$ alkynyl, halo $C_{1-7}$ alkyl, $C_{3-10}$ cycloalkyl, aryl, arylalkyl, alkylaryl, alkylacyl, arylacyl, hydroxyl, amino, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic amino, hydrazino, alkylhydrazino, phenylhydrazino, sulfhydryl, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, carboxylic acid or esters or thioesters or amides thereof, thiocarboxylic acid or esters or thioesters or amides thereof; depending upon the number of unsaturations in the 3 to 10 membered ring, heterocyclic radicals may be sub-divided into heteroaromatic (or "heteroaryl") radicals and non-aromatic heterocyclic radicals; when a heteroatom of the said non-aromatic heterocyclic radical is nitrogen, the latter may be substituted with a substituent selected from the group consisting of $C_{1-7}$ alkyl, $C_{3-10}$ cycloalkyl, aryl, arylalkyl, alkylaryl, alkylacyl and arylacyl.

As used herein and unless otherwise stated, the terms "$C_{1-7}$ alkoxy", "$C_{3-10}$ cycloalkoxy", "aryloxy", "arylalkyloxy", "oxyheterocyclic", "thio $C_{1-7}$ alkyl", "thio $C_{3-10}$ cycloalkyl", "arylthio", "arylalkylthio" and "thioheterocyclic" refer to substituents wherein a $C_{1-7}$ alkyl radical, respectively a $C_{3-10}$ cycloalkyl, aryl, arylalkyl or heterocyclic radical (each of them such as defined herein), are attached to an oxygen atom or a sulfur atom through a single bond, such as but not limited to methoxy, ethoxy, propoxy, butoxy, thioethyl, thiomethyl, phenyloxy, benzyloxy, mercaptobenzyl and the like.

As used herein and unless otherwise stated, the term halogen means any atom selected from the group consisting of fluorine, chlorine, bromine and iodine.

As used herein and unless otherwise stated, the term "halo $C_{1-7}$ alkyl" means a $C_{1-7}$ alkyl radical (such as above defined) in which one or more hydrogen atoms are independently replaced by one or more halogens (preferably fluorine, chlorine or bromine), such as but not limited to difluoromethyl, trifluoromethyl, trifluoroethyl, octafluoropentyl, dodecafluoroheptyl, dichloromethyl and the like; the term "halo $C_{1-4}$ alkyl" designate the corresponding radical with only 1 to 4 carbon atoms, and so on.

As used herein and unless otherwise stated, the terms "$C_{2-7}$ alkenyl" and "aliphatic unsaturated hydrocarbon radical with 2 to 7 carbon atoms" are interchangeable and designate a straight and branched acyclic hydrocarbon monovalent radical having one or more ethylenical unsaturations and having from 2 to 7 carbon atoms such as, for example, vinyl, 2-propenyl, 3-butenyl, 2-butenyl, 2-pentenyl, 3-pentenyl, 3-methyl-2-butenyl, 3-hexenyl, 2-hexenyl, 2-heptenyl, butadienyl, pentadienyl, hexadienyl, heptadienyl, heptatrienyl and the like, including all possible isomers thereof; the term "$C_{3-7}$ alkenyl" designate the corresponding radical with only 3 to 7 carbon atoms, and so on.

As used herein and unless otherwise stated, the terms "$C_{3-10}$ cycloalkenyl" or "cycloaliphatic unsaturated hydrocarbon radicals with 3 to 10 carbon atoms" means a monocyclic mono- or polyunsaturated hydrocarbon monovalent radical having from 3 to 8 carbon atoms, such as for instance cyclopropenyl, cyclobutenyl, cyclopentenyl, cyclopentadienyl, cyclohexenyl, cyclohexadienyl, cycloheptenyl, cycloheptadienyl, cycloheptatrienyl, cyclooctenyl, cyclooctadienyl and the like, or a $C_{7-10}$ polycyclic mono- or polyunsaturated hydrocarbon monovalent radical having from 7 to 10 carbon atoms such as dicyclopentadienyl, fenchenyl (including all isomers thereof, such as α-pinolenyl), bicyclo[2.2.1]hept-2-enyl, bicyclo[2.2.1]hepta-2,5-dienyl, cyclo-fenchenyl and the like.

As used herein and unless otherwise stated, the term "$C_{2-7}$ alkynyl" defines straight and branched chain hydrocarbon radicals containing one or more triple bonds and having from 2 to 20 carbon atoms such as, for example, acetylenyl, 2-propynyl, 3-butynyl, 2-butynyl, 2-pentynyl, 3-pentynyl, 3-methyl-2-butynyl, 3-hexynyl, 2-hexynyl and the like and all possible isomers thereof.

As used herein and unless otherwise stated, the terms "arylalkyl" and "heterocyclic-substituted alkyl" refer to an aliphatic saturated hydrocarbon monovalent radical, preferably a $C_{1-7}$ alkyl or a $C_{3-10}$ cycloalkyl such as defined above, onto which an aryl radical or respectively a heterocyclic radical (such as defined above) is already bonded, such as but not limited to benzyl, pyridylmethyl, pyridylethyl, 2-(2-pyridyl)isopropyl, oxazolylbutyl, 2-thienylmethyl and 2-furylmethyl.

As used herein and unless otherwise stated, the term "alkylaryl" and "alkyl-substituted heterocyclic" refer to an aryl radical or respectively a heterocyclic radical (such as defined above) onto which is (are) already bonded one or more aliphatic saturated hydrocarbon monovalent radicals, preferably $C_{1-7}$ alkyl radicals or $C_{3-10}$ cycloalkyl radicals as defined above such as, but not limited to, o-toluyl, m-toluyl, p-toluyl, mesityl and 2,4,6-trimethylphenyl.

As used herein and unless otherwise stated, the terms "alkylamino", "cycloalkylamino", "alkenylamino", "cycloalkenylamino", "arylamino", "arylalkylamino", "heterocyclic amino", "hydroxyalkylamino", "mercaptoalkylamino" and "alkynylamino" mean that one or even two $C_{1-7}$ alkyl, $C_{3-10}$ cycloalkyl, $C_{2-7}$ alkenyl, $C_{3-10}$ cycloalkenyl, aryl, arylalkyl, heterocyclic, hydroxy $C_{1-7}$ alkyl, mercapto $C_{1-7}$ alkyl or $C_{2-7}$ alkynyl radicals (each of them as defined herein, respectively) are attached to a nitrogen atom through a single bond or, in the case of heterocyclic, include a nitrogen atom, such as but not limited to, anilino, benzylamino, methylamino, dimethylamino, ethylamino, isopropylamino, propenylamino, n-butylamino, terbutylamino, dibutylamino, morpholino-alkylamino, morpholinyl, piperidinyl, piperazinyl, hydroxymethylamino and ethynylamino; this definition also includes mixed amino radicals wherein the nitrogen atom is attached to two such radicals belonging to two different sub-set of radicals, e.g. an alkyl radical and an alkenyl radical.

As used herein and unless otherwise stated, the terms "(thio)carboxylic acid ester", "(thio)carboxylic acid thioester" and "(thio)carboxylic acid amide" refer to radicals wherein the carboxyl or thiocarboxyl group is directly attached to the pteridine ring (e.g. in the 6- and/or 7-position) and wherein said carboxyl or thiocarboxyl group is bonded to the hydrocarbonyl residue of an alcohol, a thiol, a polyol, a phenol, a thiophenol, a primary or secondary amine, a polyamine, an amino-alcohol or ammonia, the said hydrocarbonyl residue being selected from the group consisting of alkyl, alkenyl, alkynyl, cycloalkyl, cycloalkenyl, aryl, arylalkyl, alkylaryl, alkylamino, cycloalkylamino, alkenylamino, cycloalkenylamino, arylamino, arylalkylamino, heterocyclic amino, hydroxyalkylamino, mercaptoalkylamino or alkynylamino (such as above defined, respectively).

As used herein and unless otherwise stated, the term "amino-acid" refers to a radical derived from a molecule having the chemical formula $H_2N-CHR-COOH$, wherein R is the side group of atoms characterizing the amino-acid type; said molecule may be one of the 20 naturally-occurring amino-acids or any non naturally-occurring amino-acid.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

DETAILED DESCRIPTION OF THE INVENTION

In the first embodiment of the invention, the novel polysubstituted pteridine-2,4-diones (lumazines), as well as the novel mono- and poly-substituted 2-thiolumazines, 4-thiolumazines and 2,4-dithiolumazines are as defined in the general formula (I), wherein each of the substituents $Y_1$, $Y_2$, $R_1$, $R_2$, $R_3$ and $R_4$ may correspond to any of the definitions given herein, in particular with any of the individual meanings (such as illustrated above) of generic terms such as but not limited to "$C_{1-7}$ alkyl", "$C_{2-7}$ alkenyl", "$C_{2-7}$ alkynyl", "aryl", "alkylaryl", "arylalkyl", "alkylamino", "cycloalkylamino", "alkenylamino", "alkynylamino", "arylamino", "arylalkylamino", "$C_{1-7}$ alkoxy", "$C_{3-10}$ cycloalkoxy", "thio $C_{1-7}$ alkyl", "thio $C_{3-10}$ cycloalkyl", "halo $C_{1-7}$ alkyl", "amino-acid" and the like.

When a mixture of enantiomers of the pteridinediones (lumazines), 2-thiolumazines, 4-thiolumazines or 2,4-dithiolumazines having the general formula (I) according to the invention is obtained during their synthesis, the said mixture may be separated by means and methods standard in the art, e.g. liquid chromatography using one or more suitable chiral stationary phases. The latter include, for example, polysaccharides, in particular cellulose or amylose derivatives. Commercially available polysaccharide based chiral stationary phases are ChiralCel™ CA, OA, OB, OC, OD, OF, OG, OJ and OK, and Chiralpak™ AD, AS, OP(+) and OT(+). Appropriate eluents or mobile phases for use in combination with said polysaccharide chiral stationary phases are hydrocarbons such as hexane and the like, optionally admixed with an alcohol such as ethanol, isopropanol and the like. The above mixture of enantiomers may alternatively be separated by forming diastereoisomers, followed by separation of the diastereoisomers, e.g. by differential crystallization or chromatography. The resolving agent may be cleaved from the separated diastereoisomers, e.g. by treatment with acids or bases, to generate the pure enantiomers of the compounds of the invention.

Some preferred polysubstituted pteridine-2,4-diones (lumazines), as well as mono- and polysubstituted 2-thiolumazines, 4-thiolumazines and 2,4-dithiolumazines having the general formula (I) according to the invention are more specifically illustrated in the following examples and defined in the following claims. For instance, useful species include those wherein:

$R_1$ and $R_2$ are each methyl, and/or
$R_4$ is chloro or $R_4$ is hydrogen, and/or
$R_3$ is cyano or $R_3$ is phenyl or $R_3$ is alkyl carboxylate.

The present invention further provides processes and methods for making the novel polysubstituted pteridine-2, 4-diones (lumazines), as well as the novel mono- and polysubstituted 2-thiolumazines, 4-thiolumazines and 2,4-dithiolumazines having the general formula (I). As a general rule, the preparation of these (thio)lumazines is based on the principle that, starting from a lumazine or (di)thiolumazine or a lumazine or (di)thiolumazine precursor, e.g. an adequately substituted uracil or thiouracil, each of the substituents $R_1$, $R_2$, $R_3$ and $R_4$ may be introduced separately without adversely influencing the presence of a substituent already introduced or the capacity to introduce further substituents later on. Therefore a process for making a (thio)lumazine having the general formula (I) usually consists of one (e.g. in the case of mono-substituted thiolumazines) or more (in the case of polysubstituted lumazines and thiolumazines) reaction steps for successively introducing one or more of the substituents $R_1$, $R_2$, $R_3$ and $R_4$ into a compound selected from the group consisting of lumazine, 2-thiolumazine, 4-thiolumazine, 2,4-dithiolumazine and known substituted (thio)lumazines, or starting from suitable (thio)lumazine precursors (such as uracils and thiouracils) already bearing the desired substituents, each reaction step being optionally, if needed, sub-divided into one or more sub-steps involving intermediate substituted (thio)lumazines.

A limited number of methods are already known in the art for introducing a substituent $R_1$, $R_2$, $R_3$ or $R_4$ to form a (substituted) lumazine or a substituted (thio)lumazine precursor, and a still more limited number of methods are known in the art for introducing a substituent $R_1$, $R_2$, $R_3$ or $R_4$ into a 2-thiolumazine, 4-thiolumazine or 2,4-dithiolumazine, all of these methods being disclosed in the prior documents referred to in the background of the invention. These methods may be applied successfully to the preparation of compounds having the general formula (I). Other methods have been developed by the present inventors, which may be used alternatively or may be combined with the former methods (depending upon the targeted final compound) and will now be explained by reference to the appended FIGS. 1 to 7 relating to substituted lumazines wherein, unless otherwise stated hereinafter, $R_1$, $R_2$, $R_3$ or $R_4$ are as defined in the summary of the invention. The same methods may be applied starting from the few substituted thiolumazines or dithiolumazines which are already known in the art. In the description of the reaction steps involved in each figure, reference may be made to the use of certain catalysts and/or certain types of solvents. It should be understood that each catalyst mentioned should be used in a catalytic amount well known to the skilled person with respect to the type of reaction involved. Solvents that may be used in the following reaction steps include various kinds of organic solvents such as protic solvents, polar aprotic solvents and non-polar solvents as well as aqueous solvents which are inert under the relevant reaction conditions. More specific examples include aromatic hydrocarbons, chlorinated hydrocarbons, ethers, aliphatic hydrocarbons, alcohols, esters, ketones, amides, water or mixtures thereof, as well as supercritical solvents such as carbon dioxide (while performing the reaction under supercritical conditions). The suitable reaction temperature and pressure conditions applicable to each kind of reaction step will not be detailed herein but do not depart from the relevant conditions already known to the skilled person with respect to the type of reaction involved.

FIG. 1 represents a scheme for (i) replacing a methyl substituent $R_3$ with an unsaturated partly aliphatic chain or spacer in the 6-position of the pteridine ring and optionally further (ii) inserting an oxygen atom between the $R_4$ substituent and the pteridine ring in the 7-position thereof.

The $R_3$ substituent replacement occurs via a succession of reaction steps as follows. In reaction step (a), a 6-methyl substituted lumazine is reacted:

- either with an halogen, preferably chlorine or bromine, in the presence of a protic solvent, or
- with an N-halosuccinimide in the presence of a protic or aprotic solvent.

Then in reaction step (b), the reaction product of step (a) is reacted, in the presence of a non-polar solvent, preferably toluene, xylene or nitro-methane, with a phosphine selected from the group consisting of trialkylphosphines (alkyl$_3$P), triarylphosphines (aryl$_3$P), tricycloalkylphosphines (cylcoalkyl$_3$P) and trialkylphosphites (alkoxy$_3$P), or the corresponding arsines, thus resulting in an intermediate compound wherein $R_5$ is selected from the group consisting of (aryl)$_3$P$^+$X$^-$, (alkyl)$_3$ P$^+$X$^-$, (cycloalkyl)$_3$ P$^+$X$^-$, (alkyloxy)$_2$PO, (aryl)$_3$ As$^+$X$^-$, (alkyl)$_3$ As$^+$X$^-$ and (cycloalkyl)$_3$ As$^+$X$^-$.

Then in the combined reaction steps (c) and (d), this intermediate compound is reacted, in the presence of a catalyst, with alkyl- or aryl- or alkylaryl- or heterocyclic- or alkoxycarbonyl-aldehyde or ketone. Suitable aliphatic, aromatic or heteroaromatic aldehydes and ketones include (in the following non-exhaustive list, use of the plural is meant to include all possible isomers) benzaldehyde, mono- and polyhalogenated benzaldehydes, cyano-benzaldehydes, substituted or non-substituted amino-benzaldehydes, mono- and dinitrobenzaldehydes, mono- and polyalkoxybenzaldehydes, mono- and polyalkylated benzaldehydes, carboxylated (esters and amides) benzaldehydes, aryloxybenzaldehydes, 2-fluorene-carboxaldehyde, naphthaldehydes, alkoxynaphthaldehydes, N-ethyl-3-carbazole-carboxaldehyde, 4-formylcinnamic acid, alkylthiobenzaldehydes, 2-formylbenzenesulfonic acid, methylformylbenzoate, acetaminobenzaldehyde, aryloxyalkylbenzaldehydes, acetamidobenzaldehyde, alkylsulfonylbenzaldehyde, propionaldehyde, butyraldehyde and the corresponding ketones. The catalyst used in the combined reaction steps (c) and (d) may be selected from the group consisting of alkoxy-alkaline metals (e.g. wherein the metal is Li, Na or K), DBU (1,8-diazabicyclo[5.4.0]undec-7-ene), DBN (1,5-diazabicyclo[4.3.0]non-5-ene), guanidine and strong bases such as butyllithium. The combined reaction steps (c) and (d) result in a compound wherein $R_6$ is selected from the group consisting of alkyl, aryl, alkylaryl, heterocyclic and alkoxycarbonyl and wherein, depending on whether an aldehyde or a ketone was reacted, $R_7$ is selected from the group consisting of hydrogen, alkyl and aryl.

Then in reaction step (e), this compound is reacted with an halogen, preferably chlorine or bromine, in the presence of a chlorinated solvent such as carbon tetrachloride or chloroform. Finally in reaction step (f), the replacement of the $R_4$ substituent is performed by reacting the product from step (e) with an alkoxy-alkaline metal (e.g. wherein the metal is Li, Na or K), thus resulting in a compound wherein $R_8$ is alkyl.

Figure 2:
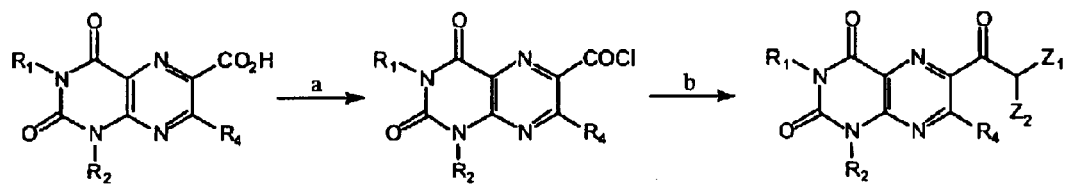
FIG. 2 represents a scheme for replacing a carboxylic substituent $R_3$ in a substituted lumazine.

FIG. 2 represents a scheme for replacing a carboxylic substituent $R_3$ in a substituted lumazine with a group having the formula COCHZ$_1$Z$_2$, wherein each of $Z_1$ and $Z_2$ may be independently selected from the group consisting of alkylcarbonyl, arylcarbonyl, alkoxycarbonyl, aryloxycarbonyl and cyano. In a first reaction step (a), a 6-carboxylic acid substituted lumazine is reacted with:

- either a compound selected from the group consisting of SOX$_2$, (COX)$_2$, PX$_3$ and PX$_5$ (preferably wherein X is Cl or Br) in the presence of a solvent,
- or triphenylphosphine in the presence of carbon tetrachloride.

In a second reaction step (b), the halocarbonyl product from step (a) is reacted with a methylene $Z_1Z_2$ ethoxy-magnesium salt or alkaline metal salt (preferably wherein the metal is Na, K or Li) in the presence of an aprotic solvent.

Figure 3:
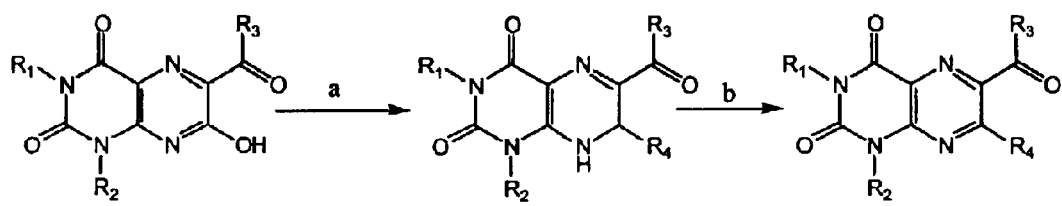
FIG. 3 represents a scheme for replacing a hydroxyl group with an aryl substituent $R_4$ in the 7-position of the pteridine ring of a substituted lumazine.

FIG. 3 represents a scheme for replacing a hydroxyl group with an aryl substituent $R_4$ in the 7-position of the pteridine ring of a substituted lumazine. In a first reaction step (a), a 7-hydroxyl, 6-carboxyaryl substituted lumazine is reacted with an aromatic hydrocarbon in the presence of a catalyst such as aluminum trichloride and a chlorinated solvent, then in a second step (b) the product of step (a) is reacted with KMnO$_4$ in the presence of a solvent such as dioxane.

Figure 4:
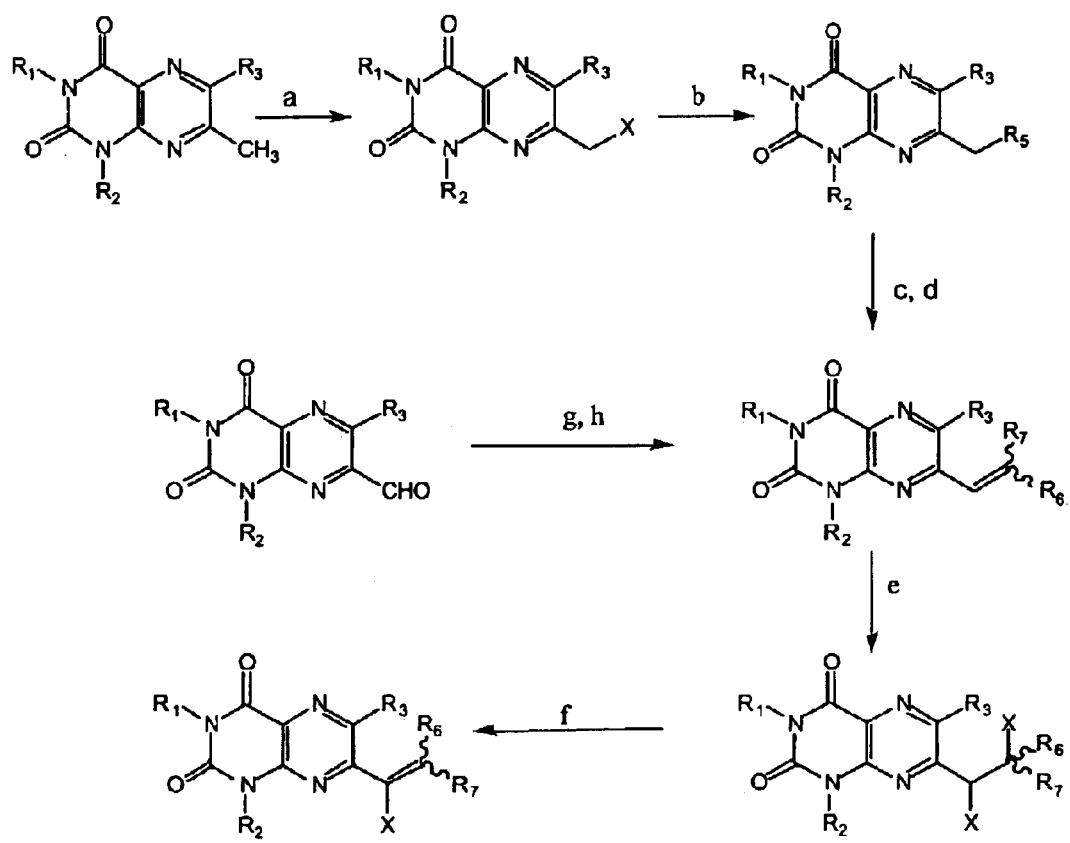
FIG. 4 represents a scheme for performing various alterations of a substituent $R_4$ on a substituted lumazine wherein the said $R_4$ is either methyl or formyl.

FIG. 4 represents a scheme for performing various alterations of a substituent $R_4$ starting from a known substituted lumazine wherein the said $R_4$ is either methyl or formyl. In reaction step (a), a 7-methyl substituted lumazine is reacted:

- either with an halogen, preferably chlorine or bromine, in the presence of a protic solvent, or
- with an N-halosuccinimide in the presence of a protic or aprotic solvent.

Then in reaction step (b), the reaction product of step (a) is reacted, in the presence of a non-polar solvent, preferably toluene, xylene or nitro-methane, with a phosphine selected from the group consisting of trialkylphosphines (alkyl$_3$P), triarylphosphines (aryl$_3$P), tricycloalkyl-phosphines (cylcoalkyl$_3$P) and trialkoxyphosphines (alkoxy$_3$P), or the corresponding arsines, thus resulting in an intermediate compound wherein $R_5$ is selected from the group consisting of (aryl)$_3$ P$^+$X$^-$, (alkyl)$_3$ P$^+$X$^-$, (cycloalkyl)$_3$ P$^+$X$^-$, (alkyloxy)$_2$PO, (aryl)$_3$ As$^+$X$^-$, (alkyl)$_3$ As$^+$X$^-$ and (cycloalkyl)$_3$As$^+$X$^-$.

Then in the combined reaction steps (c) and (d), this intermediate compound is reacted, in the presence of a catalyst, with an alkyl- or aryl- or alkylaryl- or heterocyclic- or alkoxycarbonyl-aldehyde or ketone which, alike the catalyst, may be as defined herein-above with reference to the description of FIG. 1. The combined reaction steps (c) and (d) result in a compound wherein $R_6$ is selected from the group consisting of alkyl, aryl, alkylaryl, heterocyclic and alkoxycarbonyl and wherein, depending on whether an aldehyde or a ketone was reacted, $R_7$ is selected from the group consisting of hydrogen, alkyl and aryl. This same compound may also be prepared from a 7-formyl substituted lumazine is through the combined reaction steps (g) and (h), using first an alkyl-, alkylaryl-, alkylheterocyclic-, alkoxycarbonylalkyl-, aryloxycarbonylalkyl-$R_9$ wherein $R_9$ is selected from the group consisting of triphenylphosphonium halides, trialkyl-phosphonium halides, tricycloalkylphosphonium halides or alkyl-phosphonates, and secondly a catalyst which may be selected from the group consisting of alkoxy-alkaline metals (e.g. wherein the metal is Li, Na or K), DBU, DBN and guanidine.

Then in reaction step (e), this compound is reacted with an halogen, preferably chlorine or bromine, in the presence of a chlorinated solvent such as carbon tetrachloride or chloroform. Finally in reaction step (f), the product of step (e) is reacted with a catalyst which may be selected from the group consisting of alkoxy-alkaline metals (e.g. wherein the metal is Li, Na or K), DBU, DBN and guanidine.

Figure 5:
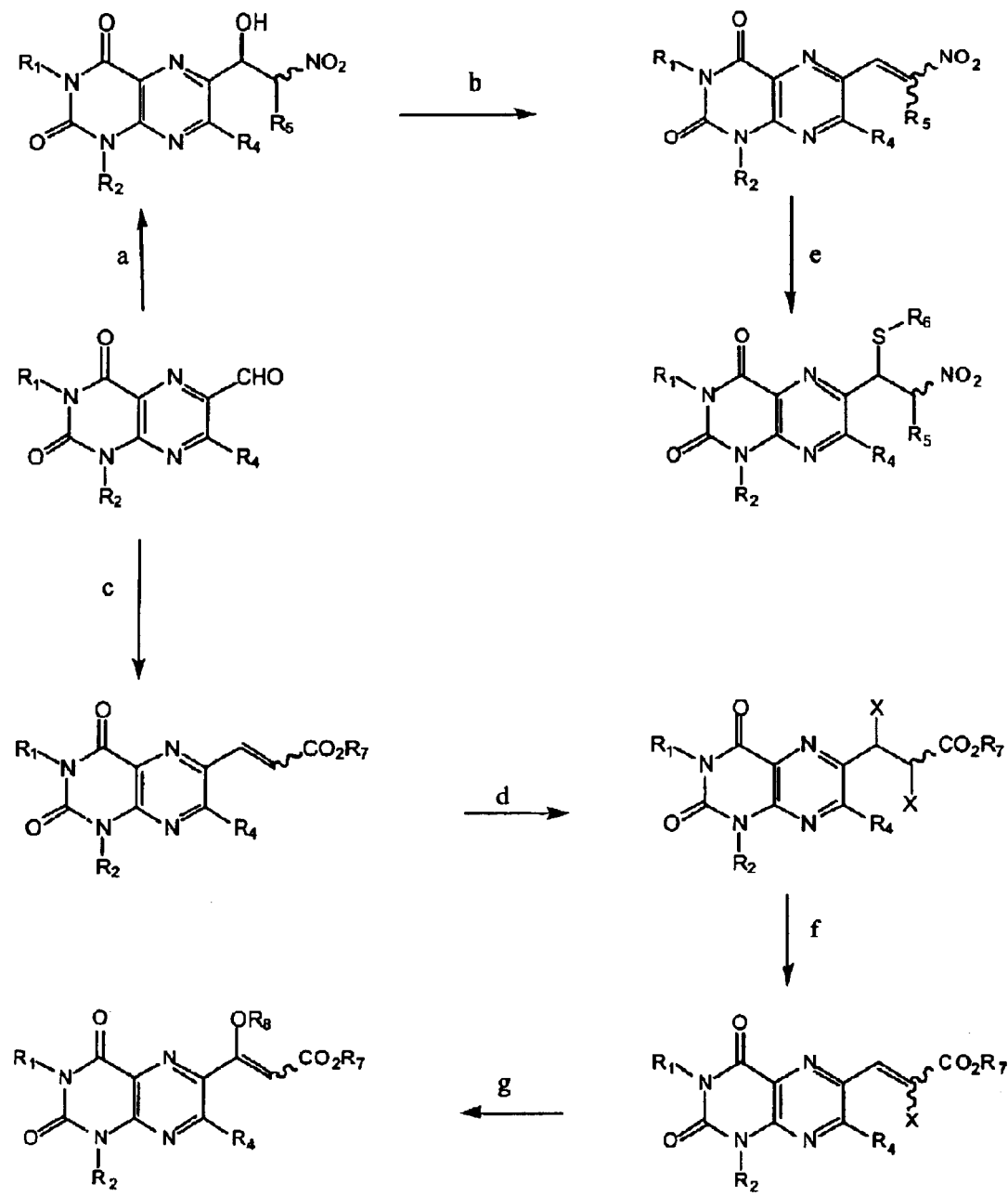
FIG. 5 represents a scheme for performing various alterations of a substituent $R_3$ starting from a substituted 6-formyllumazine.

FIG. 5 represents a scheme for performing various alterations of a substituent $R_3$ starting from a known substituted lumazine wherein the said $R_3$ is either formyl. In reaction step (a), a 6-formyl substituted lumazine is reacted with a compound having the formula $R_5CH_2NO_2$ in the presence of a base (such as a tertiary amine) and a protic or aprotic solvent. Then in step (b), the product of step (a) may be reacted with acetic anhydride in the presence of pyridine and a base in an aprotic solvent. Then in step (e), the product of step (b) may be reacted with hydrogen sulfide or a thiol $R_6SH$ wherein $R_6$ may be alkyl or aryl in a protic solvent. Alternatively in step (c), the starting 6-formyl substituted lumazine is reacted with a compound selected from the group consisting of $R_7$-oxycarbonyl-methyltriphenylphosphonium halides, $R_7$-oxycarbonyl-methyltrialkyl-phosphonium halides, $R_7$oxycarbonylmethylalkyl-phosphonates and the corresponding arsenium compounds in the presence of a base. Then in step (d), the product of step (c) may be reacted with an halogen, preferably chlorine or bromine, or an N-halosuccinimide in the presence of a protic solvent. Then in step (f), the product of step (d) may be reacted with a catalyst such as DBU, DBN or guanidine in an aprotic solvent in order to produce one or more halogenated isomers wherein the halogen atom X may be on one or the other side of the double bond. Then in step (g), the product of step (f) may be reacted with a compound having the formula $R_8OM$ (wherein M is a metal such as Na, K or Li and $R_8$ may be an alkoxy, alkoxylaryl or alkoxyheterocyclic radical).

Figure 6:
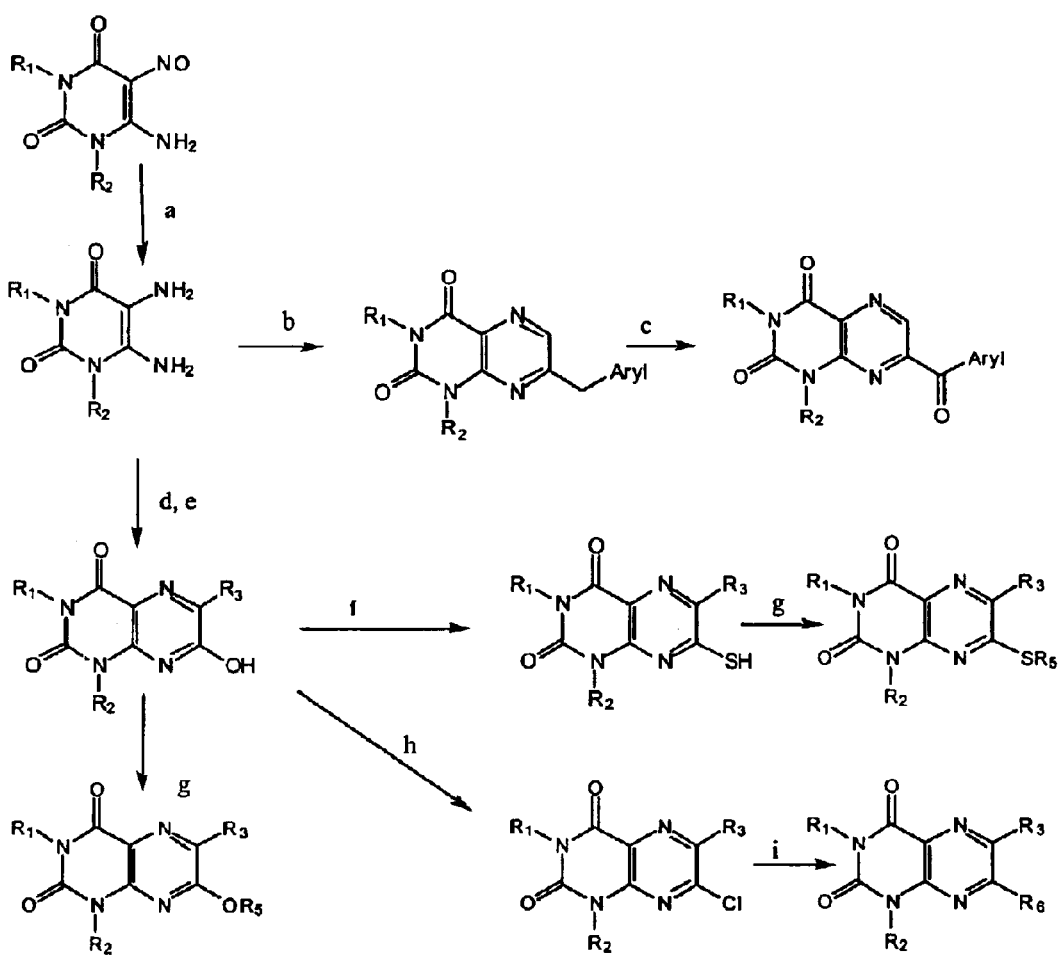
FIG. 6 represents a scheme for preparing a substituted lumazine wherein the substituent $R_4$ is either alkylaryl or hydroxyl and then performing various alterations thereon.

FIG. 6 represents a scheme for preparing a substituted lumazine wherein the said $R_4$ is either arylalkyl or hydroxyl and performing various alterations of a substituent $R_4$ starting from the said 7-hydroxyl substituted lumazine. In step (a), a 6-amino-5-nitroso-pyrimidin-2,4-dione being optionally substituted in the 1-position (with substituent $R_2$) and/or in the 3-position (with substituent $R_1$) is reacted with:

either hydrogen in the presence of a hydrogenation catalyst (such as $PtO_2$) in the presence of a protic solvent,
or sodium dithionite in the presence of water, in order to obtain an optionally substituted 5,6-diamino-uracil.

In step (b), the said optionally substituted 5,6-diamino-uracil is reacted with an arylmethylglyoxal in the presence of a protic solvent in order to obtain a 7-arylmethyl lumazine being optionally further substituted in positions 1 and/or 3. In step (c), the latter is further modified into the corresponding 7-acyl lumazine (e.g. a 7-benzoyllumazine) through an oxidation reaction by means of $KMnO_4$ in the presence of water.

Alternatively, the optionally substituted 5,6-diamino-uracil from step (a) is transformed into a 7-hydroxy lumazine being substituted in the 6-position with substituent $R_3$ through the combined steps (d) and (e) of:

reaction with an alkyl arylglyoxylate or alkyl alkylglyoxylate or alkyl heterocyclic glyoxylate or alkyl arylalkylglyoxylate or alkyl heterocyclic alkylglyoxylate in the presence of a protic solvent, and
acidification by means of an acid (e.g. nitric, sulfuric, chlorhydric acids and the like) in the presence of water.

The hydroxyl substituent of the lumazine from step (e) may then be replaced by a thiol, mercapto, alkoxy, chloro or amino substituent by any of steps (f), (g), (h) and (I) or any combination of such steps. For instance, in step (f) the lumazine from step (e) is reacted with $P_4S_{10}$ in the presence of pyridine. In step (f) the lumazine from step (e) or thiol analogue from step (f) is reacted with either a dialkylsulfate or a compound having the formula $XR_5$ wherein X may be halogen, tosyl, mesyl and the like, and $R_5$ may be alkyl, arylalkyl, heterocycloalkyl, alkoxycarbonylalkyl or aryloxycarbonyl-alkyl. In step (h), the lumazine from step (e) is reacted with $POCl_3$ in the presence of ammonium chloride. In step (i) the 7-chloro lumazine from step (h) is reacted, in the presence of an aprotic solvent, with an amine, alcohol, phenol, thiol or thiophenol having the formula $HR_6$ (wherein $R_6$ may be selected from the group consisting of amino, alkylamino, cycloalkylamino, arylamino, heterocycloalkylamino, alkoxy, aryloxy, alkylaryloxy, arylalkyloxy, heterocycloalkyloxy, thio, alkylthio, arylthio, arylalkylthio, alkylarylthio, heterocycloalkylthio) in the further presence of CsF and a catalyst such as a crown ether (e.g. 18-crown-6).

Figure 7:
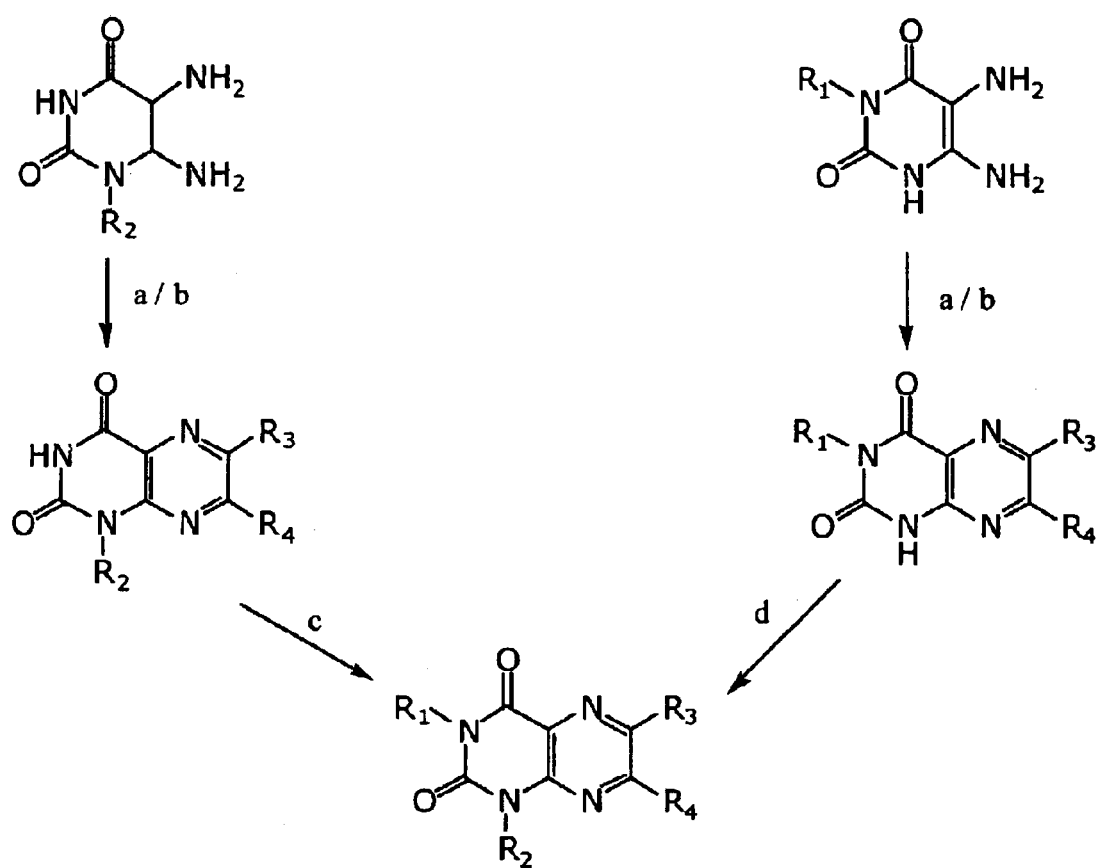
FIG. 7 represents a scheme for successively introducing substituent $R_2$ and $R_1$ substituents into a poly-substituted lumazine.

FIG. 7 represents a general scheme for preparing first a poly-substituted lumazine bearing either a multiplet of substituents ($R_1$, $R_3$, $R_4$) or a multiplet of substituents ($R_2$, $R_3$, $R_4$) and then introducing a further substituent ($R_2$ or $R_1$ respectively) into the compound of the first step. The first step consists of two sub-steps (a, b) which may be performed either simultaneously or subsequently. In the first sub-step (a), an uracil bearing a substituent $R_2$ or $R_1$, wherein $R_1$ and $R_2$ may be selected from the group consisting of hydrogen, alkyl, cycloalkyl, arylalkyl and heterocycloalkyl, is reacted in a protic solvent with a reactant bearing atoms or groups $R_3$ and $R_4$, wherein $R_3$, $R_4$ may be selected from the group consisting of hydrogen, hydroxyl, alkyl, cycloalkyl, aryl, arylalkyl, alkylaryl and heterocyclic, and wherein the said reactant may be selected from the group consisting of:

alkyl arylglyoxylates, alkyl alkylglyoxylates, alkyl heterocyclic glyoxylates, alkyl arylalkylglyoxylates, and alkyl heterocyclic alkylglyoxylates, in which case $R_4$ is hydroxyl;

alkylglyoxals, arylglyoxals, alkylarylglyoxals, arylalkylglyoxals, heterocyclic glyoxals, and the monoximes corresponding to the said glyoxals, in which case one of $R_3$ and $R_4$ is hydrogen; and dialkylethylenediones, alkyl arylethylenediones, diarylethylenediones, alkyl heterocyclic ethylenediones and diheterocyclic ethylenediones, in which case $R_3$ and $R_4$ are both different from hydrogen and hydroxyl.

In the second sub-step (b), reaction is completed by acidification of the reaction mixture.

After the first step (a, b) is completed, the resulting poly-substituted lumazine bearing either a multiplet of substituents ($R_1$, $R_3$, $R_4$) or a multiplet of substituents ($R_2$, $R_3$, $R_4$) is reacted, through step (c) or step (d) respectively, in the presence of a base and a polar aprotic solvent or a protic solvent, with a reactant $R_2X$ or $R_1X$ respectively (wherein $R_1$ and $R_2$ may each be selected from the group consisting of alkyl, cycloalkyl, arylalkyl and heterocycloalkyl, and X may be selected from the group consisting of chloro, bromo, iodo, tosylate, mesylate and the like).

When $R_4$ and $R_3$ together form an optionally substituted aryl radical, this is achieved by aromatic cyclization techniques well known in the art.

When applicable, and depending upon the specific substituents being present, not only the novel poly-substituted pteridine-2,4-diones (lumazines), and mono- and polysubstituted 2-thiolumazines, 4-thiolumazines and 2,4-dithiolumazines having the general formula (I) but also the (thio)lumazines previously known in the art without any indication of biological activity, i.e. all of the (thio) lumazines having the general formula (II) according to this invention, may be in the form of a pharmaceutically acceptable salt. The latter include any therapeutically active non-toxic addition salts which compounds having the general formula (II) are able to form with a salt-forming agent. Such addition salts may conveniently be obtained by treating the (thio)lumazine compounds (II) of the invention with an appropriate salt-forming acid or base. Examples of such appropriate salt-forming acids include, for instance, inorganic acids resulting in forming salts such as but not limited to the hydrochloride, hydrobromide, sulfate, nitrate, phosphate, diphosphate, bicarbonate, carbonate, and the like, of (thio)lumazine compounds having the general formula (II); or organic monocarboxylic or dicarboxylic acids resulting in forming salts such as, for example, the acetate, propanoate, hydroxyacetate, 2-hydroxypropanoate, 2-oxopropanoate, lactate, pyruvate, oxalate, malonate, succinate, maleate, fumarate, malate, tartrate, citrate, methanesulfonate, ethanesulfonate, benzoate, benzenesulfonate, p-toluene-sulfonate, salicylate, p-aminosalicylate, pamoate, bitartrate, camphorsulfonate, edetate, 1,2-ethanedisulfonate, fumarate, glucoheptonate, gluconate, glutamate, hexylresorcinate, hydroxynaphtoate, hydroxyethanesulfonate, lactate, mandelate, methylsulfate, pantothenate, stearate and the like, of (thio)lumazine compounds having the general formula (II). Examples of appropriate salt-forming bases include, for instance, inorganic bases like metallic hydroxides such as but not limited to those of calcium, lithium, magnesium, potassium, sodium and zinc, resulting in the corresponding metal salt of the (thio)lumazine compounds having the general formula (II); organic bases such as but not limited to N,N'-dibenzylethylenediamine, chloroprocaine, choline, diethanolamine, ethylene-diamine, N-methylglucamine, procaine and the like.

Reaction conditions for treating the (thio)lumazine compounds (II) of this invention with an appropriate salt-forming acid or base are similar to standard conditions involving the same acid or base but different compounds to be submitted to salification. Preferably the pharmaceutically acceptable salt will be selected so as to impart greater water-solubility, lower toxicity, greater stability and/or slower dissolution rate to the compounds of this invention. The term "pharmaceutically acceptable salt" as used herein also includes any solvate which may be formed with a suitable inorganic solvent (e.g. hydrates) or organic solvent, such as but not limited to alcohols, ketones, esters and the like.

The present invention further provides the use of a poly-substituted pteridinedione (lumazine), as well as a mono- or poly-substituted 2-thiolumazine, 4-thiolumazine or 2,4-dithiolumazine represented by the general formula (II), or a pharmaceutically acceptable salt thereof, as a biologically-active ingredient, especially as a medicine or a diagnostic agent or for the manufacture of a medicament or a diagnostic kit. In particular the said medicament may be for the prevention or treatment of a pathologic condition selected from the group consisting of:

immune disorders, in particular organ and cells transplant rejections, and autoimmune disorders,
cardiovascular disorders,
disorders of the central nervous system, and
cell proliferative disorders.

The pathologic conditions and disorders concerned by the said use, and the corresponding methods of prevention or treatment, are detailed hereinbelow. Any of the uses mentioned with respect to the present invention may be restricted to a non-medical use (e.g. in a cosmetic composition), a non-therapeutic use, a non-diagnostic use, a non-human use (e.g. in a veterinary composition), or exclusively an in-vitro use, or a use with cells remote from an animal.

The invention further relates to a pharmaceutical composition comprising:
(a) one or more tri- or tetra-substituted pteridinediones (lumazines), 2-thiolumazines, 4-thiolumazines or 2,4-dithiolumazines represented by the general formula (II), and
(b) one or more pharmaceutically acceptable carriers.

In a third embodiment, this invention provides combinations, preferably synergistic combinations, of one or more tri- or tetra-substituted pteridinediones (lumazines), 2-thiolumazines, 4-thiolumazines or 2,4-dithiolumazines represented by the general formula (II) with one or more biologically-active drugs being preferably selected from the group consisting of immunosuppressant and/or immunomodulator drugs, antineoplastic drugs, and antiviral agents. As is conventional in the art, the evaluation of a synergistic effect in a drug combination may be made by analyzing the quantification of the interactions between individual drugs, using the median effect principle described by Chou et al. in *Adv. Enzyme Reg.* (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively. As will be explained in more detail herein-below, this principle may be applied to a number of desirable effects such as, but not limited to, an activity against transplant rejection, an activity against immunosuppression or immunomodulation, or an activity against cell proliferation.

For instance the present invention relates to a pharmaceutical composition or combined preparation having synergistic effects against immunosuppression or immunomodulation and containing:
(a) one or more immunosuppressant and/or immunomodulator drugs, and
(b) at least one poly-substituted pteridinedione (lumazine), or mono- or poly-substituted 2-thiolumazine, 4-thiolumazine or 2,4-dithiolumazine represented by the general formula (II), and
(c) optionally one or more pharmaceutical excipients or pharmaceutically acceptable carriers,
for simultaneous, separate or sequential use in the treatment or prevention of autoimmune disorders and/or in transplant-rejections.

Suitable immunosuppressant drugs for inclusion in the synergistic compositions or combined preparations of this invention are preferably selected from the group consisting of cyclosporin A, substituted xanthines (e.g. methylxanthines such as pentoxyfylline), tacrolimus, rapamycin (and derivatives thereof), leflunomide (or its main active metabolite A771726, or analogs thereof called malononitrilamides), mycophenolic acid and salts thereof (including the sodium salt marketed under the trade name Mofetil®), adrenocortical steroids, azathioprine, brequinar, gusperimus, 6-mercaptopurine, mizoribine, chloroquine, hydroxychloroquine and monoclonal antibodies with immunosuppressive properties. Adrenocortical steroids within the meaning of this invention mainly include glucocorticoids such as but not limited to dexamethasone, methylprednisolone, methotrexate, prednisone, prednisolone, triamcinolone and pharmaceutically acceptable salts thereof. Rapamycin derivatives as referred herein include O-alkylated derivatives, particularly 9-deoxorapamycins, 26-dihydrorapamycins, 40-O-substituted rapamycins and 28,40-O,O-disubstituted rapamycins (as disclosed in U.S. Pat. No. 5,665,772) such as 40-O-(2-hydroxy) ethyl rapamycin—also known as SDZ-RAD—, pegylated rapamycin (as disclosed in U.S. Pat. No. 5,780,462), ethers of 7-desmethylrapamycin (as disclosed in U.S. Pat. No. 6,440,991) and polyethylene glycol esters of SDZ-RAD (as disclosed in U.S. Pat. No. 6,331,547).

Suitable immunomodulator drugs for inclusion into the synergistic immunomodulating pharmaceutical compositions or combined preparations of this invention are preferably selected from the group consisting of acemannan, amiprilose, bucillamine, ditiocarb sodium, imiquimod, Inosine Pranobex, interferon-β, interferon-γ, lentinan, levamisole, pidotimod, romurtide, platonin, procodazole, propagermanium, thymomodulin, thymopentin and ubenimex.

Synergistic activity of the pharmaceutical compositions or combined preparations of this invention against immunosuppression or immunomodulation may be readily determined by means of one or more tests such as, but not limited to, the MLR (abbreviation standing for "mixed lymphocyte reaction") test, or a test wherein TNF-α or IL-1β inhibition and/or a test wherein the activation of a cluster of differentiation (hereinafter referred as CD) is quantified. The synergistic effect may be evaluated by the median effect analysis method described herein-before. Such tests may for instance, according to standard practice in the art, involve the use of equiment, such as flow cytometer, being able to separate and sort a number of cell subcategories at the end of the analysis, before these purified batches can be analyzed further.

Synergistic activity of the pharmaceutical compositions of this invention in the treatment of transplant rejection may be readily determined by means of one or more tests such as but not limited to the Whole Blood Assay (hereinafter referred as WBA) as described for instance by Lin et al. in *Transplantation* (1997) 63:1734–1738. WBA is a lymphoproliferation assay performed in vitro using lymphocytes present in the whle blood, taken from animals that were previously given test substances in vivo. Hence it reflects the in vivo effect of substances as assessed by an in vitro read-out assay. The synergistic effect is evaluated by the median effect analysis method described herein-before.

The pharmaceutical composition or combined preparation with synergistic activity against immunosuppression or immunomodulation according to this invention may contain the compound of formula (II) over a broad content range depending on the contemplated use and the expected effect of the preparation. Generally, the (thio)lumazine content of the combined preparation is within the range of 0.1 to 99.9% by weight, preferably from 1 to 99% by weight, more preferably from 5 to 95% by weight.

The invention further relates to a composition or combined preparation having synergistic effects against cell proliferation and containing:
(a) one or more antineoplastic drugs, and
(b) at least one poly-substituted pteridinedione (lumazine), or a mono- or poly-substituted 2-thiolumazine, 4-thiolumazine or 2,4-dithiolumazine represented by the general formula (II), and
(c) optionally one or more pharmaceutical excipients or pharmaceutically acceptable carriers,
for simultaneous, separate or sequential use in the treatment or prevention of cell proliferative disorders.

Suitable antineoplastic drugs for inclusion into the synergistic antiproliferative pharmaceutical compositions or combined preparations of this invention are preferably selected from the group consisting of alkaloids, alkylating agents (including but not limited to alkyl sulfonates, aziridines, ethylenimines, methylmelamines, nitrogen mustards and nitrosoureas), antibiotics, antimetabolites (including but not limited to folic acid analogs, purine analogs and pyrimidine analogs), enzymes, interferon and platinum complexes.

Synergistic activity of the pharmaceutical compositions or combined preparations of this invention against cell proliferation may be readily determined by means of one or more tests such as, but not limited to, the measurement of the radioactivity resulting from the incorporation of $^3$H-thymidine in culture of tumor cell lines. For instance, different tumor cell lines are selected in order to evaluate the anti-tumor effects of the test compounds, such as but not limited to:

RPMI1788: human Peripheral Blood Leucocytes (PBL) Caucasian tumor line,

Jurkat: human acute T cell leukemia,

EL4: 57Bl/6 mouse lymphoma, or

THP-1: human monocyte tumor line.

Depending on the selected tumor cell line, different culture media may be used, such as for example:

for RPMI1788 and THP-1: RPMI-1640+10% FCS+1% NEAA+1% sodium pyruvate+$5 \times 10^{-5}$ mercaptoethanol+antibiotics (G-418 0.45 μg/ml).

for Jurkat and EL4: RPMI-1640+10% FCS+antibiotics (G-418 0.45 μg/ml).

In a specific embodiment of the synergy determination test, the tumor cell lines are harvested and a suspension of $0.27 \times 10^6$ cells/ml in whole medium is prepared. The suspensions (150 μl) are added to a microtiter plate in triplicate. Either complete medium (controls) or the test compounds at the test concentrations (50 μl) are added to the cell suspension in the microtiter plate. The cells are incubated at 37° C. under 5% $CO_2$ for about 16 hours. $^3$H-thymidine is added, and the cells incubated for another 8 hours. The cells are harvested and radioactivity is measured in counts per minute (CPM) in a β-counter. The $^3$H-thymidine cell content, and thus the measured radioactivity, is proportional to the proliferation of the cell lines. The synergistic effect is evaluated by the median effect analysis method as disclosed herein-before.

The pharmaceutical composition or combined preparation with synergistic activity against cell proliferation according to this invention may contain the (thio)lumazine compound of formula (II) over a broad content range depending on the contemplated use and the expected effect of the preparation. Generally, the (thio)lumazine content of the combined preparation is within the range of 0.1 to 99.9% by weight, preferably from 1 to 99% by weight, more preferably from 5 to 95% by weight.

The invention further relates to a pharmaceutical composition or combined preparation having synergistic effects against a viral infection and containing:
(a) one or more anti-viral agents, and
(b) at least one poly-substituted pteridinedione (lumazine), or mono- or poly-substituted 2-thiolumazine, 4-thiolumazine or 2,4-dithiolumazine represented by the general formula (II), and
(c) optionally one or more pharmaceutical excipients or pharmaceutically acceptable carriers,
for simultaneous, separate or sequential use in the treatment or prevention of a viral infection.

Suitable anti-viral agents for inclusion into the synergistic antiviral compositions or combined preparations of this invention include, for instance, retroviral enzyme inhibitors belonging to categories well known in the art, such as HIV-1

IN inhibitors, nucleoside reverse transcriptase inhibitors (e.g. zidovudine, lamivudine, didanosine, stavudine, zalcitabine and the like), non-nucleoside reverse transcriptase inhibitors (e.g. nevirapine, delavirdine and the like), other reverse transcriptase inhibitors (e.g. foscarnet sodium and the like), and HIV-1 protease inhibitors (e.g. saquinavir, ritonavir, indinavir, nelfinavir and the like). Other suitable antiviral agents include for instance acyclovir, cidofovir, cytarabine, edoxudine, famciclovir, floxuridine, ganciclovir, idoxuridine, penciclovir, sorivudine, trifluridine, valaciclovir, vidarabine, kethoxal, methisazone, moroxydine, podophyllotoxin, ribavirine, rimantadine, stallimycine, statolon, tromantadine and xenazoic acid.

Especially relevant to this aspect of the invention is the inhibition of the replication of viruses selected from the group consisting of picorna-, toga-, bunya-, orthomyxo-, paramyxo-, rhabdo-, retro-, arena-, hepatitis B-, hepatitis C-, hepatitis D-, adeno-, vaccinia-, papilloma-, herpes-, corona-, varicella- and zoster-virus, in particular human immunodeficiency virus (HIV). Synergistic activity of the pharmaceutical compositions or combined preparations of this invention against viral infection may be readily determined by means of one or more tests such as, but not limited to, the isobologram method, as previously described by Elion et al. in *J. Biol. Chem.* (1954) 208:477–488 and by Baba et al. in *Antimicrob. Agents Chemother.* (1984) 25:515–517, using $EC_{50}$ for calculating the fractional inhibitory concentration (hereinafter referred as FIC). When the minimum FIC index corresponding to the FIC of combined compounds (e.g., $FIC_x + FIC_y$) is equal to 1.0, the combination is said to be additive; when it is beween 1.0 and 0.5, the combination is defined as subsynergistic, and when it is lower than 0.5, the combination is by defined as synergistic. When the minimum FIC index is between 1.0 and 2.0, the combination is defined as subantagonistic and, when it is higher than 2.0, the combination is defined as antagonistic.

The pharmaceutical composition or combined preparation with synergistic activity against viral infection according to this invention may contain the (thio)lumazine compound of formula (II) over a broad content range depending on the contemplated use and the expected effect of the preparation. Generally, the (thio)lumazine content of the combined preparation is within the range of 0.1 to 99.9% by weight, preferably from 1 to 99% by weight, more preferably from 5 to 95% by weight.

The pharmaceutical compositions and combined preparations according to this invention may be administared orally or in any other suitable fashion. Oral administration is preferred and the preparation may have the form of a tablet, aqueous dispersion, dispersable powder or granule, emulsion, hard or soft capsule, syrup, elixir or gel. The dosing forms may be prepared using any method known in the art for manufacturing these pharmaceutical compositions and may comprise as additives sweeteners, flavoring agents, coloring agents, preservatives and the like. Carrier materials and excipients are detailed hereinbelow and may include, inter alia, calcium carbonate, sodium carbonate, lactose, calcium phosphate or sodium phosphate; granulating and disintegrating agents, binding agents and the like. The pharmaceutical composition or combined preparation may be included in a gelatin capsule mixed with any inert solid diluent or carrier material, or has the form of a soft gelatin capsule, in which the ingredient is mixed with a water or oil medium. Aqueous dispersions may comprise the biologically active composition or combined preparation in combination with a suspending agent, dispersing agent or wetting agent. Oil dispersions may comprise suspending agents such as a vegetable oil. Rectal administration is also applicable, for instance in the form of suppositories or gels. Injection is also applicable as a mode of administration, for instance in the form of injectable solutions or dispersions.

Auto-immune disorders to be prevented or treated by the pharmaceutical compositions or combined preparations of this invention include both systemic auto-immune diseases such as but not limited to lupus erythematosus, psoriasis, vasculitis, polymyositis, scleroderma, multiple sclerosis, ankylosing spondilytis, rheumatoid arthritis and Sjögren syndrome; auto-immune endocrine disorders such as thyroiditis; and organ-specific auto-immune diseases such as but not limited to Addison disease, hemolytic or pernicious anemia, Goodpasture syndrome, Graves disease, idiopathic thrombocytopenic purpura, insulin-dependent diabetes mellitus, juvenile diabetes, uveitis, Crohn's disease, ulcerative colitis, pemphigus, atopic dermatitis, autoimmune hepatitis, primary biliary cirrhosis, autoimmune pneumonitis, auto-immune carditis, myasthenia gravis, glomerulonephritis and spontaneous infertility.

Transplant rejections to be prevented or treated by the pharmaceutical compositions or combined preparations of this invention include the rejection of transplanted or grafted organs or cells (both allografts and xenografts), such as but not limited to host versus graft reaction and, especially after bone marrow transplantation, graft versus host reaction or disease. "Organ" herein means all organs or parts of organs in mammals, in particular humans, such as but not limited to kidney, lung, bone marrow, hair, cornea, eye (vitreous), heart, heart valve, liver, pancreas, blood vessel, skin, muscle, bone, intestine or stomach. "Rejection" as used herein mean all reactions of the recipient body or of the transplanted organ which in the end lead to cell or tissue death in the transplanted organ or adversely affect the functional ability and viability of the transplanted organ or the recipient. In particular, this means acute and chronic rejection reactions. Also included in this invention is preventing or treating the rejection of cell transplants and xenotransplantation. The major hurdle for xenotransplantation is that even before the T lymphocytes, responsible for the rejection of allografts, are activated, the innate immune system, especially T-independent B lymphocytes and macrophages are activated. This provokes two types of severe and early acute rejection called hyper-acute rejection and vascular rejection, respectively. The present invention addresses the problem that conventional immunosuppressant drugs like cyclosporin A are ineffective in xenotransplantation. The ability of the compounds of this invention to suppress T-independent xeno-antibody production as well as macrophage activation may be evaluated in the ability to prevent xenograft rejection in athymic, T-deficient mice receiving xenogenic hamster-heart grafts.

Cell proliferative disorders to be prevented or treated by the pharmaceutical compositions or combined preparations of this invention include not only tumor progression or invasion or metastasis inhibition of a cancer selected from the group consisting of lung cancer, leukaemia, ovarian cancer, sarcoma, Kaposi's sarcoma, meningioma, colon cancer, lymp node tumor, glioblastoma multiforme, prostate cancer or skin carcinose, but also side effects associated with current cancer therapies, including chemotherapy or radiation therapy, such as gastro-intestinal mucosal damage or radiation-induced mucositis, the treatment being based on enhancing resistance of mesenchymal cells to TNF.

CNS disorders to be prevented or treated by the pharmaceutical compositions of this invention include cognitive pathologies such as dementia, cerebral ischemia, trauma, epilepsy, schizophrenia, chronic pain and neurologic disorders such as but not limited to depression, social phobia and obsessive compulsive disorders.

Cardiovascular disorders to be prevented or treated by the pharmaceutical compositions of this invention include ischemic disorders, infarct or reperfusion damage, atherosclerosis and stroke.

The term "pharmaceutically acceptable carrier or excipient" as used herein in relation to pharmaceutical compositions and combined preparations means any material or substance with which the biologically-active ingredient(s), i.e. the (thio)lumazine of formula (II), and optionally the immunosuppressant or immunomodulator or antineoplastic drug or antiviral agent, may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders.

Suitable pharmaceutical carriers for use in the said pharmaceutical compositions and their formulation are well known to those skilled in the art. There is no particular restriction to their selection within the present invention although, due to the usually low or very low water-solubility of the poly-substituted pteridinediones (lumazines), or mono- or poly-substituted 2-thiolumazines, 4-thiolumazines and 2,4-dithiolumazines of this invention, special attention will be paid to the selection of suitable carrier combinations that can assist in properly formulating them in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, dissolving, spray-drying, coating and/or grinding the active ingredients, in a one-step or a multi-steps procedure, with the selected carrier material and, where appropriate, the other additives such as surface-active agents. may also be prepared by micronisation, for instance in view to obtain them in the form of microspheres usually having a diameter of about 1 to 10 $\mu$m, namely for the manufacture of microcapsules for controlled or sustained release of the biologically active ingredient(s).

Suitable surface-active agents to be used in the pharmaceutical compositions of the present invention are non-ionic, cationic and/or anionic materials having good emulsifying, dispersing and/or welting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$–$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzirnidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphtalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidylcholine, dipalmitoylphoshatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having 4 hydrocarbon radicals optionally substituted with halo, phenyl, substituted phenyl or hydroxy; for instance quaternary ammonium salts containing as N-substituent at least one $C_8$–$C_{22}$ alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", 2nd ed. (Hanser Verlag, Vienna, 1981) and "Encyclopaedia of Surfactants (Chemical Publishing Co., New York, 1981).

Structure-forming, thickening or gel-forming agents may be included into the pharmaceutical compositions and combined preparations of the invention. Suitable such agents are in particular highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

Gelling agents which may be included into the pharmaceutical compositions and combined preparations of the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof. Gelatin and modified celluloses represent a preferred class of gelling agents.

Other optional excipients which may be included in the pharmaceutical compositions and combined preparations of the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylene-diamine tetraacetic acid; flavoring agents such as natural vanillin; buffers such as citric acid and acetic acid; extenders or bulking agents such as silicates, diatomaceous earth, magnesium oxide or aluminum oxide; densification agents such as magnesium salts; and mixtures thereof.

Additional ingredients may be included in order to control the duration of action of the biologically-active ingredient in the compositions and combined preparations of the invention. Control release compositions may thus be achieved by selecting appropriate polymer carriers such as for example polyesters, polyamino-acids, polyvinyl-pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition or combined preparation of the invention may also require protective coatings.

Pharmaceutical forms suitable for injectable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol, complexing agents such as cyclodextrins and the like, and mixtures thereof.

Since, in the case of combined preparations including the (thio)lumazine of this invention and an immunosuppressant or immunomodulator or antineoplastic drug or antiviral agent, both ingredients do not necessarily bring out their synergistic therapeutic effect directly at the same time in the patient to be treated, the said combined preparation may be in the form of a medical kit or package containing the two ingredients in separate but adjacent form. In the latter context, each ingredient may therefore be formulated in a way suitable for an administration route different from that of the other ingredient, e.g. one of them may be in the form of an oral or parenteral formulation whereas the other is in the form of an ampoule for intravenous injection or an aerosol.

The present invention further relates to a method for preventing or treating a disease selected from the group consisting of CNS disorders, cell proliferative disorders, viral infections, immune and auto-immune disorders and transplant rejections in a subject or patient by administering to the patient in need thereof an effective amount of a (thio)lumazine compound having the general formula (II), optionally together with an effective amount of another immunosuppressant or immunomodulator or antineoplastic drug or antiviral agent, or a pharmaceutical composition such as disclosed above in extensive details. The effective amount is usually in the range of 0.01 mg to 20 mg, preferably 0.1 mg to 5 mg, per day per kg bodyweight for humans. Depending upon the pathologic condition to be treated and the patient's condition, the said effective amount may be divided into several sub-units per day or may be administered at more than one day intervals.

The present invention further relates to the use of a composition comprising:
(a) one or more immunosuppressant and/or immunomodulator drugs, and
(b) at least one (thio)lumazine represented by the general formula (II),
in respective proportions such as to provide a synergistic effect against immunosuppression or immunomodulation in a human being. Similarly the invention relates to the use of a composition comprising:
(a) one or more immunosuppressant and/or immunomodulator drugs, and
(b) at least one (thio)lumazine represented by the general formula (II),
for the manufacture of a medicine for the treatment of an immune or autoimmune disorder in a human being, in respective proportions such as to provide a synergistic effect in the said treatment.

The present invention further relates to a method for selecting or classifying potent immunosuppressive agents, particularly agents or drugs selected from the family of (thio)lumazines represented by the general formula (II). Various models may be used for testing an immunosuppressive effect. In vivo, for example, different transplantation models are available. They are strongly influenced by different immunogenicities, depending on the donor and recipient species used and depending on the nature of the transplanted organ. The survival time of transplanted organs can thus be used to measure the suppression of the immune response. In vitro, the most used models are lymphocyte activation tests. Usually activation is measured via lymphocyte proliferation. Inhibition of proliferation thus always means immunosuppression under the experimental conditions applied. There exist different stimuli for lymphocyte activation:
a) co-culture of lymphocytes of different species (mixed lymphocyte reaction, hereinafter referred as MLR) in a so-called mixed lymphocyte culture test: lymphocytes expressing different minor and major antigens of the HLA-DR type (=alloantigens) activate each other non-specifically.
b) a CD3 assay here there is an activation of the T-lymphocytes via an exogenously added antibody (OKT3). This antibody reacts against a CD3 molecule located on the lymphocyte membrane which has a costimulatory function. The interaction between OKT3 and CD3 results in T-cell activation which proceeds via the $Ca^{2+}$/calmodulin/calcineurin system and can be inhibited by cyclosporin A (hereinafter referred as CyA).

c) a CD28 assay: here specific activation of the T-lymphocyte goes also via an exogenously added antibody against a CD28 molecule which is also located on the lymphocyte membrane and delivers strong costimulatory signals. This activation is $Ca^{2+}$-independent and thus cannot be inhibited by CyA.

The selection or classification method of this invention is based on the determination of at least three lymphocyte activation in vitro tests, in particular the three parameters MLR test), aCD3 and aCD28 (abbreviations standing for "assay for cluster of differentiation 3 or cluster of differentiation 28, respectively). Preferably the three lymphocyte activation in vitro tests used for selection or classification include at least two assays for two different clusters of differentiation, the latter preferably belonging to the same general type of such clusters and more preferably belonging to type I transmembrane proteins. Optionally the selection or classification of agents or drugs of this invention may be performed on the basis of more than three lymphocyte activation in vitro tests, for instance including a TNF-α assay or an IL-1 assay or an IL-6 assay or an IL-10 assay or an IL-12 assay or an assay for a cluster of differentiation belonging to a further general type of such clusters and more preferably belonging to type II transmembrane proteins such as but not limited to CD69, CD71 or CD134.

Tables I and II summarize some of the compounds of the invention that were made and tested for biological activity, in particular lymphocyte activation, according to the above-mentioned assays and test methods.

The following examples are provided only for illustration of the invention and should in no way be understood as limiting its scope.

EXAMPLE 1

Preparation of 6-bromomethyl-1,3-dimethyllumazine

To a solution of 1,3,6-trimethyllumazine (known from Kang et al. (cited supra) (2.06 g, 0.01 mole) in acetic acid (60 ml) was added dropwise bromine (3.2 g, 0.02 mole) in acetic acid (10 ml) and the mixture was then heated under reflux for 1 hour. After cooling, acetic acid was evaporated, the residue was dissolved in $CHCl_3$ (100 ml), washed with $H_2O$ (3×70 ml), the organic layer dried over $Na_2SO_4$ and again evaporated. The residue was purified by silica gel column chromatography starting with a 9:1 toluene/ethyl acetate mixture in order to elute first 6-dibromomethyl-1,3-dimethyllumazine (1.49 g, yield 41%) and followed by a 4:1 toluene/ethyl acetate mixture to get 6-bromomethyl-1,3-dimethyllumazine (1.2 g, yield 42%). The latter was characterised by its melting point (hereinafter m.p.) of 228° C. (together with partial decomposition); by the following ultra-violet (hereinafter referred as UV) spectrum obtained in methanol (MeOH): 244 (4.16); [264 (400)]; 337 (3.86).

EXAMPLE 2

Preparation of 7-bromomethyl-1,3-dimethyllumazine

Analogous to the procedure of example 1 but starting with 1,3,7-trimethyllumazine (known from Kang et al., cited supra) (2.06 g, 0.01 mole) and bromine (3.2 g, 0.02 mole) and heating for 2 hours. Isolation by silica gel column chromatography provided first 7-dibromomethyl-1,3-dimethyllumazine (2.07 g, 57%) and second 7-bromomethyl-1,3-dimethyllumazine (0.97 g, yield 34%), the latter being characterized as follows: m.p.165–166° C.; UV (MeOH): 241 (4.23); 338 (4.02).

EXAMPLE 3

Preparation of 1,3-dimethyllumazin-6-triphenylphosphonomethyl bromide

To a suspension of the compound of example 1 (1.0 g, 3.5 mmoles) in toluene (20 ml), triphenylphosphane (1.1 g, 4.2 mmoles) was added and then heated at 80° C. in an oilbath with stirring for 8 hours. After cooling, a precipitate was collected, washed with ethyl acetate and dried at 100° C. to give 1.8 g (94%) of a colorless powder of a compound characterized as follows: m.p. 289° C.; UV (MeOH): 204 (4.74); 227 (4.52); [243 (4.42)]; [262 (4.21)]; 338 (3.88); $^1$H-NMR ($CDCl_3$): 9.55 (s, 1H), 8.00 (m, 6H), 7.75–7.63 (m, 9H), 6.09 (d, 2H), 3.62 (s, 3H) and 3.44 (s, 3H).

EXAMPLE 4

Preparation of 1,3-dimethyllumazin-7-triphenylphosphonomethyl bromide

Analogous to the procedure of example 3 but starting from the compound of example 2 and heating under reflux for 24 hours yielded 1.86 g (97%) of a compound characterized as follows: m.p. 261° C.; UV (MeOH): 204 (4.76); [221 (4.54)]; 342 (4.09); 414 (4.38).

EXAMPLE 5

Preparation of 1,3-dimethyl-6-(E)-styryllumazine

To a solution of the compound of example 3 (0.547 g, 1 mmole) in MeOH (5 ml) was added sodium methoxide (0.108 g, 2 mmoles) and the mixture was stirred at room temperature for 30 minutes. Then 1.5 mmoles of benzaldehyde (0.16 g) were added and stirring continued for 5 hours. The resulting precipitate was filtered off, washed with MeOH and purified by recrystallization from a mixture of dimethylformamide (hereinafter referred as DMF) and water to yield 0.124 g (42%) of a yellowish powder being characterized as follows: m.p. 238° C.; UV (MeOH): [220 (4.17)]; 308 (4.42); 372 (4.03); and by the following $^1$H-NMR (nuclear magnetic resonance) data obtained in $CDCl_3$: 7.78 (d, 1H); 7.62 (m, 2H); 7.45–7.30 (m, 3H); 7.30 (d, 1H); 3.74 (s, 3H); 3.57 (s, 3H).

EXAMPLE 6

Preparation of 1,3-dimethyl-6-[(E)-2-(pyrid-3-yl)vinyl]lumazine

According to the procedure of example 5 but starting with pyridine-3-carboxaldehyde (0.162 g) was obtained 0.195 g (66%) of a compound characterized as follows: m.p. 210° C.; UV (MeOH): [236 (3.92)]; 308 (4.29); 370 (3.97); $^1$H-NMR ($CDCl_3$): 8.84 (d, 1 H), 8.77 (s, 1 H); 8.57 (dd, 1 H), 7.92 (ddd, 1 H), 7.80 (d, 1 H), 7.35 (dd, 1 H), 7.34 (d, 1 H), 3.75 (s, 3 H) and 3.57 (s, 3 H).

EXAMPLE 7

Preparation of 1,3-dimethyl-6-[(E)-2-(pyrid-4-yl)vinyl]lumazine

According to the procedure of example 5 but starting with pyridine-4-carboxaldehyde (0.162 g) was obtained 0.156 g (53%) of a compound characterized as follows: m.p. 262° C.; UV (MeOH): 202 (4.20); [238 (3.92)];307 (4.51); 370 (4.20); $^1$H-NMR (CDCl$_3$): 8.77 (s, 1 H); 8.65 (m, 2 H); 7.74 (d, 1 H); 7.46 (d, 1 H); 7.45 (m, 3 H); 3.75 (s, 3 H); 3.58 (s, 3 H).

EXAMPLE 8

Preparation of 6-(1,2-dibromo-2-phenylethyl)-1,3-dimethyllumazine

To a solution of the compound of example 5 (0.735 g, 2.5 mmoles) in CHCl$_3$ (20 ml) was added bromine (0.8 g, 5 mmoles) dissolved in CHCl$_3$ (5 ml) and the mixture was then stirred at room temperature for 4 hours. It was evaporated to dryness and the residue treated with MeOH to give a colorless precipitate which was collected, washed with MeOH and dried in a vacuum desiccator, yielding 1.067 g (94%) of a compound characterized as follows: m.p. 176° C.; UV (MeOH): 245 (4.18); [260 (4.10)]; 341 (3.83); $^1$H-NMR (CDCl$_3$): 8.78 (s, 1 H); 7.55 (m, 2 H); 7.45 (m, 3 H); 5.88 (dd, 1 H); 5.79 (dd, 1 H); 3.76 (s, 3 H); 3.58 (s, 3 H).

EXAMPLE 9

Preparation of 1,3-dimethyl-6-[(E)-4-(phenyl) butadienyl]lumazine

According to the procedure of example 5 but starting with cinnamaldehyde (0.2 g) was obtained 0.138 g (43%) of a compound characterized as follows: m.p. 252° C. (with partial decomposition); UV (MeOH): 228 (4.02); [244 (3.97)]; 330 (4.66); 389 (4.23); $^1$H-NMR (CDCl$_3$): 8.65 (s, 1 H); 7.61 (dd, 1H); 7.50 (m, 2H); 7.40–7.26 (m, 3 H); 7.12–6.86 (m, 2 H); 6.83 (d, 1 H); 3.72 (s, 3 H); 3.56 (s, 3 H).

EXAMPLE 10

Preparation of 1,3-dimethyl-6-[(E)-2-methoxycarbonylethenyl]-lumazine

To a suspension of methoxycarbonylmethyl triphenylphosphonium bromide (0.415 g, 1 mmole) in dioxane (3 ml) was added 1,8-diazabicyclo[5.4.0]undec-7-ene (hereinafter referred as DBU) (0.23 g, 1.5 mmole) and the mixture was stirred at room temperature for 30 minutes. Then 1,3-dimetliyllumazine-6-carboxaldehyde (known from Kang et al., cited supra) (0.2 g, 0.91 mmoles) was added and stirring continued for 5 hours. A precipitate was collected, washed with MeOH and dried to yield 0.158 g (63%) of a colorless crystal powder being characterized as follows: m.p. 211–213° C. (with partial decomposition); UV (MeOH): 202 (4.46); [256 (4.14)]; 286 (4.21); 348 (4.08).

EXAMPLE 11

Preparation of 6-(1,2-dibromo-2-(methoxycarbonyl) ethyl)-1,3-dimethyllumazine

To a solution of the compound of example 10 (0.7 g, 2.53 mmoles) in CHCl$_3$ (20 ml) was added bromine (0.64 g, 4 mmoles) dissolved in CHCl$_3$ (5 ml) and then the mixture was stirred at room temperature for 6 hours. It was evaporated to dryness and the residue treated with MeOH to give a colorless precipitate which was collected, washed with MeOH and dried in a vacuum desiccator, yielding 0.97 g (88%) of a compound characterized as follows: m.p. 163° C.; UV (MeOH): 247 (4.16); [260 (4.08)]; 339 (3.88); $^1$H-NMR (CDCl$_3$): 8.67 (s, 1 H); 5.62 (d, 1 H); 5.33 (d, 1 H); 3.91 (s, 3 H); 3.73 (s, 3 H); 3.55 (s, 3 H).

EXAMPLE 12

Preparation of 6-(2-bromo-2-methoxycarbonyl-ethenyl)-1,3-dimethyllumazine

To a solution of the compound of example 11 (0.1 g, 0.23 mmole) in dioxane (20 ml) was added DBU (0.43 g, 0.43 mmole) and the mixture was then stirred at room temperature for 2 hours, diluted with ethyl acetate (100 ml), washed with H$_2$O (3×50 ml), the organic layer separated, dried over Na$_2$SO$_4$ and then evaporated. The residue was treated with MeOH, the solid collected and purified by recrystallization from DMF to yield 0.055 g (68%) of a yellowish powder being characterized as follows: m.p. 204° C.; UV (MeOH): [254 (4.08))]; 285 (4.25); 360 (4.01); $^1$H-NMR (CDCl$_3$): 8.55 (s, 1 H); 7.26 (s, 1H); 4.03 (s, 3 H); 3.70 (s, 3 H); 3.52 (s, 3 H).

EXAMPLE 13

Preparation of 6-chlorocarbonyl-1,3-dimethyllumazine

A suspension of 1,3-dimethyllumazine-6-carboxylic acid (known from Eisele et al. in *Pteridines* (1993) 4:178) (3.0 g, 12.7 mmoles) in dry toluene (80 ml) was treated with freshly destilled thionyl chloride (50 ml) under reflux for 3 hours. The mixture was evaporated to dryness, the residue treated with dry ether, the solid collected, washed with ether and dried in a vaccuum desiccator, yielding 3.13 g (93%) of a compound characterized as follows: m.p. 262–264° C.; UV (dioxane): 256 (4.08); [280 (4.00)]; 333 (4.03).

EXAMPLE 14

Preparation of 6-[(2-acetyl-2-ethoxycarbonyl) acetyl]-1,3-dimethyllumazine

A solution of ethyl acetoacetate ethoxy-magnesium salt (disclosed by Viscontini et al. in *Helv. Chem. Acta* (1952) 35:1342) (0.8 g, 4 mmoles) in tetrahydrofuran (hereinafter referred as THF) (8 ml) was added dropwise to a suspension of the compound of example 13 (0.51 g, 2 mmoles) in THF (10 ml) and then the mixture was stirred at room temperature for 3 days. The solvent was evaporated and the residue treated with 1 N HCl (20 ml) at 3° C. The resulting precipitate was collected, washed with H$_2$O and dried in a vacuum desiccator. Purification was achieved by column chromatography (silica gel with a CHCl$_3$/MeOH 95/5 mixture as an eluent) and the first main fraction collected. After evaporation of the eluent, the solid was recrystallized from toluene (12 ml) to yield 0.247 g (36%) of colorless crystals being characterized as follows: m.p. 153–156° C.; UV (pH 2.0): 251 (4.09); 293 (4.10); 330 (4.11); $^1$H-NMR (CDCl$_3$): 9.25 (s, 1 H); 5.95 (s, 1 H); 4.20 (q, 2 H); 3.57 (s, 3 H); 3.30 (s, 3 H); 2.43 (s, 3 H); 1.2 (t, 3 H).

EXAMPLE 15

Preparation of 6-[2,2-(diethoxycarbonyl)acetyl]-1,3-dimethyllumazine

To a solution of ethylmalonate ethoxy-magnesium salt (known from Bowman in *J. Chem. Soc.* (1950) 324 (0.685 g, 3 mmoles) in THF (12 ml) was added the compound of example 13 (0.51 g, 2 mmoles) and then the mixture was stirred at room temperature for 20 hours. The solvent was evaporated, the residue treated with 1 N HCl (20 ml) and the resulting solid collected. Recyrstallization from EtOH (40 ml) yielded 0.585 g (78%) of yellowish crystals being characterized as follows: m.p. 124–126° C.; UV (pH 2.0): 253 (4.05); 291 (4.08); 332 (4.04); $^1$H-NMR (CDCl$_3$): 9.30 (s, 1 H); 5.70 (1 H); 4.20 (q, 4H); 3.57 (s, 3 H); 3.31 (s, 3 H); 1.2 (t, 6 H).

EXAMPLE 16

Preparation of 6-(1-methoxy-2-methoxycarbonyl) ethenyl)-1,3-dimethyllumazine

A suspension of the compound of example 11 (0.2 g, 0.46 mmoles) in dry MeOH (8 ml) was treated with a solution of sodium (0.046 g, 2 mmoles) in MeOH (2 ml) at room temperature with stirring for 15 minutes. Then NH$_4$Cl (0.1 g) and H$_2$O (10 ml) were added and the mixture extracted with CHCl$_3$ (2×50 ml). The organic layer was dried over Na$_2$SO$_4$, evaporated and the residue crystallized from CHCl$_3$/n-hexane, yielding 0.085 g (60%) of a compound characterized as follows: m.p. 160° C.; UV (MeOH): 204 (4.20); 245 (4.15); 288 (4.23); 350 (3.99); $^1$H-NMR (CDCl$_3$): 8.46 (s, 1 H); 6.36 (s, 1 H); 3.85 (s, 3 H); 3.78 (s, 3 H); 3.40 (s, 3 H); 3.33 (s, 3 H).

EXAMPLE 17

Preparation of 6-[(1-hydroxy-2-nitro)ethyl]-1,3-dimethyllumazine

To a solution of nitromethane (0.61 g, 10 mmoles) and triethylamine (1.44 g, 10 mmoles) in MeOH (20 ml) was added 6-formyl-1,3-dimethyllumazine (known from Kang et al., cited supra) (2.0 g, 9 mmoles) and then the mixture was stirred at room temperature for 5 hours. The resulting precipitate was collected, washed with MeOH and ether and dried, yielding 2.22 g (78%) of a compound which, after recrystallization from CHCl$_3$, was characterized as follows: m.p. 166–167° C.; UV (MeOH): 240 (4.38); 336 (3.98); [347 (3.89)]; $^1$H-NMR (CDCl$_3$): 8.91 (s, 1 H); 6.65 (d, 1 H); 5.46 (m, 1 H); 5.05 (dd, 1 H); 4.84 (dd, 1 H); 3.55 (s, 3 H); 3.32 (s, 3 H).

EXAMPLE 18

Preparation of 1,3-dimethyl-6-[(2-nitro)ethenyl] lumazine

A solution of the compound of example 17 (0.562 g, 2 mmoles) in pyridine (10 ml) was cooled to 0° C. and then acetic anhydride (4 ml) was added dropwise. The mixture was then stirred at room temperature for 3 hours. The resulting precipitate was collected, washed with H$_2$O and dried in a vacuum desiccator to yield 0.515 g (98%) of a chromatographically pure product which, after crystallization from CHCl$_3$, was characterized as follows: m.p. 232–234° C.; UV (MeOH): [239 (3.63)]; 309 (3.87); 365 (3.95); $^1$H-NMR (CDCl$_3$): 9.18 (s, 1 H); 8.24 (d, 1 H); 8.14 (d, 1 H); 3.56 (s, 3 H); 3.33 (s, 3 H).

EXAMPLE 19

Preparation of 6-[(1-ethylthio-2-nitro)ethyl]-1,3-dimethyl-lumazine

To a suspension of the compound of example 18 (0.263 g, 1 mmole) in MeOH (5 ml) and H$_2$O (5 ml) was added ethylmercaptan (0.093 g, 1.5 mmoles) and DBU (0.2 g) and then the mixture was stirred at room temperature for 1 hour. The resulting precipitate was collected, washed and dried, yielding 0.25 g (77%) of a compound characterized as follows: m.p. 88° C.; UV (MeOH): 203 (4.28); 240 (4.26); [262 (4.05)]; 341 (3.89); $^1$H-NMR (CDCl$_3$): 9.02 (s, 1 H); 5.35–5.24 (m, 2 H); 5.01 (m, 1 H); 3.54 (s, 3 H); 3.29 (s, 3 H); 2.66–2.51 (m, 2 H); 1.13 (t, 3 H).

EXAMPLE 20

Preparation of 1,3-dimethyl-7-[(E)-2-(pyrid-2-yl) vinyl]lumazine

According to the procedure of example 5 but starting with pyridine-2-carboxaldehyde (0.162 g) and the compound of example 4 was obtained 0.233 g (79%) of a compound characterized as follows: m.p. 282–283° C.; UV (MeOH): 203 (4.14); 238 (4.23); 312 (3.95); 375 (4.36); $^1$H-NMR (CDCl$_3$): 8.70 (d, 1 H); 8.65 (s, 1H); 7.96 (d, 1 H); 7.78 (d, 1 H); 7.74 (dd, 1 H); 7.53 (d, 1H); 7.30 (dd, 1H); 3.79 (s, 3H); 3.56 (s, 3 H).

EXAMPLE 21

Preparation of 1,3-dimethyl-7-[(E)-2-(pyrid-3-yl) vinyl]lumazine

According to the procedure of example 5 but starting with pyridine-3-carboxaldehyde (0.162 g) and the compound of example 4 was obtained 0.195 g (66%) of a compound characterized as follows: m.p. 264–265° C.; UV (MeOH): 208 (4.45); 234 (4.43); [274 (4.09)]; 307 (4.08); 375 (4.48); $^1$H-NMR (CDCl$_3$): 8.87 (d, 1 H); 8.64 (dd, 1 H); 8.62 (s, 1 H); 7.98 (d, 1 H); 7.94 (d, 1 H);7.39 (dd, 1 H); 7.30 (d, 1 H); 3.80 (s, 3 H); 3.56 (s, 3 H).

EXAMPLE 22

Preparation of 1,3-dimethyl-7-[(E)-2-(pyrid-4-yl) vinyl]lumazine

According to the general procedure of example 5 but starting with pyridine-4-carboxaldehyde (0.162 g) and the compound of example 4 was obtained 0.215 g (73%) of a compound characterized as follows: m.p. 307–310° C.; UV (MeOH): 207 (4.12); 229 (4.01); 282 (3.79); [296 (3.76)]; 372 (4.00); $^1$H-NMR (CDCl$_3$): 8.70 (m, 2 H); 8.64 (s, 1 H); 7.49 (m, 2 H); 7.86 (d, 1H); 7.40 (d, 1 H); 3.80 (s, 3 H); 3.57 (s, 3 H).

EXAMPLE 23

Preparation of 1,3-dimethyl-7-[(E)-4-(phenyl) butadienyl]-lumazine

According to the procedure of example 5 but starting with cinnamaldehyde (0.2 g) and the compound of example 4 was obtained 0.195 g (61%) of a compound characterized as follows: m.p. 277–287° C. (with partial decomposition); UV (MeOH): 239 (3.79); 299 (3.66); 402 (4.15); $^1$H-NMR (CDCl$_3$): 8.49 (s, 1 H); 7.75 (dd, 1 H); 7.50 (m, 2 H); 7.41–7.28(m, 3 H); 7.11–6.65 (m, 2 H); 6.76 (d, 1 H); 3.75 (s, 3 H); 3.53 (s, 3 H).

EXAMPLE 24

Preparation of 7-[(E)-2-methoxycarbonylethenyl]-1, 3-dimethyl-lumazine

Following the procedure of example 10 but starting from 1,3-dimethyllumazine-7-carboxaldehyde (known from Kang et al., cited supra) (0.2 g, 0.91 mmoles) and stirring for 20 hours was obtained 0.15 g (60%) of a compound characterized as follows: m.p. 242–245° C. (with partial decomposition); UV (MeOH): 201 (4.21); 225 (4.29); 252 (4.20); 364 (4.11); $^1$H-NMR (CDCl$_3$): 8.63 (s, 1 H); 7.73 (d, 1 H); 7.16 (d, 1 H); 3.87 (s, 3 H); 3.74 (s, 3 H); 3.55 (s, 3 H).

EXAMPLE 25

Preparation of 7-[1,2-dibromo-2-(methoxycarbonyl)ethyl)-1,3-dimethyllumazine

To a suspension of the compound of example 24 (1.79 g, 6.5 mmoles) in CHCl$_3$ (70 ml) was added bromine (0.7 g, 14 mmoles) dissolved in CHCl$_3$ (10 ml), then the mixture was stirred at room temperature for 3 hours and evaporated to dryness. The residue was treated with MeOH to give a colorless precipitate which was collected, washed with MeOH and dried in a vacuum desiccator, yielding 2.34 g (77%) of a product which, after crystallization from EtOAc/n-hexane, was characterized as follows: m.p. 144–145° C.; UV (MeOH): 240 (4.14); 343 (3.90); $^1$H-NMR (CDCl$_3$): 8.56 (s, 1 H); 5.58 (d, 1 H); 5.15 (d, 1 H): 3.94 (s, 3 H); 3.74 (s, 3H); 3.56 (s, 3 H).

EXAMPLE 26

Preparation of 1,3-dimethyl-7-(E)-styryllumazine

According to the procedure of example 5 but starting with the compound of example 4 was obtained 0.223 g (76%) of a compound characterized as follows: m.p. 259–260° C.; UV (MeOH): 203 (4.17); 237 (4.11); 379 (4.29); $^1$H-NMR (CDCl$_3$): 8.60 (s, 1 H); 7.96 (d, 1 H); 7.65 (m, 2 H); 7.44 (m, 3 H); 7.23 (d, 1H); 3.79 (s, 3 H); 3.55 (s, 3 H).

EXAMPLE 27

Preparation of 7-(1,2-dibromo-2-phenylethyl)-1,3-dimethyllumazine

To a solution of the compound of example 26 (0.735 g, 2.5 mmoles) in CHCl$_3$ (20 ml) was added bromine (0.48 g, 3 mmoles) dissolved in CHCl$_3$ (5 ml) and the mixture was then stirred at room temperature for 3 hours. It was evaporated to dryness and the residue treated with MeOH to give a colorless precipitate which was collected, washed with MeOH and dried in a vacuum desiccator, yielding 1.08 g (95%) of a compound characterized as follows: m.p. 187–188° C.; UV (MeOH): 241 (4.25); 341 (4.06); $^1$H-NMR (CDCl$_3$): 8.68 (s, 1 H); 7.55 (m, 2 H); 7.45 (m, 3 H); 5.75 (dd, 1 H); 5.67 (dd, 1 H); 3.81 (s, 3 H); 3.57 (s, 3 H).

EXAMPLE 28

Preparation of 7-(1-bromo-2-phenyl)ethenyl-1,3-dimethyllumazine

To a suspension of the compound of example 27 (0.2 g, 0.44 mmoles) in dry MeOH (4 ml) was added a solution of sodium (0.05 g, 2.2 mmoles) in MeOH (1 ml) and then the mixture was stirred at room temperature for 3 hours. The resulting precipitate was collected, washed with MeOH and dried in vacuum, yielding 0.117 g (71%) of a yellowish powder which, after recrystallization from DMF, was characterized as follows: m.p. 245–246° C.; UV (MeOH): 243 (4.15); 372 (4.15); $^1$H-NMR (CDCl$_3$): 9.11 (s, 1 H); 8.34 (s, 1 H); 7.85 (m, 2 H); 7.45 (m, 3 H); 3.78 (s, 3 H); 3.57 (s, 3 H).

EXAMPLE 29

Preparation of 7-benzyl-1,3-dimethyllumazine

A solution of 5,6-diamino-1,3-dimethyluracil monohydrochloride (known from Pfleiderer et al. in Chem. Ber. (1973) 106:3149) (2.06 g, 0.01 mole) in H$_2$O (50 ml) was treated with benzylglyoxal (known from Dakin et al. in J. Biol. Chem. (1914) 18:42) (2.22 g, 0.015 moles) in EtOH (20 ml) and heated under reflux for 1 hour. It was diluted with H$_2$O (50 ml) and then extracted with CHCl$_3$ (5×100 ml). The organic layer was dried over Na$_2$SO$_4$, evaporated and the residue purified by silica gel column chromatography with a toluene/EtOAc 10/1 mixture as the eluent. The main fraction was collected, evaporated and crystallized from EtOH, yielding 1.7 g (61%) of a compound characterized as follows: m.p. 147–148° C.; UV (MeOH): 238 (4.22); 332 (4.07).

EXAMPLE 30

Preparation of 7-benzoyl-1,3-dimethylumazine

A suspension of the compound of example 29 (0.56 g, 2 mmoles) in H$_2$O (30 ml) was treated with KMnO$_4$ (0.6 g) and heated under reflux for 30 minutes. After cooling, it was extracted with CHCl$_3$ (3×100 ml), the organic layer dried over Na$_2$SO$_4$, filtered and evaporated to dryness. Crystallization of the solid residue from a dioxane/H$_2$O mixture yielded 0.5 g (84%) of a compound characterized as follows: m.p. 190–191° C.; UV (MeOH): 233 (4.23); [255 (4.10)]; 347 (3.97); $^1$H-NMR (CDCl$_3$): 8.57 (s, 1 H); 8.05 (m, 2 H); 7.70–7.40 (m, 3 H); 4.62 (s, 2 H); 3.65 (s, 3 H); 3.54 (s, 3 H).

EXAMPLE 31

Preparation of 7-chloro-1,3-dimethyllumazine 7-chloro-1,3-dimethyllumazine was prepared according to the procedure disclosed by Steppan et al. in Liebigs Ann. Chem. (1982) 2135. $^1$H-NMR (CDCl$_3$): 8.68(s, 1 H); 3.48 (s, 3 H); 3.31 (s, 3 H).

EXAMPLE 32

Preparation of 1,3-dimethyl-6-phenyl-7-mercaptolumazine

A mixture of 7-hydroxy-1,3-dimethyl-6-phenyllumazine (known from Pfleiderer et al., cited supra) (2.84 g, 0.01 mole) and P$_4$S$_{10}$ (3.3 g) was heated in pyridine (75 ml) under reflux for 1 hour. After cooling, the mixture was diluted with H$_2$O (50 ml) and, after standing for several hours, a yellow precipipitate (pyridinium salt, 3.3 g, 87%) appeared. This salt was dissolved in hot H$_2$O (100 ml) and acidified by HCl to pH 1. The resulting yellow crystals were collected, washed and dried in the oven, yielding 2.22 g (74%) of a compound characterized as follows: m.p. 145° C. (with partial decomposition); UV (MeOH): 203 (4.37); 227 (4.36); [283 (3.86)]; 370 (4.05); $^1$H-NMR (CDCl$_3$): 7.72 (m, 1 H); 7.62 (m, 3 H); 7.45 (m, 1 H); 3.50 (s, 3 H); 3.30 (s, 3 H).

EXAMPLE 33

Preparation of 7-ethoxy-1,3-dimethyl-6-phenyllumazine

A solution of 7-hydroxy-1,3-dimethyl-6-phenyllumazine (1.42 g, 0.005 moles) in 0.5 N NaOH (20 ml) and MeOH (10 ml) was treated with dimethyl sulfate (1 ml) and stirred for 1 hour at room temperature. The resulting precipitate was collected, washed and dried in the oven, yielding 1.26 g (81%) of a compound characterized as follows: m.p. 194° C.; UV (MeOH): 205 (4.53); [240 (4.08)]; 281 (4.22); 343 (4.23); $^1$H-NMR (CDCl$_3$): 7.96 (m, 2H); 7.50 (m, 3 H); 4.10 (s, 3 H); 3.53 (s, 3 H); 3.31 (s, 3 H).

EXAMPLE 34

Preparation of 7-chloro-1,3-dimethyl-6-phenyllumazine

A mixture of 7-hydroxy-1,3-dimethyl-6-phenyllumazine (2.84 g, 0.01 mole) and NH$_4$Cl (1 g) was heated in POCl$_3$ under reflux for 36 hours. It was evaporated to a syrup, ice was added and stirred with a glasrod till a precipitate was formed. The solid was collected, washed with H$_2$O, dried and then recrystallized from MeOH, yielding 2.36 g (78%) of a compound characterized as follows: m.p. 180° C.; UV (MeOH): 204 (4.47); 249 (4.23); 273 (4.24); 350 (4.05); $^1$H-NMR (CDCl$_3$): 7.75 (m, 2 H), 7.56 (m, 3 H), 3.54 (s, 3 H), 3.35 (s, 3 H).

EXAMPLE 35

Preparation of 6-benzyl-1,3-dimethyllumazine and 6-benzoyl-1,3-dimethyllumazine

Benzylglyoxal (2.6 g, 0.018 mole) in EtOH (80 ml) was added to a suspension of 5,6-diamino-1,3-dimethyluracil (2.0 g, 0.012 mole) in EtOH (100 ml) at room temperature for 1 hour. The solvent was evaporated under reduced pressure and the residue heated at reflux in 50% acetic acid (100 ml) for 0.5 hour. The solution was cooled down to room temperature and neutralised with ammonia water and extracted with CHCl$_3$. The organic layer was dried over Na$_2$SO$_4$ and concentrated under reduced pressure. The residue (a mixture of 6- and 7-benzyl-1,3-dimethyllumazine) was separated by column chromatography (130 g SiO$_2$) with toluene-EtOAc (10:1) to first yield 6-benzyl-1,3-dimethyllumazine (17%), then a second fraction (28%) of a mixture of the 6-benzyl and 7-benzyl-1,3-dimethyllumazine isomers and finally 7-benzyl-1,3-dimethyllumazine (1.4 g, 42%) as the late eluting fraction. The 6-benzyl-1,3-dimethyllumazine was crystallized from EtOH and characterized as follows: m.p. 139°–140° C.; $^1$H-NMR (CDCl$_3$): 8.43 (s, 1H), 7.28 (m, 5H), 4.32 (s, 2H), 3.65 (s, 3 H), 3.53 (s, 3 H).

6-benzyl-1,3-dimethyllumazine (0.56 g, 0.002 mole) and KMnO$_4$ (0.60 g, 0.004 mole) in H$_2$O (30 ml) were heated at reflux for 0.5 h. The solution was cooled down to room temperature and then extracted with CHCl$_3$. The organic layer was dried with Na$_2$SO$_4$ and evaporated under reduced pressure. The residue was crystallized from CHCl$_3$/Ether (3:20) yielding 0.49 g (85%) of a compound characterized as follows: m.p. 216°–218° C.; $^1$H-NMR (CDCl$_3$): 9.34 (s, 1H), 7.88 (m, 5H), 3.77 (s, 3H), 3.55 (s, 3H).

EXAMPLE 36

Preparation of 6-benzoyl-7,8-dihydro-1,3-dimethyl-7-(4-methoxyphenyl)lumazine

A solution of the compound of example 35 (0.2 g, 0.68 mmoles) in dry 1,2-dichloroethane (20 ml) was treated with AlCl$_3$ (0.4 g, 3 mmoles) and freshly distilled anisole (10 ml, 92 mmoles) at room temperature and stirred for 24 hours. Then ice (50 g) was added, the aquous phase was extracted with CHCl$_3$ (3×50 ml), the organic phase washed with a 2%-NaHCO$_3$ aqueous solution (50 ml) and H$_2$O (50 ml), dried over Na$_2$SO$_4$ and evaporated in high vacuum to remove excess of anisole. The residue was treated with toluene (50 ml) to obtain a yellow precipitate which, after recrystallization from a EtOH/H$_2$O 1/1 mixture, yielded 0.176 g (65%) of a compound characterized as follows: m.p. 240–244° C. (which partial decomposition); UV (MeOH): 254 (4.25); [270 (4.21)]; 406 (4.08).

EXAMPLE 37

Preparation of 6-benzoyl-1,3-dimethyl-7-(4-methoxyphenyl)lumazine

A suspension of the compound of example 36 (0.3 g, 0.74 mmoles) in dioxane (40 ml) was treated at room temperature with a 1% KMnO$_4$ aqueous solution (10 ml) by dropwise addition with stirring. After 30 minutes the excess of KMnO$_4$ was reduced by NaHSO$_3$, MnO$_2$ was filtered off, washed with warm EtOH (3×20 ml) and then the combined organic phases evaporated to dryness. The residue was purified by silica gel chromatography with a CHCl$_3$/MeOH 25/1 mixture as the eluent. The main fraction was collected, evaporated and the solid recrystallized from EtOAc with charcoal, yielding 0.175 g (59%) of a compound characterized as follows: m.p. 255–257° C.; UV (MeOH): 253 (4.24); 367 (4.10); $^1$H-NMR (CDCl$_3$): 7.95–7.85 (m, 2 H): 7.75–7.30 (m, 5 H); 3.80 (s, 6 H); 6.92 (2 H); 3.80 (s, 6 H); 3.55 (s, 3 H).

EXAMPLE 38

Preparation of 6-benzoyl-7,8-dihydro-1,3-dimethyl-7-phenyllumazine

Analogous to the procedure disclosed in example 36 but starting from the compound of example 35 (0.2 g, 0.68 mmoles) and benzene (15 ml) in place of anisole, yielding 0.21 g (83%) of a compound characterized as follows: UV (MeOH): 254 (4.26); 407 (4.12).

EXAMPLE 39

Preparation of 6-benzoyl-1,3-dimethyl-7-phenyllumazine

Analogous to the procedure disclosed in example 37 but starting from the compound of example 38 (0.3 g, 0.78 mmoles) yielded 0.18 g (62%) of a compound characterized as follows: m.p. 185–187° C.; UV (MeOH): 252 (4.39); 290 (4.08); 349 (4.16); $^1$H-NMR (CDCl$_3$): 7.95–7.25 (m, 10 H); 3.80 (s, 3 H); 3.55 (s, 3 H).

EXAMPLE 40

Preparation of 7-methoxy-1,3-dimethyl-6-styryllumazine

To a suspension of the compound of example 8 (0.2 g, 0.44 mmoles) in dry MeOH (6 ml) was added DBU (0.2 ml, 1.34 mmoles) and the mixture was then stirred at room temperature for 2 hours. The resulting precipitate was filtered off, washed with MeOH and dried in a vacuum desiccator, yielding 0.134 (94%) of a compound which, after crystallization from DMF, was characterized as follows: m.p. 271–272° C.; UV (MeOH): [232 (4.11)]; 306 (4.36); 375 (4.38); $^1$H-NMR (CDCl$_3$): 7.96 (d, 1 H); 7.62 (m, 2 H); 7.42 (d, 1 H); 7.45–7.30 (m, 3 H); 4.18 (s, 3 H); 3.69 (s, 3 H); 3.53 (s, 3 H).

EXAMPLE 41

Preparation of 1-methyl-6,7-diphenyllumazine 1-methyl-6,7-diphenyllumazine was prepared according to the procedure disclosed by Fink et al. in *Chem. Ber.* (1963) 96:2950 and characterized by $^1$H-NMR (CDCl$_3$): 11.98 (s, 1 H); 7.36 (m, 10 H); 3.53 (s, 3 H).

EXAMPLE 42

Preparation of 7-hydroxy-3-methyl-6-phenyllumazine 7-hydroxy-3-methyl-6-phenyllumazine was prepared according to the procedure disclosed by Pfleiderer et al. (cited supra) and characterized by $^1$H-NMR (CDCl$_3$): 13.1 (bs, 1 H); 12.0 (bs, 1 H); 8.02 (m, 2 H); 7.44 (m, 3 H); 3.24 (s, 3 H).

EXAMPLE 43

Preparation of 7-hydroxy-1,6-diphenyllumazine

A suspension of 6-diamino-5-nitroso-1-phenyluracil (2.32 g, 0.01 moles) in H$_2$O (50 ml) and EtOH (20 ml) was reduced by means of hydrogen in the presence of a platinum oxide catalyst in a shaking apparatus till about 450 ml of hydrogen was consumed. The mixture was heated up to 60° C., the catalyst filtered off and the filtrate treated with ethyl phenylglyoxylate (2.5 g, 0.014 mmoles) by heating under reflux for 30 minutes. The warm solution was acidified by HCl to pH 1 and the resulting precipitate was collected after cooling and re-crystallized from DMF, yielding 2.59 (78%) of a compound characterized as follows: m.p. 330° C.; UV (MeOH): 204 (4.54); [222 (4.37)]; 284 (4.17); 346 (4.25); $^1$H-NMR (DMSO): 11.81 (s, 1H); 8.01 (m, 2H); 7.50 (m, 8H).

EXAMPLE 44

Preparation of 7-hydroxy-6-phenyl-1,3-di-n-propyllumazine

A suspension of 5,6-diamino-1,3-di-n-propyluracil (1.13 g, 0.005 moles) in H$_2$O (30 ml), EtOH (5 ml) and AcOH (2 ml) was treated with ethyl phenylglyoxylate (1.25 g, 0.007 mmoles) and heated under reflux for 30 minutes until forming a brownish oil. After cooling, the latter was acidified by HCl to pH 1 whereby the oil solidified. Filtration and recrystallization from EtOH/H$_2$O yielded 1.28 g (75%) yellowish needles of a compound characterized as follows: m.p. 245° C.; UV (MeOH): 212 (4.30); [243 (4.01)]; 284 (4.02); 349 (4.19); $^1$H-NMR (CDCl$_3$): 13.4 (bs, 1 H); 8.05 (m, 2 H); 7.45 (m, 3 H); 4.09 (t, 2 H); 3.89 (t, 2 H); 1.72–1.55 (m, 4 H); 0.92–0.85 (m, 6 H).

EXAMPLES 45 TO 76

Preparation of Various Tetrasubstituted 1,3-dimethyllumazines

The following tetrasubstituted 1,3-dimethyllumazines were prepared according to methods and procedures disclosed by Matthias Wiesenfeldt, Konstanzer Dissertationen (May 1987) volume 172 (Hartung-Gorre Verlag, Konstanz, ISBN 3-89191-127-0):

6-formyl-7-hydroxy-1,3-dimethyl-lumazine (example 45),
6-hydroxy-7-formyl-1,3-dimethyl-lumazine (example 46),
6-cyano-7-chloro-1,3-dimethyl-lumazine (example 47),
6-ethylcarboxylate-7-chloro-1,3-dimethyl-lumazine (example 48),
6-(1,3-dioxolanyl)-7-chloro-1,3-dimethyl-lumazine (example 49),
6-dichloromethyl-7-chloro-1,3-dimethyl-lumazine (example 50),
6-chloro-7-cyano-1,3-dimethyl-lumazine (example 51),
6-cyano-7-isobutylamino-1,3-dimethyl-lumazine (example 52),
6-cyano-7-benzylamino-1,3-dimethyl-lumazine (example 53),
6-cyano-7-acetenylamino-1,3-dimethyl-lumazine (example 54),
6-cyano-7-cyclohexylamino-1,3-dimethyl-lumazine (example 55),
6-cyano-7-dibutylamino-1,3-dimethyl-lumazine (example 56),
6-cyano-7-imidazolyl-1,3-dimethyl-lumazine (example 57),
6-cyano-7-mercaptoisopropyl-1,3-dimethyl-lumazine (example 58),
6-cyano-7-mercaptobenzyl-1,3-dimethyl-lumazine (example 59),
6-ethylcarboxylate-7-n-butylamino-1,3-dimethyl-lumazine (example 60),
6-ethylcarboxylate-7-neopentylamino-1,3-dimethyl-lumazine (example 61),
6-ethylcarboxylate-7-(2-propenylamino)-1,3-dimethyl-lumazine (example 62),
6-ethylcarboxylate-7-piperidinyl-1,3-dimethyl-lumazine (example 63),
6-ethylcarboxylate-7-phenylhydrazino-1,3-dimethyl-lumazine (example 64),
6-ethylcarboxylate-7-mercaptoethyl-1,3-dimethyl-lumazine (example 65),
6-formyl-7-isopropylamino-1,3-dimethyl-lumazine (example 66),
6-formyl-7-hydroxyethylamino-1,3-dimethyl-lumazine (example 67),
6-formyl-7-(1-azacycloheptyl)-1,3-dimethyl-lumazine (example 68),
6-formyl-7-thiomorpholino-1,3-dimethyl-lumazine (example 69),
6-formyl-7-cyclopropylamino-1,3-dimethyl-lumazine (example 70),
6-dichloromethyl-7-mercaptobenzyl-1,3-dimethyl-lumazine (example 71),
6-dichloromethyl-7-ethylmercaptoacetate-1,3-dimethyl-lumazine (example 72),
6-benzylamino-1,3,7-trimethyl-lumazine (example 73),
6-pyrrolidinyl-1,3,7-trimethyl-lumazine (example 74),
6-chloro-7-piperidyl-1,3-diimethyl-lumazine (example 75), and
7-(2-phenylethenyl)-1,3,6-trimethyl-lumazine (example 76).

EXAMPLES 77 TO 81

Preparation of tri- and tetrasubstituted 1,3-dimethyllumazines

The following tri- and tetrasubstituted 1,3-dimethyllumazines were prepared according to methods and procedures described hereinbefore by reference to FIGS. 6 and 7:

6-[2-(p-trifluoromethylphenyl)ethenyl]-1,3-dimethyllumazine (example 77),

6-[2-(p-trifluoromethylphenyl)ethenyl]-1,3-dimethyllumazine (example 78),

6-[2-phenylethenyl]-1,3-dimethyllumazine (example 79),

6-[2-(p-trifluoromethoxyphenyl)ethenyl]-1,3-dimethyllumazine (example 80), and 6-cyano-7-ethylmercaptoacetate-1,3-dimethyllumazine (example 81).

EXAMPLE 82

Preparation of 3-methyl-6-phenyl-7-chloro-lumazine 3-methyl-6-phenyl-7-chloro-lumazine was prepared according to the general methods described hereinbefore by reference to FIG. 6.

EXAMPLES 83 TO 96

Preparation of Trisubstituted Lumazines

In a first step, trisubstituted lumazines having the general formula (I) wherein $R_1$ is hydrogen, $R_4$ is hydroxyl, and $R_2$ and $R_3$ are as indicated in the table hereunder for each of examples 83–89, were prepared according to the general methods described hereinbefore by reference to FIG. 6, in particular steps (d) and (e) thereof, and more specifically according to the following procedure:

To a suspension of a 5, 6-diamino-1-substituted uracil hydrate (10 mmole) in 200 ml water, ethyl substituted benzoylformate (12.5 mmole) was added. The resulting mixture was heated under reflux for 40 minutes. After cooling to room temperature, the precipitate was collected to yield a crude product which was re-crystallized from a MeOH/water (1/1) mixture to yield yellowish crystals or powder of the desired 7-hydroxyl tri-substituted lumazine.

| $R_2$ | $R_3$ | Example |
|---|---|---|
| methyl | phenyl | 83 |
| methyl | p-methoxyphenyl | 84 |
| methyl | p-toluyl | 85 |
| phenyl | phenyl | 86 |
| benzyl | phenyl | 87 |
| methyl | m,p-dimethoxyphenyl | 88 |
| methyl | p-chlorophenyl | 89 |

In a second step, the following 7-chloro tri-substituted lumazines:

1-methyl-6-phenyl-7-chloro-lumazine (example 90), 1-methyl-6-(4'-methoxyphenyl)-7-chloro-lumazine (example 91), 1-methyl-6-(4'-methylphenyl)-7-chloro-lumazine (example 92), 1,6-diphenyl-7-chloro-lumazine (example 93), 1-benzyl-6-phenyl-7-chloro-lumazine (example 94), 1-methyl-6-(3',4'-dimethoxyphenyl)-7-chloro-lumazine (example 95), and 1-methyl-6-(4'-chlorophenyl)-7-chloro-lumazine (example 96)

were prepared according to the general methods described hereinbefore by reference to FIG. 6, in particular step (h) thereof, and more specifically according to the following procedure:

To a suspension of 0.5 g $NH_4Cl$ in 20 ml $POCl_3$, a 7-hydroxyl tri-substituted lumazine of examples 83–89 (5 mmol) was added. The resulted mixture was heated at 90° C. till the starting material completely disappeared. The reaction mixture was concentrated under reduced pressure to a syrup and then 30 g ice was added. After 30 minutes stirring at room temperature, the precipitate was collected, washed with water and dried to yield a crude product. The latter was then purified by chromatography on silica gel (using MeOH/$CH_2Cl_2$ mixtures 1/100 to 1/20) to yield the desired 7-chloro-1-substituted-6-substituted lumazine. Crystals were obtained by re-crystallization from methanol.

Each compound of examples 90 to 96 was obtained in the following yield and characterized by the following UV (MeOH/$H_2O$) and $^1$NMR (200 MHz, DMSO-d6) spectra:

Example 90: yield 54%; UV: 238.1, 274.7, 352.1 nm; $^1$NMR: 12.1 (s, 1H), 7.74 (m, 2H), 7.56 (m, 3H) and 3.46 (s, 3H) ppm.

Example 91: yield 40%; UV: 288.9, 356.9 nm; $^1$NMR: 12.1 (s, 1H), 8.06 (d, 2H), 7.04 (d, 2H), 3.82 (s, 3H) and 3.43 (s, 3H) ppm.

Example 92: yield 58%; UV: 279.5, 355.7 nm; $^1$NMR: 12.19 (s, 1H), 7.75 (d, 2H), 7.46 (d, 2H), 3.55 (s, 3H) and 2.50 (s, 3H) ppm.

Example 93: yield 60%; UV: 274.7, 349.7 nm; $^1$NMR: 12.25 (s, 1H), 7.73 (m, 2H), 7.54 (m, 5H), 7.43 (m, 3H) and 3.36 (s, 3H) ppm.

Example 94: yield 48%; UV: 274.7, 350.9 nm; $^1$NMR: 12.20 (s, 1H), 7.74 (m, 2H), 7.55 (m, 3H), 7.35 (m, 5H), 5.28 (s, 2H) and 3.45 (s, 3H) ppm.

Example 95: yield 62%; UV: 298.4, 365.0 nm; $^1$NMR: 12.07 (s, 1H), 7.35 (d, 1H), 7.30 (s, 1H), 7.12 (d, H), 3.83 (s, 3H), 3.80 (s, 3H) and 3.44 (s, 3H) ppm.

Example 96: yield 71%; UV: 238.1, 278.3 and 352.1 nm; $^1$NMR: 12.13 (s, 1H), 7.77 (d, 2H), 7.64 (d, 2H) and 3.45 (s, 3H) ppm.

EXAMPLES 97 TO 101

Preparation of tetra-substituted 1,3-dimethyllumazines

The following tetra-substituted 1,3-dimethyllumazines:

1,3-dimethyl-6-phenyl-7-phenoxylumazine (example 97), 1,3-dimethyl-6-phenyl-7-piperidinolumazine (example 98), 1,3-dimethyl-6-phenyl-7-morpholinolumazine (example 99), 1,3-dimethyl-6-phenyl-7-(4'-N-acetyl)piperazinolumazine (example 100), and 1,3-dimethyl-6-phenyl-7-isopropylaminolumazine (example 101)

were prepared according to the general methods described hereinbefore by reference to FIG. 6, in particular step (i) thereof, and more specifically according to the following procedure:

To a mixture of 1.0 g of a 4 Angstrom molecular sieve, 200 mg CsF (1.2 mmole) in 4 ml THF, 40 mg 18-crown-6 (0.15 mmole) was added. The resulting mixture was stirred at room temperature for one hour. Then, 0.5 mmole of 6-phenyl-7-chloro-1,3-dimethyllumazine and 0.6 mmole of a reactant $HR_6$ (as defined in FIG. 6) were added respectively (this reactant is phenol in example 97, piperidine in example 98, morpholine in example 99, 4'-N-acetylpiperazine in example 100 and isopropylamine in example 101). The mixture was stirred at room temperature for another one hour, and then filtrated through a pad of Celite® (a filter agent) and rinsed with $CH_2Cl_2$. After concentration under reduced pressure, the residue was purified by chromatography on silica gel (1–5% MeOH in CH$_2$Cl$_2$) to yield the desired compound as a white or yellow powder.

Each compound of examples 97 to 101 was obtained in the following yield and characterized by the following UV (MeOH/H$_2$O) and $^1$NMR (200 MHz, DMSO-d6 for examples 97–99, CDCl$_3$ for examples 100–101) spectra:

Example 97: yield: 83%; UV: 283.0 and 348.5 nm; $^1$NMR: 8.11 (m, 2 H), 7.53 (m, 5H), 7.38 (m, 3H) and 3.33 (s, 6H) ppm.

Example 98: yield: 99%; UV: 236.9, 308.0, and 374.6 nm; $^1$NMR: 7.68 (m, 2H), 7.48 (m, 3H), 3.33 (s, 6H), 3.33 (m, 4H) and 1.52 (m, 6H) ppm.

Example 99: yield: 99%; UV: 235.7, 304.4 and 367.4 nm; $^1$NMR: 7.72 (m, 2H), 7.49 (m, 3H), 3.60 (m, 4H), 3.36 (m, 4H) and 3.33 (s, 6H) ppm.

Example 100: yield: 98%; UV: 234.5, 303.2, 367.4 nm; $^1$NMR: 7.77 (m, 2H), 7.45 (m, 3H), 3.66 (s, 1H), 3.51 (s, 3H), 3.40–3.70 (m, 8H) and 2.09 (s, 3H).

Example 101: yield: 99%; UV: 226.3, 293.7 and 354.5 nm; $^1$NMR: 7.63 (m, 2H), 7.52 (m, 3H), 5.46 (br, 1H), 4.32 (m, 1H), 3.67 (s, 3H), 3.50 (s, 3H), 2.17 (s, 3H) and 1.28 (d, 6H).

EXAMPLE 102

In Vitro Lymphocyte Activation Tests

All reagents were dissolved in 0.5 ml dimethylsulfoxide (hereinafter referred as DMSO) and further diluted in culture medium before use for the following in vitro experiments. The commercially available culture medium consisted of RPMI-1640+10% foetal calf serum (FCS).

Compounds described in some of the previous examples were tested in the three following lymphocyte activation tests:

Mixed Lymphocyte Reaction

Peripheral blood mononuclear cells (hereinafter referred as PBMC) were isolated from heparinized peripheral blood by density gradient centrifugation over Lymphoprep (Nycomed, Maorstua, Norway). Allogeneic PBMC or Eppstein-Barr Virus-transformed human B cells [commercially available under the trade name RPM11788 (ATCC name CCL156)] which strongly express B7-1 and B7-2 antigens were used as stimulator cells after irradiation with 30 Gy. MLR was performed in triplicate wells. After 5 days incubation at 37° C., 1 $\mu$Ci [$^3$ H]-thymidine was added to each cup. After a further 16 hours incubation, cells were harvested and counted in a β-counter. Inhibition of proliferation by a compound (drug) described in some of the previous examples was counted using the formula:

$$\text{Percent inhibition} = \frac{(\text{cpm} + \text{drugs}) - \text{cpm Cult. Med}}{(\text{cpm} - \text{drugs}) - \text{cpm Cult. Med}} \times 100$$

wherein cpm is the thymidine count per minute.

Assays for CD3 and CD 28

T cells were purified by removing non-T cells. Briefly, monocytes were removed by cold agglutination. The resulting lymphoid cells were further purified by a cell enrichment immunocolumn [Cellect Human T commercially available from Biotex, Edmonton, Alberta, Canada)] by a process of negative selection. More than 95% of the B cells were removed with this procedure. After depletion, the resulting T cell preparation was highly purified, i.e. these cells could not be activated by phytohaemagglutinin (PHA) or rIL-2 alone at concentrations capable of stimulating RBMC prior to deletion.

Highly purified T cells (10$^6$/ml) were stimulated by immobilized anti-CD3 or anti-CD28 monoclonal antibodies (hereinafter referred as mAb) in the presence of PMA. Anti-CD3 mAb (available from CLB, Amsterdam, Netherlands) were fixed on the 96-microwell plates by incubating the wells with 50 $\mu$l of mAb solution (1/800 dilution in culture medium). For anti-CD28 mAb (available from CLB, Amsterdam, Netherlands) 50 $\mu$l (1/650 dilution in culture medium) was added directly to the wells. Further, a 20 $\mu$l phorbol myristate acetate (hereinafter referred as PMA (commercially available from Sigma, St. Louis, Mo., USA) solution (final concentration: 0.5 ng/ml) was added. Subsequently, 20 $\mu$l of a compound described in some of the previous examples were added by serial dilution in triplicate wells. Finally 100 $\mu$l of the T-cell suspension (10$^6$/ml) was added. After 48-hour incubation at 37° C. in 5% CO$_2$, 20 $\mu$l of a bromo-deuridine (hereinafter referred as BrdU) 100 $\mu$M solution (commercially available as Cell Proliferation Elisa from Boehringer-Mannheim Belgium) was added to each well. After a further overnight incubation, T-cell proliferation was measured using a colorimetric immunoassay for qualification of cell proliferation based on the incorporation of BrdU during DNA synthesis. Optical density (hereinafter referred as OD) was measured by a Behring EL311 plate reader at 450 nm (reference wavelength: 690 nm). Inhibition of proliferation by a compound (drug) described in some of the previous examples was counted using the formula:

$$\text{Percent inhibition} = \frac{(OD + \text{drugs}) - (OD \text{ Cult. Med.})}{(OD - \text{drugs}) - (OD \text{ Cult. Med.})} \times 100$$

Table 1 herein-after shows the IC$_{50}$ values (expressed in $\mu$M) of the tested compounds, being represented by the general formula (II) wherein, unless otherwise stated (e.g. example 41 wherein R$_2$ is hydrogen; example 42 wherein R$_1$ is hydrogen; examples 44 wherein R$_1$ and R$_2$ are both n-propyl), R$_1$ and R$_2$ are both methyl, in the MLR test and in the CD3 and the CD 28 assay. The IC$_{50}$ value represents the lowest concentration (micromole per liter) of a compound that resulted in a 50% inhibition.

These results show that the (thio)lumazine compounds according to the invention exhibit a clear suppressive effect in the mixed lymphocyte reaction (MLR) test which is considered as an in vitro analogue of the transplant rejection in vivo test as it is based on the recognition of allogeneic major histocompatibility antigens (MHC) on the stimulator leukocytes, by responding lymphocytes.

TNF-alpha and IL-1 Beta Assays

Peripheral blood mononuclear cells (herein referred as PBMC), in response to stimulation by lipopolysaccharide (LPS), a gram-negative bacterial endotoxin, produce various chemokines, in particular human TNF-alpha and Il-1 beta. The inhibition of the activation of PBMC can be measured by the level of suppression of the production of TNF-alpha or IL-1 beta by PBMC in response to stimulation by LPS.

Such inhibition measurement was performed as follows: PBMC were isolated from heparinized peripheral blood (Buffy coat) by density gradient centrifugation. LPS is then added to the PMBC suspension in complete medium (10$^6$ cells /ml) at a final concentration of 1 $\mu$g/ml. The compound to be tested was added at different dilution levels, and the cells were incubated at 37° C. for 72 hours. The supernatants were collected, and TNF-alpha or Il-1 beta concentrations were measured with respectively an anti-TNF antibody or an anti-IL-1 beta antibody in a sandwich ELISA.

The percent inhibition was calculated as:

% inhibition=(pg/ml in sample–pg/ml min.)/(pg/ml max.–pg/ml min.)–1 wherein:

min.: pg/ml in culture medium without test compound, and max.: pg/ml in culture medium+LPS without test compound.

Table 2 herein-after shows the $IC_{50}$ values (expressed in $\mu M$) of the tested compounds, being represented by the general formula (II), in the MLR test and in the TNF and IL-1 assays.

The advantages to associate a (thio)lumazine compound represented by the general formula (II) with one or more other immunosuppressants are that:

the therapeutic spectrum of action of the individual components is quantitatively and qualitatively broadened, and it allows, by means of a dose reduction without reduced efficacy but with increased safety, the treatment of immune disorders which hitherto had no indication for immunosuppressive therapy as a result of side effects. At the same time, the therapy costs can be decreased to an appreciable extent.

TABLE 1

| Ex. n° | $R_3$ | $R_4$ | MLR | CD 3 | CD28 |
|---|---|---|---|---|---|
| 6 | 2-(pyrid-3-yl)vinyl | H | 30 | 110 | 110 |
| 7 | 2-(pyrid-4-yl)vinyl | H | 20 | 150 | 150 |
| 8 | 1,2-dibromo-2-phenylethyl | H | 15 | 3.4 | 1.55 |
| 9 | 4-phenylbutadienyl | H | 75 | 140 | 140 |
| 11 | 1,2-dibromo-2-(methoxycarbonyl)ethyl | H | 12 | 0.55 | 0.08 |
| 12 | 2-bromo-2-(methoxycarbonyl)ethenyl | H | 4.2 | 0.58 | 0.08 |
| 16 | 1-methoxy-2-(methoxycarbonyl)ethenyl | H | 70 | 80 | 80 |
| 17 | (1-hydroxy-2-nitro)ethyl | H | 90 | 25 | 15 |
| 18 | 2-nitroethenyl | H | 12 | 0.8 | 0.4 |
| 19 | (1-ethylthio-2-nitro)ethyl | H | 4.5 | 0.35 | 0.09 |
| 21 | H | 2-(pyrid-3-yl)vinyl | 20 | 100 | 60 |
| 22 | H | 2-(pyrid-4-yl)vinyl | 75 | 125 | 100 |
| 23 | H | 4-phenylbutadienyl | 30 | 110 | 80 |
| 24 | H | 2-(methoxycarbonyl)ethenyl | 15 | 12 | 12 |
| 25 | H | 1,2-dibromo-2-(methoxycarbonyl)ethyl | 1.9 | 0.5 | 0.5 |
| 26 | H | styryl | 50 | 115 | 115 |
| 27 | H | (1,2-dibromo-2-phenyl)ethyl | 12 | 0.6 | 0.1 |
| 28 | H | (1-bromo-2-phenyl)ethenyl | 2.7 | 2.4 | 2.7 |
| 31 | H | chloro | 12 | 0.5 | 0.1 |
| 32 | phenyl | mercapto | 25 | 25 | 25 |
| 33 | phenyl | ethoxy | 40 | 100 | 70 |
| 34 | phenyl | chloro | 3.75 | 0.08 | 0.07 |
| 40 | styryl | methoxy | 20 | >200 | >200 |
| 41 | phenyl | phenyl | 35 | 25 | 25 |
| 42 | phenyl | hydroxy | 55 | 20 | 25 |
| 44 | phenyl | hydroxy | 120 | 80 | 70 |
| 45 | formyl | hydroxy | >200 | 15.5 | 9 |
| 46 | hydroxy | formyl | 72 | 104 | 80 |
| 47 | cyano | chloro | 104 | 15 | 12 |
| 48 | ethyl carboxylate | chloro | 12.5 | 4.2 | 3.9 |
| 49 | 1,3-dioxolanyl | chloro | 11 | 2.2 | 3.6 |
| 50 | dichloromethyl | chloro | 4 | 9.5 | 9.5 |
| 51 | chloro | cyano | 116 | 56 | 56 |
| 52 | cyano | isobutylamino | 116 | 116 | 80 |
| 53 | cyano | benzylamino | 140 | 140 | 104 |
| 54 | cyano | acetylenylamino | 140 | 104 | 80 |
| 55 | cyano | cyclohexylamino | 15 | 92 | 92 |
| 56 | cyano | dibutylamino | 12 | 152 | 116 |
| 57 | cyano | imidazolyl | 48 | 16.8 | 15 |
| 58 | cyano | mercaptoisopropyl | 116 | 104 | 116 |
| 59 | cyano | mercaptobenzyl | >200 | 18.5 | 16 |
| 60 | ethyl carboxylate | n-butylamino | 13 | 56 | 92 |
| 61 | ethyl carboxylate | neopentylamino | 16 | 80 | 16 |
| 62 | ethyl carboxylate | 2-propenylamino | 60 | 92 | 56 |
| 63 | ethyl carboxylate | piperidinyl | 104 | 128 | 80 |
| 64 | ethyl carboxylate | phenylhydrazino | 20 | 56 | 12 |
| 65 | ethyl carboxylate | mercaptoethyl | 140 | 116 | 116 |
| 66 | formyl | isopropylamino | 92 | 68 | 92 |

TABLE 1-continued

| Ex. n° | R₃ | R₄ | MLR | CD 3 | CD28 |
|---|---|---|---|---|---|
| 67 | formyl | hydroxyethylamino | 104 | 104 | 104 |
| 68 | formyl | azacycloheptyl (??) | 80 | 80 | 116 |
| 69 | formyl | thiomorpholino | 116 | 80 | 116 |
| 70 | formyl | cyclopropylamino | 80 | 80 | 116 |
| 71 | dichloromethyl | mercaptobenzyl | 56 | >20 | >20 |
| 72 | dichloromethyl | ethyl mercaptoacetate | 116 | >20 | 19 |
| 73 | benzylamino | methyl | 44 | 92 | 128 |
| 74 | pyrrolidinyl | methyl | 140 | 92 | 128 |
| 75 | chloro | piperidyl | 160 | 80 | 80 |
| 76 | methyl | 2-phenyletheny | 120 | 68 | 116 |
| 77 | 2-[(p-trifluoromethyl)phenyl]ethenyl | H | 17 | >200 | 140 |
| 78 | 2-[(p-chloro)phenyl]ethenyl | H | 17 | >200 | 164 |
| 79 | 2-phenylethenyl | H | 17 | 104 | >200 |
| 80 | 2-[(p-trifluoromethoxy)phenyl]ethenyl | H | 9 | ND | ND |
| 81 | cyano | ethyl mercaptoacetate | 12.2 | ND | ND |

ND: not determined

TABLE 2

| Ex. n° | R₃ | R₄ | MLR | TNF | IL-1 |
|---|---|---|---|---|---|
| 82 | phenyl | chloro | 4.2 | 3.0 | 0.4 |
| 90 | phenyl | chloro | 4.1 | 0.5 | 0.35 |
| 91 | p-methoxyphenyl | chloro | 3.0 | 0.8 | 0.4 |
| 92 | p-toluyl | chloro | 3.6 | 1.1 | 0.5 |
| 93 | phenyl | chloro | 3.0 | 0.8 | 0.2 |
| 94 | phenyl | chloro | 4.4 | 4.5 | ND |
| 95 | m,p-dimethoxyphenyl | chloro | 5.1 | 1.1 | ND |
| 96 | p-chlorophenyl | chloro | 3.9 | 3.8 | 0.4 |

What is claimed is:

1. A poly-substituted pteridinedione (lumazine), being selected from the group consisting of:
1,3-dimethyl-6-[(E)-2-(pyrid-3-yl)vinyl]lumazine,
1,3-dimethyl-6-[(E)-2-(pyrid-4-yl)vinyl]lumazine,
6-(1,2-dibromo-2-phenylethyl)-1,3-dimethyllumazine,
1,3-dimethyl-6-[(E)-4-(phenyl)butadienyl]lumazine,
6-(1,2-dibromo-2-(methoxycarbonyl)ethyl)-1,3-dimethyllumazine,
6-(2-bromo-2-methoxycarbonyl-ethenyl)-1,3-dimethyllumazine,
6-[(2-acetyl-2-ethoxycarbonyl)acetyl]-1,3-dimethyllumazine,
6-[2,2-(diethoxycarbonyl)acetyl]-1,3-dimethyllumazine,
6-(1-methoxy-2-methoxycarbonyl)ethenyl)-1,3-dimethyllumazine,
1,3-dimethyl-6-[(2-nitro)ethenyl]lumazine,
6-[(1-hydroxy-2-nitro)ethyl]-1,3-dimethyllumazine,
6-[(1-ethylthio-2-nitro)ethyl]-1,3-dimethyllumazine,
1,3-dimethyl-7-[(E)-2-(pyrid-2-yl)vinyl]lumazine,
1,3-dimethyl-7-[(E)-2-(pyrid-3-yl)vinyl]lumazine,
1,3-dimethyl-7-[(E)-2-(pyrid-4-yl)vinyl]lumazine,
1,3-dimethyl-7-[(E)-4-(phenyl)butadienyl]lumazine,
7-1,2-dibromo-2-(methoxycarbonyl)ethyl)-1,3-dimethyllumazine,
7-[(E)-2-methoxycarbonylethenyl]lumazine,
7-(1,2-dibromo-2-phenylethyl)-1,3-dimethyllumazine,
7-(1-bromo-2-phenyl)ethenyl-1,3-dimethyllumazine,
1,3-dimethyl-7-(E)-styryllumazine,
1,3-dimethyl-6-phenyl-7-mercaptolumazine,
7-methoxy-1,3-dimethyl-6-phenyllumazine,
7-chioro-1,3-dimethyl-6-phenylluniazine,
6-benzoyl-7,8-dihydro-1,3-dimethyl-7-(4-methoxyphenyl)lumazine,
6-benzoyl-1,3-dimethyl-7-(4-methoxyphenyl)lumazine,
6-benzoyl-7,8-dihydro-1,3-dimethyl-7-phenyllumazine,
6-benzoyl-1,3-dimethyl-7-phenyllumazine,
7-methoxy-1,3-dimethyl-6-styryllumazine,
7-hydroxy-1,6-diphenyllumazine,
7-hydroxy-6-phenyl-1,3-di-n-propyllumazine,
6-formyl-7-hydroxy-1,3-dimethyl-lumazine,
6-hydroxy-7-formyl-1,3-dimethyl-lumazine,
6-cyano-7-chloro-1,3-dimethyl-lumazine,
6-ethylcarboxylate-7-chloro-1,3-dimethyl-lumazine,
6-(1,3-dioxolanyl)-7-chloro-1,3-dimethyl-lumazine,
6-dichloromethyl-7-chloro-1,3-dimethyl-lumazine,
6-chloro-7-cyano-1,3-dimethyl-lumazine,
6-cyano-7-isobutylamino-1,3-dimethyl-lumazine,
6-cyano-7-benzylamino-1,3-dimethyl-lumazine,
6-cyano-7-acetenylamino-1,3-dimethyl-lumazine,
6-cyano-7-cyclohexylamino-1,3-dimethyl-lumazine,
6-cyano-7-dibutylamino-1,3-dimethyl-lumazine,
6-cyano-7-imidazolyl-1,3-dimethyl-lumazine,
6-cyano-7-mercaptoisopropyl-1,3-dimethyl-lumazine,
6-cyano-7-mercaptobenzyl-1,3-dimethyl-lumazine,
6-ethylcarboxylate-7-n-butylamino-1,3-dimethyl-lumazine,
6-ethylcarboxylate-7-neopentylamino-1,3-dimethyl-lumazine,
6-ethylcarboxylate-7-(2-propenylamino)-1,3-dimethyl-lumazine,
6-ethylcarboxylate-7-piperidinyl-1,3-dimethyl-lumazine,
6-ethylcarboxylate-7-phenylhydrazino-1,3-dimethyl-lumazine,
6-ethylcarboxylate-7-mercaptoethyl-1,3-dimethyl-lumazine,
6-formyl-7-isopropylamino-1,3-dimethyl-lumazine,
6-formyl-7-hydroxyethylamino-1,3-dimethyl-lumazine,
6-formyl-7-(1-azacycloheptyl)-1,3-dimethyl-lumazine,
6-formyl-7-thiomorpholino-1,3-dimethyl-lumazine,
6-formyl-7-cyclopropylamino-1,3-dimethyl-lumazine,
6-dichloromethyl-7-mercaptobenzyl-1,3-dimethyl-lumazine,
6-dichloromethyl-7-ethylmercaptoacetate-1,3-dimethyl-lumazine,
6-benzylamino-1,3,7-trimethyl-lumazine,
6-pyrrolidinyl-1,3,7-trimethyl-lumazine,
6-chloro-7-piperidyl-1,3-diimethyl-lumazine,
7-(2-phenyletheny)-1,3,6-trimethyl-lumazine,
6-[2-(p-trifluoromethylphenyl)ethenyl]-1,3-dimethyllumazine, 6-[2-(p-trifluoromethylphenyl)ethenyl]-1,3-dimethyllumazine,
6-[2-phenylethenyl]-1,3-dimethyllumazine,
6-[2-(p-trifluoromethoxyphenyl)ethenyl]-1,3-dimethyllumazine,
6-cyano-7-ethylmercaptoacetate-1,3-dimethyllumazine,
3-methyl-6-phenyl-7-chloro-lumazine,
1-methyl-6-phenyl-7-hydroxy-lumazine,
1-methyl-6-(4'-methoxyphenyl)-7-hydroxy-lumazine,
1-methyl-6-(4'-methylphenyl)-7-hydroxy-lumazine,
1,6-diphenyl-7-hydroxy-lumazine,
1-benzyl-6-phenyl-7-hydroxy-lumazine,
1-methyl-6-(3',4'-dimethoxyphenyl)-7-hydroxy-lumazine,
1-methyl-6-(4'-chlorophenyl)-7-hydroxy-lumazine,
1-methyl-6-phenyl-7-chloro-lumazine,
1-methyl-6-(4'-methoxyphenyl)-7-chloro-lumazine,
1-methyl-6-(4'-methylphenyl)-7-chloro-lumazine,
1,6-diphenyl-7-chloro-lumazine,
1-benzyl-6-phenyl-7-chloro-lumazine,
1-methyl-6-(3',4'-dimethoxyphenyl)-7-chloro-lumazine,
1-methyl-6-(4'-chlorophenyl)-7-chloro-lumazine,
1,3-dimethyl-6-phenyl-7-phenoxylumazine,
1,3-dimethyl-6-phenyl-7-piperidinolumazine,
1,3-dimethyl-6-phenyl-7-morpholinolumazine,
1,3-dimethyl-6-phenyl-7-(4'-N-acetyl)piperazinolumazine, and
1,3-dimethyl-6-phenyl-7-isopropylaminolumazine.

2. A pharmaceutical composition comprising one or more pharmaceutically acceptable carriers and one or more poly-substituted pteridinediones (lumazines), selected from the group consisting of:
1,3-dimethyl-6-[(E)-2-(pyrid-3-yl)vinyl]lumazine,
1,3-dimethyl-6-[(E)-2-(pyrid-4-yl)vinyl]lumazine,
6-(1,2-dibromo-2-phenylethyl)-1,3-dimethyllumazine,
1,3-dimethyl-6-[(E)-4-(phenyl)butadienyl]lumazine,
6-(1,2-dibromo-2-(methoxycarbonyl)ethyl)-1,3-dimethyllumazine,
6-(2-bromo-2-methoxycarbonyl-ethenyl)-1,3-dimethyllumazine,
6-[(2-acetyl-2-ethoxycarbonyl)acetyl]-1,3-dimethyllumazine,
6-[2,2-(diethoxycarbonyl)acetyl]-1,3-dimethyllumazine,
6-(1-methoxy-2-methoxycarbonyl)ethenyl)-1,3-dimethyllumazine,
1,3-dimethyl-6-[(2-nitro)ethenyl]lumazine,
6-[(1-hydroxy-2-nitro)ethyl]-1,3-dimethyllumazine,
6-[(1-ethylthio-2-nitro)ethyl]-1,3-dimethyllumazine,
1,3-dimethyl-7-[(E)-2-(pyrid-2-yl)vinyl]lumazine,
1,3-dimethyl-7-[(E)-2-(pyrid-3-yl)vinyl]lumazine,
1,3-dimethyl-7-[(E)-2-(pyrid-4-yl)vinyl]lumazine,
1,3-dimethyl-7-[(E)-4-(phenyl)butadienyl]lumazine,
7-[1,2-dibromo-2-(methoxycarbonyl)ethyl]-1,3-dimethyllumazine,
7-[(E)-2-methoxycarbonylethenyl]lumazine,
7-(1,2-dibromo-2-phenylethyl)-1,3-dimethyllumazine,
7-(1-bromo-2-phenyl)ethenyl-1,3-dimethyllumazine,
1,3-dimethyl-6-(E)-styryllumazine,
1,3-dimethyl-7-(E)-styryllumazine,
1,3-dimethyl-6-phenyl-7-mercaptolumazine,
7-methoxy-1,3-dimethyl-6-phenyllumazine,
7-chloro-1,3-dimethyl-6-phenyllumazine,
6-benzoyl-7,8-dihydro-1,3-dimethyl-7-(4-methoxyphenyl)lumazine,
6-benzoyl-1,3-dimethyl-7-(4-methoxyphenyl)lumazine,
6-benzoyl-7,8-dihydro-1,3-dimethyl-7-phenyllumazine,
6-benzoyl-1,3-dimethyl-7-phenyllumazine,
7-methoxy-1,3-dimethyl-6-styryllumazine,
7-hydroxy-1,6-diphenyllumazine,
7-hydroxy-6-phenyl-1,3-di-n-propyllumazine,
6-formyl-7-hydroxy-1,3-dimethyl-lumazine,
6-hydroxy-7-formyl-1,3-dimethyl-lumazine,
6-cyano-7-chloro-1,3-dimethyl-lumazine,
6-ethylcarboxylate-7-chloro-1,3-dimethyl-lumazine,
6-(1,3-dioxolanyl)-7-chloro-1,3-dimethyl-lumazine,
6-dichloromethyl-7-chloro-1,3-dimethyl-lumazine,
6-chloro-7-cyano-1,3-dimethyl-lumazine,
6-cyano-7-isobutylamino-1,3-dimethyl-lumazine,
6-cyano-7-benzylamino-1,3-dimethyl-lumazine,
6-cyano-7-acetenylamino-1,3-dimethyl-lumazine,
6-cyano-7-cyclohexylamino-1,3-dimethyl-lumazine,
6-cyano-7-dibutylamino-1,3-dimethyl-lumazine,
6-cyano-7-imidazolyl-1,3-dimethyl-lumazine,
6-cyano-7-mercaptoisopropyl-1,3-dimethyl-lumazine,
6-cyano-7-mercaptobenzyl-1,3-dimethyl-lumazine,
6-ethylcarboxylate-7-n-butylamino-1,3-dimethyl-lumazine,
6-ethylcarboxylate-7-neopentylamino-1,3-dimethyl-lumazine,
6-ethylcarboxylate-7-(2-propenylamino)-1,3-dimethyl-lumazine,
6-ethylcarboxylate-7-piperidinyl-1,3-dimethyl-lumazine,
6-ethylcarboxylate-7-phenylhydrazino-1,3-dimethyl-lumazine,
6-ethylcarboxylate-7-mercaptoethyl-1,3-dimethyl-lumazine,
6-formyl-7-isopropylamino-1,3-dimethyl-lumazine,
6-formyl-7-hydroxyethylamino-1,3-dimethyl-lumazine,
6-formyl-7-(1-azacycloheptyl)-1,3-dimethyl-lumazine,
6-formyl-7-thiomorpholino-1,3-dimethyl-lumazine,
6-formyl-7-cyclopropylamino-1,3-dimethyl-lumazine,
6-dichloromethyl-7-mercaptobenzyl-1,3-dimethyl-lumazine,
6-dichloromethyl-7-ethylmercaptoacetate-1,3-dimethyl-lumazine,
6-benzylamino-1,3,7-trimethyl-lumazine,
6-pyrrolidinyl-1,3,7-trimethyl-lumazine,
6-chloro-7-piperidyl-1,3-diimethyl-lumazine,
7-(2-phenylethenyl)-1,3,6-trimethyl-lumazine,
6-[2-(p-trifluoromethylphenyl)ethenyl]-1,3-dimethyllumazine,
6-[2-(p-trifluoromethylphenyl)ethenyl]-1,3-dimethyllumazine,
6-[2-phenylethenyl]-1,3-dimethyllumazine,
6-[2-(p-trifluoromethoxyphenyl)ethenyl]-1,3-dimethyllumazine,
6-cyano-7-ethymercaptoacetate-1,3-dimethyllumazine,
3-methyl-6-phenyl-7-chloro-lumazine,
1-methyl-6-phenyl-7-hydroxy-lumazine,
1-methyl-6-(4'-methoxyphenyl)-7-hydroxy-lumazine,
1-methyl-6-(4'-methylphenyl)-7-hydroxy-lumazine,
1,6-diphenyl-7-hydroxy-lumazine,
1-benzyl-6-phenyl-7-hydroxy-lumazine,
1-methyl-6-(3',4'-dimethoxyphenyl)-7-hydroxy-lumazine,
1-methyl-6-(4'-chlorophenyl)-7-hydroxy-lumazine,
1-methyl-6-phenyl-7-chloro-lumazine,
1-methyl-6-(4'-methoxyphenyl)-7-chloro-lumazine,
1-methyl-6-(4'-methylphenyl)-7-chloro-lumazine,
1,6-diphenyl-7-chloro-lumazine,
1-benzyl-6-phenyl-7-chloro-lumazine,
1-methyl-6-(3',4'-dimethoxyphenyl)-7-chloro-lumazine,
1-methyl-6-(4'-chlorophenyl)-7-chloro-lumazine,
1,3-dimethyl-6-phenyl-7-phenoxylumazine,
1,3-dimethyl-6-phenyl-7-piperidinolumazine,
1,3-dimethyl-6-phenyl-7-morpholinolumazine,
1,3-dimethyl-6-phenyl-7-(4'-N-acetyl)piperazinolumazine, and 1,3-dimethyl-6-phenyl-7-isopropylaminolumazine.

3. A pharmaceutical composition according to claim 2, further comprising one or more biologically-active drugs selected from the group consisting of immunosuppressant and/or immunomodulator drugs, antineoplastic drugs, and antiviral agents.

4. A pharmaceutical composition according to 2, further comprising one or more immunosuppressant drugs selected from the group consisting of cyclosporin A; substituted xanthines, e.g. pentoxyfylline; tacrolimus; rapamycin and derivatives thereof, leflunomide or an active metabolite or an analog thereof; mycophenolic acid and salts thereof; adrenocortical steroids, azathioprine, brequinar, gusperimus, 6-mercaptopurine, mizoribine, chloroquine, hydroxychloroquine and monoclonal antibodies with immunosuppressive properties.

5. A pharmaceutical composition according to 2, further comprising one or more immunomodulator drugs selected from the group consisting of acemannan, amiprilose, bucillamine, ditiocarb sodium, imiquimod, Inosine Pranobex, interferon-β, interferon-γ, lentinan, levamisole, pidotimod, romurtide, platonin, procodazole, propagermanium, thymomodulin, thymopentin and ubenimex.

6. A pharmaceutical composition according to claim 2, further comprising one or more antineoplastic drugs selected from the group consisting of alkaloids, alkylating agents, alkyl sulfonates, aziridines, ethylenimines, methylmelamines, nitrogen mustards, nitrosoureas, antibiotics, antimetabolites, folio acid analogs, purine analogs, pyrimidine analogs, enzymes, interferon and platinum complexes.

7. A pharmaceutical composition according to claim 2, further comprising one or more antiviral agents selected from the group consisting of retroviral enzyme inhibitors, HIV-1 IN inhibitors, nucleoside reverse transcriptase inhibitors, zidovudine, lamivudine, didanosme, stavudine, zalcitabine, non-nucleoside reverse transcriptase inhibitors, nevirapine, delavirdine, other reverse transcriptase inhibitors, foscarnet sodium, HIV-1 protease inhibitors, saquinavir, ritonavir, indinavir, nelfinavir, acyclovir, cidofovir, cytarabine, edoxudine, famciclovir, floxuridine, ganciclovir, idoxuridine, penciclovir, sorivudine, trifluridine, valaciclovir, vidarabine, kethoxal, methisazone, moroxydine, podophyllotoxin, ribavirine, rimantadine, stallimycine, statolon, tromantadine and xenazoic acid.

8. A pharmaceutical composition according to claim 2, wherein said one or more pharmaceutically acceptable carriers are selected from the group consisting of wetting agents, dispersing agents, adhesives, surface-active agents, thickening agents, complexing agents, gelling agents, solvents, coatings, antibacterial and antifungal agents, isotonic agents, azo dyes; organic and inorganic pigments; UV-absorbers; stabilisers; odor masking agents; viscosity enhancers; antioxidants; preservatives; sequestering; flavoring agents; bulking agents and densification agents.

\* \* \* \* \*

UNITED STATES PATENT AND TRADEMARK OFFICE
CERTIFICATE OF CORRECTION

PATENT NO. : 6,946,465 B2
DATED : September 20, 2005
INVENTOR(S) : Waer et al.

It is certified that error appears in the above-identified patent and that said Letters Patent is hereby corrected as shown below:

Column 48,
Line 56, replace "diimethyl" with -- dimethyl --.

Column 55,
Line 65, replace "7-chioro-1,3-dimethyl-6-phenylluniazine" with -- 7-chloro-1,3-dimethyl-6-phenyllumazine --.

Column 56,
Line 64, replace "diimethyl" with -- dimethyl --.

Column 58,
Line 38, replace "diimethyl" with -- dimethyl --.
Line 47, replace "ethymercaptoacetate" with -- ethylmercaptoacetate --.

Column 59,
Lines 7 and 17, before "2", insert -- Claim --.

Column 60,
Line 1, replace "folio" with -- folic --; and
Line 8, replace "didanosme" with -- didanosine --.

Signed and Sealed this

Twenty-seventh Day of December, 2005

JON W. DUDAS
*Director of the United States Patent and Trademark Office*